(12) United States Patent
Tonkovich et al.

(10) Patent No.: US 8,383,872 B2
(45) Date of Patent: Feb. 26, 2013

(54) MULTIPHASE REACTION PROCESS USING MICROCHANNEL TECHNOLOGY

(75) Inventors: Anna Lee Tonkovich, Dublin, OH (US); David John Hesse, Columbus, OH (US); Paul Neagle, Westerville, OH (US); Micheal Jay Lamont, Hilliard, OH (US); Francis P. Daly, Delaware, OH (US); Kai Tod Paul Jarosch, Bexley, OH (US); Richard Stevenson, Columbus, OH (US); Laura J. Silva, Dublin, OH (US)

(73) Assignee: Velocys, Inc., Plain City, OH (US)

( * ) Notice: Subject to any disclaimer, the term of this patent is extended or adjusted under 35 U.S.C. 154(b) by 632 days.

(21) Appl. No.: 11/280,956

(22) Filed: Nov. 16, 2005

(65) Prior Publication Data

US 2006/0102519 A1    May 18, 2006

Related U.S. Application Data

(60) Provisional application No. 60/628,163, filed on Nov. 16, 2004, provisional application No. 60/697,900, filed on Jul. 8, 2005, provisional application No. 60/727,126, filed on Oct. 13, 2005, provisional application No. 60/731,596, filed on Oct. 27, 2005.

(51) Int. Cl.
*C07C 5/02* (2006.01)
(52) U.S. Cl. ......... 585/250; 585/263; 585/275; 585/277
(58) Field of Classification Search .................. 585/250, 585/275, 276, 277
See application file for complete search history.

(56) References Cited

U.S. PATENT DOCUMENTS

| | | | | |
|---|---|---|---|---|
| 3,792,067 A | * | 2/1974 | Coombes et al. | 554/144 |
| 4,094,909 A | * | 6/1978 | Von den Hoff | 568/354 |
| 4,163,750 A | | 8/1979 | Bird et al. | 260/409 |
| 4,278,609 A | | 7/1981 | Kuiper | 260/409 |

(Continued)

FOREIGN PATENT DOCUMENTS

| | | |
|---|---|---|
| CA | 2247662 | 3/1999 |
| EP | 0 885 086 B1 | 8/2001 |

(Continued)

OTHER PUBLICATIONS

Kestenbaum; "Synthesis of ethylene oxide in a microreaction system"; *Microreaction Technology: Industrial Prospects*; IMRET 3: Proceedings of the Third International Converence on Microreaction Technology.

(Continued)

*Primary Examiner* — Tam M Nguyen
(74) *Attorney, Agent, or Firm* — Renner, Otto, Boisselle & Sklar, LLP

(57) ABSTRACT

The disclosed invention relates to a process for conducting a multiphase reaction in a microchannel. The process comprises: forming a multiphase reaction mixture comprising a first reactant and a second reactant; the first reactant comprising at least one liquid; the second reactant comprising at least one gas, at least one liquid, or a combination of at least one gas and at least one liquid; the first reactant forming a continuous phase in the multiphase reaction mixture; the second reactant forming gas bubbles and/or liquid droplets dispersed in the continuous phase; and reacting the first reactant with the second reactant in a process microchannel in the presence of at least one catalyst to form at least one product.

102 Claims, 16 Drawing Sheets

U.S. PATENT DOCUMENTS

| | | | |
|---|---|---|---|
| 4,392,362 A | 7/1983 | Little | 62/514 |
| 4,516,632 A | 5/1985 | Swift et al. | 165/167 |
| 5,012,014 A | 4/1991 | Child et al. | 568/695 |
| 5,309,637 A | 5/1994 | Moriarty | 29/890.054 |
| 5,317,805 A | 6/1994 | Hoopman et al. | 29/890.03 |
| 5,457,251 A * | 10/1995 | Yamashita et al. | 585/269 |
| 5,597,773 A | 1/1997 | Evans et al. | 502/348 |
| 5,611,214 A | 3/1997 | Wegeng et al. | 62/498 |
| 5,684,216 A | 11/1997 | Haining | 568/896 |
| 5,689,966 A | 11/1997 | Zess et al. | 62/238.6 |
| 5,727,618 A | 3/1998 | Mundinger et al. | 165/80.4 |
| 5,811,062 A | 9/1998 | Wegeng et al. | 422/129 |
| 5,858,314 A | 1/1999 | Hsu et al. | 422/211 |
| 5,997,826 A | 12/1999 | Lodeng et al. | 422/190 |
| 6,056,932 A | 5/2000 | von Hippel et al. | 423/376 |
| 6,126,723 A | 10/2000 | Drost et al. | 96/4 |
| 6,129,973 A | 10/2000 | Martin et al. | 428/166 |
| 6,159,358 A | 12/2000 | Mulvaney, III et al. | 423/376 |
| 6,192,596 B1 | 2/2001 | Bennett et al. | 34/76 |
| 6,200,536 B1 | 3/2001 | Tonkovich et al. | 422/177 |
| 6,216,343 B1 | 4/2001 | Leland et al. | 29/890.032 |
| 6,220,497 B1 | 4/2001 | Benz et al. | 228/118 |
| 6,230,408 B1 | 5/2001 | Ehrfeld et al. | 29/890.039 |
| 6,232,262 B1 | 5/2001 | Sielcken et al. | 502/162 |
| 6,252,016 B1 | 6/2001 | Wu et al. | 526/64 |
| 6,284,217 B1 | 9/2001 | Wang et al. | 423/651 |
| 6,305,834 B1 | 10/2001 | Schubert et al. | 366/144 |
| 6,313,393 B1 | 11/2001 | Drost | 136/201 |
| 6,352,577 B1 | 3/2002 | Martin et al. | 96/4 |
| 6,359,179 B1 | 3/2002 | Nemeth et al. | 568/387 |
| 6,381,846 B2 | 5/2002 | Insley et al. | 29/890.039 |
| 6,409,072 B1 | 6/2002 | Breuer et al. | 228/111.5 |
| 6,415,860 B1 | 7/2002 | Kelly et al. | 165/748 |
| 6,432,858 B1 | 8/2002 | Tezuka | 502/22 |
| 6,440,895 B1 | 8/2002 | Tonkovich et al. | 502/439 |
| 6,451,864 B1 | 9/2002 | Wang et al. | 518/715 |
| 6,479,428 B1 | 11/2002 | Tonkovich et al. | 502/302 |
| 6,488,838 B1 | 12/2002 | Tonkovich et al. | 208/108 |
| 6,490,812 B1 | 12/2002 | Bennett et al. | 34/433 |
| 6,491,880 B1 | 12/2002 | Gao et al. | 422/211 |
| 6,503,298 B1 | 1/2003 | Monzyk et al. | 95/96 |
| 6,508,862 B1 | 1/2003 | Tonkovich et al. | 95/106 |
| 6,533,840 B2 | 3/2003 | Martin et al. | 95/45 |
| 6,540,975 B2 | 4/2003 | Tonkovich et al. | 423/659 |
| 6,558,634 B1 | 5/2003 | Wang et al. | 422/173 |
| 6,607,678 B2 | 8/2003 | Wang et al. | 252/373 |
| 6,616,909 B1 | 9/2003 | Tonkovich et al. | 423/648.1 |
| 6,622,519 B1 | 9/2003 | Mathias et al. | 62/611 |
| 6,652,627 B1 | 11/2003 | Tonkovich et al. | 95/104 |
| 6,660,237 B2 | 12/2003 | Wang et al. | 422/222 |
| 6,666,909 B1 | 12/2003 | TeGrotenhuis et al. | 95/273 |
| 6,675,875 B1 | 1/2004 | Vafai et al. | 165/80.4 |
| 6,680,044 B1 | 1/2004 | Tonkovich et al. | 423/652 |
| 6,713,036 B1 | 3/2004 | Bussche et al. | |
| 6,734,137 B2 | 5/2004 | Wang et al. | 502/328 |
| 6,746,651 B1 | 6/2004 | Ponzo et al. | 422/220 |
| 6,746,819 B1 | 6/2004 | Schmitz et al. | 430/272.1 |
| 6,747,178 B1 | 6/2004 | Harston et al. | 570/175 |
| 6,749,814 B1 | 6/2004 | Bergh et al. | 422/130 |
| 6,749,817 B1 | 6/2004 | Mulvaney, III | 422/200 |
| 6,755,211 B1 | 6/2004 | O'Connor et al. | 137/554 |
| 6,762,149 B2 | 7/2004 | Tonkovich et al. | 502/439 |
| 6,769,444 B2 | 8/2004 | Guzman et al. | 137/15.01 |
| 6,773,684 B2 | 8/2004 | Lesieur et al. | 422/198 |
| 6,814,781 B2 | 11/2004 | Tonkovich et al. | 95/90 |
| 6,851,171 B2 | 2/2005 | Schmitt | 29/469 |
| 6,916,113 B2 | 7/2005 | Van de Goor et al. | 366/108 |
| 6,932,951 B1 * | 8/2005 | Losey et al. | 422/211 |
| 6,935,768 B2 | 8/2005 | Lowe et al. | 366/167.1 |
| 6,935,772 B2 | 8/2005 | Karp et al. | 366/341 |
| 6,955,738 B2 | 10/2005 | Derand et al. | 156/272.6 |
| 6,969,746 B2 | 11/2005 | Krull et al. | 526/64 |
| 7,001,756 B1 | 2/2006 | Hsu et al. | 422/224 |
| 7,378,473 B2 | 5/2008 | Torii et al. | |
| 2001/0018140 A1 | 8/2001 | Hermann et al. | 429/20 |
| 2002/0028164 A1 | 3/2002 | Schutte et al. | 422/198 |
| 2002/0192118 A1 | 12/2002 | Zech et al. | 422/99 |
| 2003/0007904 A1 | 1/2003 | Tonkovich et al. | 422/180 |
| 2003/0045747 A1 | 3/2003 | Wurziger et al. | 562/418 |
| 2003/0103879 A1 | 6/2003 | Jahn et al. | 422/211 |
| 2003/0116503 A1 | 6/2003 | Wang et al. | 210/660 |
| 2003/0149317 A1 | 8/2003 | Rendina | 585/250 |
| 2003/0150774 A1 | 8/2003 | Lok et al. | 208/40 |
| 2003/0159530 A1 | 8/2003 | Haas et al. | 73/866 |
| 2003/0191339 A1 | 10/2003 | Schafer et al. | 560/97 |
| 2003/0199713 A1 | 10/2003 | Berg Van Den et al. | 564/489 |
| 2003/0219903 A1 | 11/2003 | Wang et al. | 436/37 |
| 2004/0034111 A1 | 2/2004 | Tonkovich et al. | 518/726 |
| 2004/0055329 A1 | 3/2004 | Mathias et al. | 62/611 |
| 2004/0104010 A1 | 6/2004 | Kenny et al. | 165/80.4 |
| 2004/0123626 A1 | 7/2004 | Caze et al. | 65/17.2 |
| 2004/0125689 A1 | 7/2004 | Ehrfeld et al. | 366/165.1 |
| 2004/0130057 A1 | 7/2004 | Mehrabi et al. | 264/171.13 |
| 2004/0131345 A1 | 7/2004 | Kylberg et al. | 392/465 |
| 2004/0131829 A1 | 7/2004 | Joseph et al. | 428/166 |
| 2004/0136902 A1 | 7/2004 | Plath et al. | 423/651 |
| 2004/0141893 A1 | 7/2004 | Martin | 422/198 |
| 2004/0143059 A1 | 7/2004 | Cabrera | 524/800 |
| 2004/0144421 A1 | 7/2004 | Parce et al. | 137/14 |
| 2004/0156762 A1 | 8/2004 | Schuppich et al. | 422/191 |
| 2004/0176651 A1 | 9/2004 | Molinier et al. | 585/258 |
| 2004/0188326 A1 | 9/2004 | Tonkovich et al. | 208/139 |
| 2004/0220434 A1 | 11/2004 | Brophy et al. | 568/959 |
| 2004/0228781 A1 | 11/2004 | Tonkovich et al. | 422/222 |
| 2004/0228882 A1 | 11/2004 | Qiu et al. | 424/400 |
| 2004/0229752 A1 | 11/2004 | Long et al. | 502/303 |
| 2004/0234566 A1 | 11/2004 | Qiu et al. | 424/401 |
| 2005/0045030 A1 | 3/2005 | Tonkovich et al. | 95/90 |
| 2005/0133457 A1 | 6/2005 | Tonkovich et al. | 210/739 |
| 2005/0152690 A1 | 7/2005 | Nagasawa et al. | 396/142 |
| 2005/0161326 A1 | 7/2005 | Morita et al. | 204/450 |
| 2005/0163701 A1 | 7/2005 | Tonkovich et al. | 423/584 |
| 2005/0165121 A1 | 7/2005 | Wang et al. | 518/726 |
| 2005/0176832 A1 | 8/2005 | Tonkovich et al. | 518/726 |
| 2005/0232076 A1 | 10/2005 | Yang et al. | 366/336 |
| 2005/0233040 A1 | 10/2005 | Ehrfeld et al. | 426/518 |
| 2005/0279491 A1 | 12/2005 | Thome et al. | 165/272 |
| 2006/0077755 A1 | 4/2006 | Higuchi et al. | 366/336 |
| 2006/0121122 A1 | 6/2006 | Nakajima et al. | 424/490 |
| 2006/0128815 A1 | 6/2006 | Clare et al. | 516/9 |

FOREIGN PATENT DOCUMENTS

| | | |
|---|---|---|
| EP | 1 311 341 B1 | 8/2001 |
| EP | 0 904 608 B1 | 12/2001 |
| EP | 1 232 790 A1 | 8/2002 |
| EP | 1 382 382 A1 | 7/2003 |
| EP | 1 362 634 A1 | 11/2003 |
| EP | 1 390 131 B1 | 7/2005 |
| EP | 1 289 660 B1 | 2/2006 |
| EP | 1 510 251 B1 | 9/2006 |
| EP | 1 726 577 A1 | 11/2006 |
| JP | 11-240904 | 8/1999 |
| JP | 2000-509330 | 7/2000 |
| JP | 2003-159527 | 6/2003 |
| JP | 2004-305939 | 11/2004 |
| JP | 05279523 | 10/2005 |
| JP | 05211857 | 11/2005 |
| JP | 05213334 | 11/2005 |
| WO | 97/32687 | 9/1997 |
| WO | 98/55812 | 12/1998 |
| WO | 99/48805 | 9/1999 |
| WO | 00/06295 | 10/2000 |
| WO | 01/10773 A1 | 2/2001 |
| WO | 01/12312 A2 | 2/2001 |
| WO | 01/54807 A1 | 8/2001 |
| WO | 01/95237 A2 | 12/2001 |
| WO | 02/14854 A1 | 2/2002 |
| WO | 02/064248 A2 | 8/2002 |
| WO | 02064248 | 8/2002 |
| WO | 03/078052 A1 | 9/2003 |
| WO | 03/106386 A2 | 12/2003 |
| WO | 2004/016347 A2 | 2/2004 |
| WO | 2004/103539 A2 | 2/2004 |
| WO | 2004/101138 A1 | 5/2004 |
| WO | 2004037399 | 5/2004 |
| WO | 2004037418 | 5/2004 |
| WO | 2004/037399 A2 | 6/2004 |

| WO | 2004/037418 A1 | 6/2004 |
| --- | --- | --- |
| WO | 2004/045760 | 6/2004 |
| WO | 2004/050799 | 6/2004 |
| WO | 2004/052518 | 6/2004 |
| WO | 2004/052530 | 6/2004 |
| WO | 2004/052941 | 6/2004 |
| WO | 2004/054013 | 6/2004 |
| WO | 2004/054696 | 7/2004 |
| WO | 2004/062790 | 7/2004 |
| WO | 2004/062791 | 7/2004 |
| WO | 2004/062792 | 7/2004 |
| WO | 2004/067160 | 8/2004 |
| WO | 2004/067444 | 8/2004 |
| WO | 2004/067492 | 8/2004 |
| WO | 2004/067708 | 8/2004 |
| WO | 2004/091771 A1 | 10/2004 |
| WO | 2004/099113 A1 | 11/2004 |
| WO | 2005/003025 A2 | 1/2005 |
| WO | 2005/058477 A1 | 6/2005 |
| WO | 2005/060658 A1 | 7/2005 |
| WO | 2005/063368 A2 | 7/2005 |
| WO | 2005/077508 A1 | 8/2005 |
| WO | 2005/079964 A1 | 9/2005 |
| WO | 2005/104323 A2 | 11/2005 |

OTHER PUBLICATIONS

Besser, Ronald S. "New Directions in Reactor Design Through Miniaturization". Sep. 13, 2002, Tulane Engineering Forum.

Ouyang et al. "Flexible Microreactor System for Chemical Research at Moderate and High Temperatures". Stevens Institute of Technology.

Gohring et al.; "Gas Phase Reactions in Ceramic Microreactors"; IMERT 6, Mar. 10-14, 2002, New Orleans, USA, AIChE Conference Proceedings 55-60.

Hsing et al.; "Simulation of Microchannel Chemical Reactors for Heterogeneous Partial Oxidation Reactions"; Chemical Engineering Science 55 (2000) 3-13.

Matlosz et al.; "Microreactors as Tools in Chemical Research"; Microreaction Technology; IMRET 5: Proceedings of the Fifth International Conference on Microreaction Technology. (May 27-30, 2001).

Srinivasn et al.; "Micromachined Reactors for Catalytic Partial Oxidation Reactions"; AIChE Journal; Nov. 1997; vol. 43, No. 11; pp. 3059-3069.

TeGrotenhuis et al.; Optimizing Microchannel Reactors by Trading-Off Equilibrium and Reaction Kinetics through Temperature Management; Prepared for presentation at IMRET 6—6$^{th}$ International Conference on Microreaction Technology; Mar. 10-14, 2002.

Wegeng et al.; "Compact Fuel Processors for Fuel Cell Powered Automobiles Based on Microchannel Technology"; Fuel Cells Bulletin No. 28; pp. 8-13.

Rostami et al.; "Flow and Heat Transfer for Gas Flowing in Microchannels: a Review"; Heat and Mass Transfer 38 (2002) 359-367.

Matlosz et al.; "Selective Oxidation of 1-Butene to Maleic Anhydride—Comparison of the Performance between Microchannel Reactors and a Fixed Bed Reactor"; Microreaction Technology; IMRET 5: Proceedings of the Fifth International Conference on Microreaction Technology. (2001).

Steinfeldt et al.; "Comparative Studies of the Oxidative Dehydrogenation of Propane in Micro-Channels Reactor Module and Fixed-Bed Reactor"; Studies in Surface Science and Catalysis; 2001 Elsevier Science B.V.; pp. 185-190.

Beretta et al.; "Production of Olefins via Oxidative Dehydrogenation of Light Paraffins at Short Contact Times"; Catalysis Today; 2001 Elsevier Science B.V.; pp. 103-111.

Waku et al.; "Effects of $O_2$ Concentration on the Rate and Selectivity in Oxidative Dehydrogenation of Ethane Catalyzed by Vanadium Oxide: Implications for $O_2$ Staging and Membrane Reactors"; Ind. Eng. Chem. Res. 2003, 41, 5462-5466.

International Search Report and Written Opinion; Application No. PCT/US2005/041486; mailed Mar. 27, 2006.

Kobayashi et al.; "A Microfluidic Device for Conducting Gas-Liquid-Solid Hydrogenation Reactions"; Science; vol. 304; May 28, 2004; pp. 1305-1308.

Poliakoff; "Hydrogenation of Organic Compounds"; www.nottingham.ac.uk/supercritical/schydrog.html; 1997.

Lawal et al.; "Microchannel Reactor System for Catalytic Hydrogenation"; AIChE, Presented at Microreaction Technology Conference (2001).

Besser; "Microdevice-Based System for Catalyst Development"; Chemical Engineering Communications; vol. 190, No. 10, Oct. 2003.

Weisse; "Carbonylation: Innovative Synthetic Routes to Known and New Products at Siemens Axiva"; CHIMICA OGGI/Chemistry Today; Sep. 2002.

Utada et al.; "Monodisperse Double Emulsions Generated from a Microcapillary Device"; Science, vol. 308, Apr. 22, 2005.

Mangnus et al.; "Hydrogenation of Oils at Reduced TFA Content"; Oils & Fats International; Jul. 2004.

Ascherio et al.; "Health effects of trans fatty acids"; Am J Clin Nutr, 1977; 66(suppl): 1006S-10S, American Society for Clinical Nutrition.

Mott Corporation, "Did you Know . . . that tiny bubbles can save you money?," OEM Manufacturing News, May 2004/.

Matlosz, Project Director, IMPLUSE News, Nov. 2005, pp. 1-4, www.impulse-project.org.

Nakajima; "Novel microchannel system for monodispersed microspheres"; RIKEN Review No. 36 (Jun. 2001); Focused on Science and Technology in Micro/Nan Scale; pp. 21-23.

Lambrich et al.; "Emulsification using microporous systems"; Journal of Membrane Science 257 (2005); pp. 76-84.

Kiwi-Minsker, et al.; "Microstructured reactors for catalytic reactions"; Catalysis Today 110 (2005); pp. 2-14.

Priest, et al.; "Generation of monodisperse gel emulsions in a microfluidic device"; Applied Physics Letters 88, 024106 (2006).

Bellefon et al.; "Asymmetric catalytic hydrogenations at micro-litre scale in a helicoidal single channel falling film micro-reactor"; Catalysis Today 110 (2005); pp. 179-187.

Drijver; "H-Cube™-Bench Top Hydrogenation Unit by Thales Nanotechnology, Inc. of Budapest Receives Prestigious R&D 100 Award"; Thales Nanotechnology; Oct. 5, 2005.

Xu et al.; "Shear force induced monodisperse droplet formation in a microfluidic device by controlling wetting properties"; Lab Chip, 2006, 6, 131-136; first published as an Advance Article on the web Nov. 1, 2005.

Abdallah et al.; "Gas-Liquid and gas-liquid-solid catalysts in a mesh microreactor"; Chem. Commun., 2004, pp. 372-373.

Angeli et al.; "Modelling of Gas-Liquid Catalytic Reactions in Microchannels"; International Conference on Microreaction Technology (2000), pp. 253-259.

Besser; Stevens Institute of Technology; A Look at Microchemical Systems (Feb. 23, 2006), pp. 1-21.

Boger; "Monolithic Catalysts for the Chemical Industry"; Ind. Eng. Chem. Res., 2004, 43, 4602-4611.

Chambers et al.; "Elemental fluorine Part 13. Gas-liquid thin film microreactors for selective direct fluorination"; Lab on a Chip, 2001, 1, 132-137.

Chambers et al.; "Elemental fluorine Part 16. Versatile thin-film-gas-liquid multi-channel microreactors for effective scale-out"; Lab Chip, 2005, 5, 191-198.

Chambers et al. "Elemental fluorine Part 18. Selective direct fluorination of 1,3-ketoesters and 1,3-diketones using gas/liquid microreactor technology"; Lab Chip, 2005, 5, 1132-1139.

Chambers et al.; "Versatile Gas/Liquid Microreactors for Industry"; Chem. Eng. Technol., 2005, 28, No. 3, pp. 344-352.

Commenge et al.; "Gas-phase residence time distribution in a falling-film microreactor"; Chemical Engineering Science 61, 2006, 597-604.

de Bellefon et al.; "Asymmetric catalytic hydrogenations at micro-litre scale ina helicoidal single channel falling film micro-reactor"; Catalysis Today 110 (2005), pp. 179-187.

Doku et al.; "On-microchip multiphase chemistry —a review of microreactor design principles and reagent contacting modes"; Tetrahedron 61 (2006), pp. 2733-2742.

McGovern et al.; "Flow Regimes in a Catalyst Trap Microreactor"; Stevens Institute of Technology.

Gunther et al.; "Transport and reaction in microscale segmented gas-liquid flow"; *Lab Chip*, 2004, 4, pp. 278-286.

Haverkamp et al.; "Characterization of a Gas/Liquid Microreactor, the Micro Bubble Column: Determination of Specific Interfacial Area"; International Conference on Microreaction Technology, 2001, pp. 202-214.

Heibel et al.; "Flooding Performance of Square Channel Monolith Structures"; *Ind. Eng. Chem. Res.* 2002, 41, pp. 6759-6771.

Heibel et al.; "Gas and liquid phase distribution and their effect on reactor performance in the monolith film flow reactor"; *Chemical Engineering Science* 56 (2001), pp. 5935-5944.

Heibel et al.; "Improving Flooding Performance for Countercurrent Monolith Reactors"; *Ind. Eng. Chem. Res.* 2004, 43, pp. 4848-4855.

Heibel et al.; "Influence of channel geometry on hydrodynamics and mass transfer in the monolith film flow reactor"; *Catalysis Today* 69 (2001), pp. 153-163.

Hessel et al.; "Gas-Liquid and Gas-Liquid-Solid Microstructured Reactors: Contacting Principles and Applications"; *Ind. Eng. Chem. Res.* 2005, 44, pp. 9750-9769.

Hessel et al.; "Gas/Liquid Microreactors for Direct Fluorination of Aromatic Compounds using Elemental Fluorine"; International Conference on Microreaction Technology, 2000, pp. 526-548.

Hessel et al.; "Gas/Liquid Microreactors: Hydrodynamics and Mass Transfer"; International Conference on Microreaction Technology, 2000, pp. 174-186.

Hessel et al.; "Microchemical Engineering: Components, Plant Concepts, User Acceptance—Part II"; *Chem. eng. Technol.* 26 (2003) 4.

Jahnisch et al.; "Direct fluorination of toluene using elemental fluorine in gas/liquid microreactors"; *Journal of Fluorine Chemistry* 105 (2000), pp. 117-128.

Khinast et al.; "Reactive mass transfer at gas-liquid interfaces: impact of micro-scale fluid dynamics on yield and selectivity of liquid-phase cyclohexane oxidation"; *Chemical Engineering Science* 58 (2003), pp. 3961-3971.

Kiwi-Minsker et al.; "Microstructured reactors for catalytic reactions"; *Catalysis Today* 110 (2005), pp. 2-14.

Koynov et al.; "Micromixing in Reactive, Deformable Bubble, and Droplet Swarms"; *Chem. Eng. Technol.* 1006, 29, No. 1, pp. 13-23.

Kreutzer et al.; "Multiphase monolith reactors: Chemical reaction engineering of segmented flow in microchannels"; *Chemical Engineering Science* 60 (2005), pp. 5895-5916.

Liu et al.; "Gas-Liquid Catalytic Hydrogenation Reaction in Small Catalyst Channel"; *AIChE Journal*, Aug. 2005, vol. 51, No. 8, pp. 2285-2297.

Losey et al.; "Design and Fabrication of Microfluidic Devices for Multiphase Mixing and Reaction"; *Journal of Microelectromechanical Systems*, vol. 11, No. 6, Dec. 2002, pp. 709-717.

Losey et al.; "A Micro Packed-Bed Reactor for Chemical Synthesis"; Department of Chemical Engineering, Massachusetts Institute of Technology, International Conference on Microreaction Technology, 2000, pp. 277-285.

Losey et al.; "Microfabricated Devices for Multiphase Catalytic Processes"; Department of Chemical Engineering, Massachusetts Institute of Technology, International Conference on Microreaction Technology, 2000, pp. 416-422.

Losey et al.; "Microfabricated Multiphase Packed-Bed Reactors: Characterization of Mass Transfer and Reactions"; *Ind. Eng. Chem. Res.* 2001, 40, pp. 2555-2562.

Lowe et al.; "Micromixing Technology"; International Conference on Microreaction Technology, 2000, pp. 31-48.

McGovern et al.; "Catalyst-Trap Microreactor for Hydrogentaiton of a Pharmaceutical Intermediate"; Stevens Institute of Technology.

Meille et al.; "Gas/Liquid Mass Transfer in Small Laboratory Batch Reactors: Comparison of Methods"; *Ind. Eng. Chem. Res.* 2004, 43, pp. 924-927.

Pestre et al.; "Effect of gas-liquid mass transfer on enantioselectivity in asymmetric hydrogenations"; *Journal of Molecular Catalysis A: Chemical* 252 (2006), pp. 85-89.

Roy et al.; "Design of monolithic catalysts for multiphase reactions"; *Chemical Engineering Science* 59 (2004), pp. 957-966.

Roy et al.; "Monoliths as Multiphase Reactors: A Review"; *AIChE Journal*, Nov. 2004, vol. 50, No. 11, pp. 2918-2938.

Yeong et al.; "Catalyst preparation and deactiviation issues for nitrobenzene hydrogenation in a microstructured falling film reactor"; *Catalysis Today* 81 (2003), pp. 641-651.

Yeong et al.; "Experimental studies of nitrobenzene hydrogenation in a microstructured falling film reactor"; *Chemical Engineering Science* 59 (2004), pp. 3491-3493.

Chen et al.; "Performance analysis of a folding flow micromixer"; Microfluid Nanofluid (2009) 6:763-774.

MacInnes et al.; "Investigation of alternating-flow mixing in microchannels"; Chemical Engineering Science 60; 2005; pp. 3453-3467.

MacInnes et al.; "Numerial characterization of floding flow microchannel mixers"; Chemical Engineering Science 62; 2007; pp. 2718-2727.

MacInnes et al.; "Mixing Strategies for Flow in Microchannel Devices"; Chemical and Process Engineering, University of Sheffield, Nov. 24, 2004.

Canadian Office Action, Application No. 2,587,546, dated Dec. 5, 2011.

Korean Office Action, Application No. 10-2010-7006518, dated Mar. 23, 2012.

Chinese Office Action, Application No. 200580046551.0, issued Jul. 16, 2010.

Chinese Office Action, Application No. 200580046551.0, issued Mar. 27, 2009.

Canadian Office Action, Application No. 2,587,546, dated Nov. 9, 2009.

Canadian Office Action, Application No. 2,587,546, dated Aug. 17, 2010.

European Office Action, Application No. 05 826 329.4-2104, dated Feb. 4, 2011.

Notification of Transmittal of the International Preliminary Report on Patentability, Application No. PCT/US2005/041486, mailed Mar. 7, 2007.

Korean Office Action, Application No. 10-2007-7013745, dated Nov. 28, 2008.

Korean Office Action, Application No. 10-2007-7013745, dated Jul. 13, 2009.

Korean Office Action, Application No. 10-2007-7013745, dated Nov. 30, 2009.

Korean Notice of Allowance, Application No. 10-2007-7013745, dated Apr. 29, 2010.

Korean Office Action, Application No. 10-2007-7006516, dated Dec. 7, 2010.

\* cited by examiner

Formed layer by tailoring

MULTIPHASE REACTION PROCESS USING MICROCHANNEL TECHNOLOGY

This application claims priority under 35 U.S.C. §119(e) to U.S. Provisional Application Ser. No. 60/628,163, filed Nov. 16, 2004, U.S. Provisional Application Ser. No. 60/697,900, filed Jul. 8, 2005, U.S. Provisional Application Ser. No. 60/727,126, filed Oct. 13, 2005, and U.S. Provisional Application Ser. No. 60/731,596, filed Oct. 27, 2005. The disclosures in these prior applications are incorporated herein by reference in their entirety.

TECHNICAL FIELD

This invention relates to a process for conducting a multiphase reaction in a microchannel reactor.

BACKGROUND

Multiphase reaction processes play an important role in the chemical and pharmaceutical industries. These processes may be classified according to the phases involved, for example, gas-liquid reactions, gas-liquid-liquid reactions, gas-liquid-solid reactions, and the like. The reactions may be catalytic or non-catalytic. The catalysts may be heterogeneous or homogeneous. However, a problem with many of these reactions is that they are difficult to conduct when compared to reactions with single phase reactants. This is due at least in part to the fact that the efficiency of interaction and mass transfer between different phases tends to be relatively low, and as a result the reaction rates tend to be relatively slow, when compared to single phase reactant reactions.

In general, to accelerate a multiphase reaction, processing steps for producing a high interfacial area between the phases are typically needed. This may include, for example, vigorous stirring or additional mixing procedures. The problem presented by the art relates to the need for a more effective process for providing a high interfacial area between different phases in a multiphase reaction process to enhance the apparent reaction rate.

SUMMARY

This invention, in at least one embodiment, provides a solution to this problem. This invention relates to a process for conducting a multiphase reaction, comprising: forming a multiphase reaction mixture comprising a first reactant and a second reactant; the first reactant comprising at least one liquid; the second reactant comprising at least one gas, at least one liquid, or a combination of at least one gas and at least one liquid; the first reactant forming a continuous phase in the multiphase reaction mixture; the second reactant forming gas bubbles and/or liquid droplets dispersed in the continuous phase; and reacting the first reactant with the second reactant in a process microchannel in the presence of at least one catalyst to form at least one product.

In one embodiment, the gas bubbles and/or liquid droplets may have a volume-based mean diameter in the range of about 0.1 to about 100 microns, and a span in the range from about 1 to about 10.

In one embodiment, heat may be exchanged between the process microchannel and a heat source and/or heat sink.

In one embodiment, the multiphase reaction mixture may be formed in the process microchannel.

In one embodiment, the process microchannel may comprise at least one is side wall and at least one apertured section extending along at least part of the axial length of the side wall, the second reactant flowing through the apertured section into the process microchannel in contact with the first reactant to form the multiphase reaction mixture. In one embodiment, the second reactant may flow from a second reactant stream channel through the apertured section.

In one embodiment, the process may be conducted in a microchannel reactor, the microchannel reactor comprising a plurality of process microchannels and at least one header for distributing the reactants to the process microchannels, the multiphase reaction mixture being formed in the header and flowing from the header into the process microchannels.

In one embodiment, the header may comprise a first reactant zone, at least one second reactant zone, and an apertured section positioned between the first reactant zone and the second reactant zone, the second reactant flowing from the second reactant zone through the apertured section into the first reactant zone in contact with the first reactant to form the multiphase reaction mixture, the multiphase reaction mixture flowing from the first reactant zone into the process microchannels.

In one embodiment, a reaction zone is in the process microchannel, the second reactant contacting the first reactant in the reaction zone to form the multiphase reaction mixture.

In one embodiment, a mixing zone and a reaction zone are in the process microchannel, the mixing zone being upstream of the reaction zone, the second reactant contacting the first reactant in the mixing zone to form the multiphase reaction mixture.

In one embodiment, a mixing zone and a reaction zone are in the process microchannel, the mixing zone being upstream of the reaction zone, the second reactant contacting the first reactant to form the multiphase reaction mixture, part of the second reactant contacting the first reactant in the mixing zone, and part of the second reactant contacting the first reactant in the reaction zone.

In one embodiment, the process microchannel may contain two or more reaction zones. The same catalyst may be used in each reaction zone or different catalysts may be used in the reaction zones. Alternatively, only one of the reaction zones may contain a catalyst, or no reaction zones may contain a catalyst.

In one embodiment, the two or more reaction zones may comprise different designs to accommodate the changing hydrodynamics of reaction along the axial length of the microchannel. The cross section of the process microchannel may be different in one reaction zone as compared to the other reaction zone. The geometry or size of surface features may also be different in one reaction zone as compared to the other reaction zone. This may be used to intensify mixing and mass transfer resistance reduction when one of the reactant phases has a higher extent of reaction than the other phase.

In one embodiment, the process microchannel may comprise surface features formed in and/or on one or more interior walls for modifying flow and/or mixing within the process microchannel. In one embodiment, surface features or capillary structures in the process microchannel downstream of the reaction zone may be used to facilitate separation of gases from liquids.

In one embodiment, the reactants may flow through a region in the reaction zone and/or mixing zone that contains surface features. The surface features may have a catalyst positioned on and/or within the surface features. The surface features may modify flow to provide intimate mixing between the reactants as the reaction proceeds.

In one embodiment, an apertured section may be positioned in a common wall separating the process microchannel and the second reactant stream channel. The second reactant feed stream may flow from the second reactant stream channel through the apertured section into the reaction zone and/or mixing zone. Surface features on or in the apertured section may be used to enhance mixing of the reactants.

In one embodiment, the second reactant stream channel may comprise surface features formed in and/or on one or more interior walls for modifying flow and/or mixing within the channel.

In one embodiment, the heat source and/or heat sink comprises at least one heat exchange channel. In one embodiment, the heat exchange channel may comprise surface features formed in and/or on one or more interior walls for modifying flow and/or mixing within the heat exchange channel.

In one embodiment, the number of process microchannels may be greater than the number of heat exchange channels, such that, for example, two or more process microchannels may exchange heat with one heat exchange channel. Two or more process microchannels may be adjacent to each other without an intervening heat exchange channel. Heat from one process microchannel may travel through an adjacent process microchannel to an adjacent heat exchange channel or a third process microchannel.

In one embodiment, particulate solids in the form of a fluidized bed may be present in the process microchannel, the process microchannel comprising surface features formed in and/or on one or more of its interior walls for modifying flow and/or mixing within the process microchannel.

In one embodiment, the apertured section may comprise a plurality of discrete feed introduction points rather than a continuous introduction of the second reactant along the axial length of the apertured section. The number of discrete feed introduction points may be any number, for example, two, three, four, five six, seven, eight, 10, 20, 50, 100, etc. The discrete feed introduction points may be advantageous for parallel reactions of different reaction order or for a series parallel reactions with different reaction orders.

In one embodiment, the inventive process may provide for more efficient reactant mixing and more precise temperature control when compared to prior art multiphase reaction processes. In one embodiment, the inventive process may provide for relatively high selectivities to the desired product. Because of the more efficient mixing that may be realized with the inventive process, reductions in the amount of one or more of the reactants that is required may be realized. As a result of process intensification that may be provided with the inventive process, lower energy utilization may be realized.

BRIEF DESCRIPTION OF THE DRAWINGS

In the annexed drawings, like parts and features have like designations.

DETAILED DESCRIPTION

Figure 1:
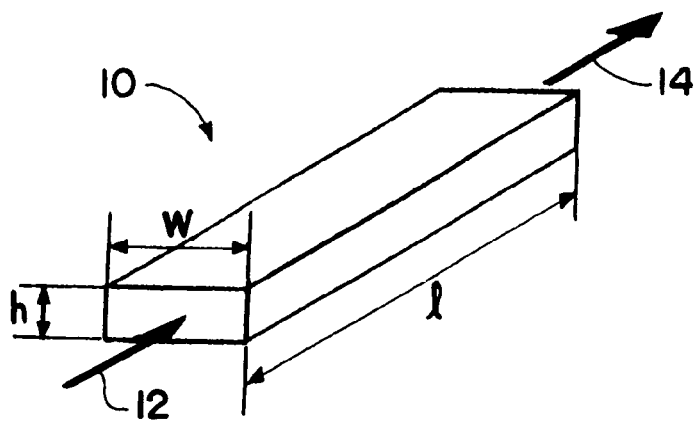
FIG. 1 is a schematic illustration of a microchannel that may be used with the inventive process.

The term "microchannel" refers to a channel having at least one internal dimension of height or width of up to about 10 millimeters (mm), and in one embodiment up to about 5 mm, and in one embodiment up to about 2 mm, and in one embodiment up to about 1 mm. An example of a microchannel that may be used with the inventive process is illustrated in FIG. 1. The microchannel 10 illustrated in FIG. 1 has a height (h), width (w) and axial length (l). The smaller of the height or width may be referred to as a gap. The bulk flow of fluid flowing through a microchannel may flow in a direction parallel to the axial length and perpendicular to both the height and width. The height (h) or width (w) of the microchannel may be in the range of about 0.05 to about 10 mm, and in one embodiment about 0.05 to about 5 mm, and in one embodiment about 0.05 to about 2 mm, and in one embodiment about 0.05 to about 1.5 mm, and in one embodiment about 0.05 to about 1 mm, and in one embodiment about 0.05 to about 0.75 mm, and in one embodiment about 0.05 to about 0.5 mm. In one embodiment the height or width may range from about 0.15 to about 10 mm, and in one embodiment from about 0.2 to about 10 mm, and in one embodiment from about 0.3 to about 10 mm. The other dimension of height or width may be of any dimension, for example, up to about 3 meters, and in one embodiment about 0.01 to about 3 meters, and in one embodiment about 0.1 to about 3 meters. The axial length (l) of the microchannel may be of any dimension, for example, up to about 10 meters, and in one embodiment in the range from about 0.05 to about 10 meters, and in one embodiment in the range from about 0.1 to about 10 meters, and in one embodiment about 0.2 to about 10 meters, and in one embodiment from about 0.2 to about 6 meters, and in one embodiment from 0.2 to about 3 meters. Although the microchannel 10 illustrated in FIG. 1 has a cross section that is rectangular, it is to be understood that the microchannel may have a cross section having any shape, for example, a square, circle, semicircle, trapezoid, etc. The shape and/or size of the cross section of the microchannel may vary over its length. For example, the height or width may taper from a relatively large dimension to a relatively small dimension, or vice versa, over the axial length of the microchannel.

The term "microchannel reactor" refers to a reactor wherein a chemical reaction is conducted in a microchannel.

The term "adjacent" when referring to the position of one channel relative to the position of another channel means directly adjacent such that a wall separates the two channels. This wall may vary in thickness. However, "adjacent" channels are not separated by an intervening channel that would interfere with heat transfer between the channels.

The term "surface feature" may refer to a depression in a microchannel wall and/or a projection from a microchannel wall that modifies flow and/or mixing within the microchannel. The surface features may be in the form of circles, oblongs, squares, rectangles, checks, chevrons, wavy shapes, and the like. The surface features may contain sub features where the major walls of the surface features further contain smaller surface features that may take the form of notches, waves, indents, holes, burrs, checks, scallops, and the like. The surface features have a depth, a width, and for non-circular surface features a length. Examples are illustrated in FIGS. 27-31. The surface features may be formed on or in one or more of the interior side walls of the process microchannels used in the inventive process. The surface features may be formed on or in one or more of the interior side walls of the second reactant stream channels and/or heat exchange channels used in the inventive process. The surface features may be referred to as passive surface features or passive mixing features. The surface features may be used to disrupt laminar flow streamlines and create advective flow at an angle to the bulk flow direction. This may enhance contact between the reactants and catalyst, especially when the catalyst is positioned on the process microchannel sidewalls or on the surface features.

The term "capillary structure" may refer to openings or passageways that are sufficiently small to preferentially retain and fill with a liquid such that a gas does not penetrate through the liquid filled openings or passageways. The capillary structure may be used for separating a gas from a liquid.

The term "fluid" refers to a gas, a liquid, or a gas or a liquid containing dispersed solids, or a mixture thereof. The fluid may be in the form of a gas containing dispersed liquid droplets. The fluid may be in the form of a liquid containing dispersed liquid or gas droplets.

The term "immiscible" refers to one liquid not being soluble in another liquid or only being soluble to the extent of up to about 1 milliliter per liter at 25° C.

The term "contact time" refers to the volume of the reaction zone within the microchannel reactor divided by the volumetric feed flow rate of a fluid flowing through the reaction zone at a temperature of 0° C. and a pressure of one atmosphere.

The term "reaction zone" refers to a space within a channel wherein a reaction takes place. The reaction zone may or may not contain a catalyst.

The term "residence time" refers to the internal volume of a space (e.g., a mixing zone within a process microchannel) occupied by a fluid flowing through the space divided by the volumetric flowrate for the fluid flowing through the space at the temperature and pressure within the space.

The term "superficial" velocity" for the velocity of a fluid flowing in a channel refers to the volumetric flow rate at standard pressure and temperature divided by the open cross sectional area of the channel.

The terms "upstream" and "downstream" refer to positions within a channel (e.g., a process microchannel) used in the inventive process that is relative to the direction of flow of a fluid stream in the channel. For example, a position within the channel not yet reached by a portion of a fluid stream flowing toward that position would be downstream of that portion of the fluid stream. A position within the channel already passed by a portion of a fluid stream flowing away from that position would be upstream of that portion of the fluid stream. The terms "upstream" and "downstream" do not necessarily refer to a vertical position since the channels used in the inventive process may be oriented horizontally, vertically or at an inclined angle.

The term "heat source" refers to a substance or device that gives off heat and may be used to heat another substance or device. The heat source may be in the form of a heat exchange channel having a heat exchange fluid in it that transfers heat to another substance or device; the another substance or device being, for example, a channel that is adjacent to or sufficiently near the heat exchange channel to receive heat transferred from the heat exchange channel. The heat exchange fluid may be contained in the heat exchange channel and/or it may flow through the heat exchange channel. The heat source may be in the form of a non-fluid heating element, for example, an electric heating element or a resistance heater.

The term "heat sink" refers to a substance or device that absorbs heat and may be used to cool another substance or device. The heat sink may be in the form of a heat exchange channel having a heat exchange fluid in it that receives heat transferred from another substance or device; the another substance or device being, for example, a channel that is adjacent to or sufficiently near the heat exchange channel to transfer heat to the heat exchange channel. The heat exchange fluid may be contained in the heat exchange channel and/or it may flow through the heat exchange channel. The heat sink may be in the form of a cooling element, for example, a non-fluid cooling element.

The term "heat source and/or heat sink" refers to a substance or a device that may give off heat or absorb heat. The heat source and/or heat sink may be in the form of a heat exchange channel having a heat exchange fluid in it that transfers heat to another substance or device adjacent to or near the heat exchange channel when the another substance or device is to be heated, or receives heat transferred from the another substance or device adjacent to or near the heat exchange channel when the another substance or device is to be cooled. The heat exchange channel functioning as a heat source and/or heat sink may function as a heating channel at times and a cooling channel at other times. A part or parts of the heat exchange channel may function as a heating channel while another part or parts of the heat exchange channel may function as a cooling channel.

The term "heat exchange channel" refers to a channel having a heat exchange fluid in it that may give off heat and/or absorb heat.

The term "heat exchange fluid" refers to a fluid that may give off heat and/or absorb heat.

The term "conversion of reactant" refers to the reactant mole change between a fluid entering a microchannel reactor and a fluid exiting the microchannel reactor divided by the moles of reactant in the fluid entering the microchannel reactor.

The term "yield" is used herein to refer to the number of moles of product exiting a microchannel reactor divided by the number of moles of first reactant entering the microchannel reactor.

The term "cycle" is used herein to refer to a single pass of the reactants through a microchannel reactor.

The term "hydrocarbon" denotes the following:

(1) Purely hydrocarbon compounds; that is, aliphatic compounds, (e.g., alkane or alkylene), alicyclic compounds (e.g., cycloalkane, cycloalkylene), aromatic compounds, aliphatic- and alicyclic-substituted aromatic compounds, aromatic-substituted aliphatic compounds, aromatic-substituted alicyclic compounds, and the like. Examples include methane, ethane, ethylene, propane, propylene, cyclohexane, ethyl cyclohexane, toluene, the xylenes, ethyl benzene, styrene, etc.

(2) Substituted hydrocarbon compounds; that is, hydrocarbon compound containing non-hydrocarbon substituents. Examples of the non-hydrocarbon substituents include hydroxyl, acyl, nitro, etc.

(3) Hetero substituted hydrocarbon compounds; that is, hydrocarbon compounds which contain atoms other than carbon in a chain or ring otherwise composed of carbon atoms. Examples of hetero atoms include, for example, nitrogen, oxygen and sulfur.

The inventive process may be suitable for conducting any chemical reaction wherein reactants in different phases are reacted together to form a desired product. These include gas-liquid reactions, liquid-liquid reactions, gas-liquid-liquid reactions, gas-liquid-solid reactions, liquid-liquid-solid reactions, and the like. The reactions that may be conducted in accordance with the inventive process include oxidation reactions, hydrocracking reactions, hydrogenation reactions, hydration reactions, carbonylation reactions, sulfation reactions, sulfonation reactions, oligomerization reactions, polymerization reactions, and the like.

The first reactant may comprise one or more liquids. When the first reactant comprises more than one liquid, the resulting liquid mixture may be in the form of a solution or a multiphase liquid mixture (for example, an emulsion). In one embodiment, the first reactant may further comprise solids dispersed in the one or more liquids. The solids may comprise catalytic particulates. Alternatively the solids may not be catalytic. The solids may be added to provide a desired product texture, adsorb wanted or unwanted by-products, intensify shear with the process microchannel, etc. The solids may be of any size provided they are small enough to be in the process microchannels. For example, the solids may have a median particle diameter in the range from about 0.01 to about 200 microns, and in one embodiment from about 1 to about 40 microns.

The second reactant may comprise one or more liquids, one or more gases, or a mixture thereof. The second reactant may comprise one or more gases containing dispersed liquid droplets or one or more liquids containing dispersed gas bubbles. The second reactant, when in the form of a gas and and introduced into the first reactant to form a multiphase reaction mixture, may form gas bubbles in the first reactant. The second reactant, when in the form of a liquid and introduced into the first reactant to form a multiphase reaction mixture, may form liquid droplets in the first reactant. When in liquid form, the second reactant may be immiscible with the first reactant. Alternatively, the multiphase reaction mixture may comprise a foam where a thin liquid film covers entrapped gas. The foam may comprise a continuous or discontinuous foam structure.

The purity of the reactants may not be critical, though it is desirable to avoid the presence of compounds which may poison the catalyst. The reactants may comprise impurities that are not reactive with the reactants.

The first and/or second reactants may comprise one or more diluent materials. Examples of such diluents include nitrogen, helium, non-reactive hydrocarbon diluents, and the like. The diluent concentration of each of the reactants may range from zero to about 99% by weight, and in one embodiment from zero to about 75% by weight, and in one embodiment from zero to about 50% by weight. Diluents may be combined with one or more of the reactants when the reactant is in gaseous form and it is desired to use a liquid as the reactant. Diluents may be used to reduce the viscosity of viscous liquid reactants. An advantage of at least one embodiment of the invention is that without the use of such diluents a more efficient and compact process may be provided.

The catalyst may be an oxidation catalyst, hydrocracking catalyst, hydrogenation catalyst, hydration catalyst, carbonylation catalyst, sulfation catalyst, sulfonation catalyst, oligomerization catalyst, polymerization catalyst, or a combination of two or more thereof.

The oxidation reactions may involve the reaction, in the presence of one or more oxidation catalysts, of one or more hydrocarbon compounds that are capable of undergoing an oxidation reaction with oxygen or a source of oxygen. The hydrocarbon compounds, which may be referred to as the first reactant, may be in the form of liquids, or they may be in the form of gases dispersed in one or more liquids. The oxygen or oxygen source, which may be referred to as the second reactant, may be in the form of a gas.

The hydrocarbon compounds that may be used in the oxidation reactions include saturated aliphatic compounds (e.g., alkanes), unsaturated aliphatic compounds (e.g., alkenes, alkynes), aldehydes, alkyl substituted aromatic compounds, alkylene substituted aromatic compounds, and the like. The saturated aliphatic compounds include alkanes containing 1 to about 25 carbon atoms per molecule, and in one embodiment 1 to about 20 carbon atoms, and in one embodiment 1 to about 10 carbon atoms. These include straight chain alkanes, single and multiple branched chain alkanes, and cyclic alkanes including cyclic alkanes having one or more alkyl groups attached to the ring. These include methane, ethane, propane, isopropane, butane, isobutane, pentane, cyclopentane, hexane, heptane, octane, 2-ethylhexane, nonane, decane, dodecane, and the like. The unsaturated aliphatic compounds include alkenes or alkylenes, and alkynes. The unsaturated aliphatic compounds may contain from 2 to about 25 carbon atoms, and in one embodiment about 2 to about 20 carbon atoms, and in one embodiment about 2 to about 10 carbon atoms. These include straight chain alkenes, single and multiple branched chain alkenes, and cyclic alkenes including cyclic alkenes having one or more alkyl and/or alkene groups attached to the ring. These include ethylene; propylene; 1-butene; 2-butene; isobutylene; 1-pentene; 2-pentene; 3-methyl-1-butene; 2-methyl-2-butene; 1-hexene; 2,3-dimethyl-2-butene; 1-heptene; 1-octene; 1-nonene; 1-decene; 1-dodecene; and the like.

The unsaturated aliphatic compounds may comprise polyenes. These include dienes, trienes, and the like. These compounds may contain from 3 to about 25 carbon atoms per molecule, and in one embodiment 3 to about 20 carbon atoms, and in one embodiment about 3 to about 10 carbon atoms. Examples include 1,2-propadiene (also known as allene); 1,3-butadiene; 2-methyl-1,3-butadiene (also known as isoprene); 1,3-pentadiene; 1,4-pentadiene; 1,5-hexadiene; 2,4-hexadiene; 2,3-dimethyl-1,3-butadiene; and the like.

The aldehydes may be saturated or unsaturated. They may be aliphatic and/or aromatic. The aldehydes may contain from 2 to about 25 carbon atoms per molecule, and in one embodiment about 2 to about 20 carbon atoms, and in one embodiment about 2 to about 10 carbon atoms. Examples include formaldehyde; acetaldehyde; propionaldehyde; n-butyraldehyde; n-valeraldehyde; caproaldehyde; acrolein; tran-2-cis-6-nonadienal; n-heptylaldehyde; trans-2-hexenal; hexadeconal; benzaldehyde; phenylacetaldehyde; o-tolualdehyde; m-tolualdehyde; p-tolualdehyde; salicylaldehyde; p-hydroxybenzaldehyde; and the like.

The alkyl or alkylene substituted aromatic compounds may contain one or more alkyl or alkylene substituents. These compounds may be monocyclic (e.g., phenyl) or a polycyclic (e.g., naphthyl). These compounds include alkyl substituted aromatic compounds containing one or more alkyl groups containing 1 to about 25 carbon atoms, and in one embodiment 1 to about 20 carbon atoms, and in one embodiment 1 to about 10 carbon atoms. These also include the akylene substituted aromatic compounds containing one or more alkylene groups containing 2 to about 25 carbon atoms, and in one embodiment 2 to about 20 carbon atoms, and in one embodiment 2 to about 10 carbon atoms. Examples include toluene, o-xylene, m-xylene, p-xylene, hemimellitene, pseudocumene, mesitylene, prehnitene, isodurene, durene, pentamethylbenzene, hexamethylbenzene, ethylbenzene, n-propylbenzene, cumene, n-butylbenzene, isobutylbenzene, sec-butylbenzene, tert-butylbenzene, p-cymene, styrene, and the like.

The oxygen or oxygen source used in the oxidation reactions may comprise molecular oxygen, air or other oxidants, such as nitrogen oxides, which can function as a source of oxygen. The oxygen source may be carbon dioxide, carbon monoxide or a peroxide (e.g., hydrogen peroxide). Gaseous mixtures containing oxygen, such as mixtures of oxygen and air, or mixtures of oxygen and an inert gas (e.g., helium, argon, etc.) or a diluent gas (e.g., carbon dioxide, water vapor, etc.) may be used. The oxygen source may comprise oxygen enriched air.

The mole ratio of the hydrocarbon reactant to oxygen may be in the range from about 0.2:1 to about 8:1, and in one embodiment about 0.5:1 to about 4:1, and in one embodiment about 1:1 to about 3:1. In one embodiment, the mole ratio may be about 2:1 or higher, and in one embodiment about 2.5:1 or higher. In one embodiment, the mole ratio may be about 1.8 or less.

The oxidation catalyst may comprise any catalyst that is useful as an oxidation catalyst. The catalyst may comprise a metal, metal oxide or mixed metal oxide of one or more of Mo, W, V, Nb, Sb, Sn, Pt, Pd, Cs, Zr, Cr, Mg, Mn, Ni, Co, Ce, or a mixture of two or more thereof. These catalysts may also comprise one or more alkali metals or alkaline earth metals or other transition metals, rare earth metals, or lanthanides. Additionally elements such as P and Bi may be present. The catalyst may be supported, and if so, useful support materials include metal oxides (e.g., alumina, titania, zirconia), silica, mesoporous materials, zeolites, refractory materials, or combinations of two or more thereof. The form which these catalysts may be in is discussed in greater detail below.

The product formed by the oxidation reaction may comprise one or more oxygenates. The term "oxygenate" is used herein to refer to a hydrocarbon compound that contains at least one oxygen. The oxygenates include alcohols, epoxides, aldehydes, ketones, carboxylic acids, carboxylic acid anhydrides, esters, and the like. The oxygenates include, with the exception of the epoxides and esters, one or more of the above-indicated oxygenates containing 1 to about 25 carbon atoms per molecule, and in one embodiment 1 to about 20 carbon atoms, and in one embodiment 1 to about 10 carbon atoms. The epoxides and esters must contain at least 2 carbon atoms, but in all other respects would include compounds within the above-indicated ranges, for example, 2 to about 25 carbon atoms, etc. The alcohols include monools and polyols. Specific examples include methanol, ethyl alcohol, propyl alcohol, butyl alcohol, isobutyl alcohol, pentyl alcohol, cyclopentyl alcohol, crotyl alcohol, hexyl alcohol, cyclohexyl alcohol, allyl alcohol, benzyl alcohol, glycerol, and the like. The epoxides include ethylene oxide, propylene oxide, butylene oxide, isobutylene oxide, cyclopentene oxide, cyclohexene oxide, styrene oxide, and the like. The aldehydes include formaldehyde; acetaldehyde; propionaldehyde; n-butyraldehyde; n-valeraldehyde; caproaldehyde; acrolein; tran-2-cis-6-nonadienal; n-heptylaldehyde; trans-2-hexenal; hexadeconal; benzaldehyde; phenylacetaldehyde; o-tolualdehyde; m-tolualdehyde; p-tolualdehyde; salicylaldehyde; p-hydroxybenzaldehyde; and the like. The ketones include acetone, methyl ethyl ketone, 2-pentanone, 3-pentanone, 2-hexanone, 3-hexanone, cyclohexanone, methyl isobutyl ketone, acetophenone, propiophenone, n-butyrophenone, benzophenone, and the like. The carboxylic acids include formic acid, acetic acid, propionic acid, butyric acid, isobutyric acid, valeric acid, caproic acid, caprylic acid, capric acid, acrylic acid, methacrylic acid, benzoic acid, toluic acid, phthalic acid, salicylic acid, and the like. The carboxylic acid anhydrides include acetic anhydride, maleic anhydride, phthalic anhydride, benzoic anhydride, and the like. The carboxylic acids and anhydrides include hydrocarbon substituted carboxylic acids and anhydrides (e.g., hydrocarbon substituted succinic acids and anhydrides) wherein the hydrocarbon substituent contains from 1 to about 500 carbon atoms, and in one embodiment about 20 to about 500 carbon atoms. The esters include methyl acetate, vinyl acetate, ethyl acetate, n-propyl acetate, n-butyl acetate, n-pentyl acetate, isopentyl acetate, benzyl acetate, phenyl acetate, and the like.

The hydrocracking reactions may involve destructive hydrogenation (also known as hydrogenolysis) of large hydrocarbon molecules wherein the large or heavy hydrocarbon molecules are broken down to smaller or lighter ones and reacted with hydrogen. The hydrocarbon reactant may be referred to as the first reactant and the hydrogen may be referred to as the second reactant. The terms "light" and "heavy" are used herein in their normal sense within the refining industry to refer respectively to relatively low and high boiling point ranges. The hydrocarbon reactant may comprise any hydrocarbon requiring hydrocracking. The hydrocarbon reactant may vary from naptha to heavy crude oil residual fractions. The hydrocarbon reactant may have a 5% by volume boiling point above about 350° F. (177° C.), and in one embodiment above about 400° F. (204° C.). In one embodiment, at least about 90% by volume of the hydrocarbon reactant may fall within the boiling point range of about 300° F. (149° C.) to about 1050° F. (566° C.), and in one embodiment between about 600° F. (316° C.) to about 1000° F. (538° C.). The hydrocarbon reactant may comprise one or more petroleum fractions such as atmospheric and vacuum gas oils (AGO and VGO).

The hydrocarbon reactant may comprise heavy hydrocarbonaceous mineral or synthetic oils or a mixture of one or more fractions thereof. The hydrocarbon reactant may comprise one or more straight run gas oils, vacuum gas oils, demetallized oils, deasphalted vacuum residues, coker distillates, cat cracker distillates, shale oils, tar sand oils, coal liquids, or a mixture of two or more thereof.

The hydrogen used in the hydrocracking reactions may be in the form of hydrogen gas or it may be in a hydrogen feed stream that further comprises water, methane, carbon dioxide, carbon monoxide and/or nitrogen. The hydrogen may be taken from a process stream of another process such as a steam reforming process (product stream with $H_2$/CO mole ratio of about 3), a partial oxidation process (product stream with $H_2$/CO mole ration of about 2), an autothermal reforming process (product stream with $H_2$/CO mole ratio of about 2.5), a $CO_2$ reforming process (product stream with $H_2$/CO mole ratio of about 1), a coal gassification process (product stream with $H_2$/CO mole ratio of about 1), and combinations thereof. With each of these hydrogen sources, the hydrogen may be separated from the remaining ingredients using conventional techniques such as membrane separation or adsorption.

The mole ratio of hydrocarbon reactant to hydrogen in these hydrocracking reactions may be in the range from about 0.1:1 to about 10:1, and in one embodiment about 0.5:1 to about 5:1.

The hydrocracking catalyst may be any hydrocracking catalyst. These include zeolite catalysts including beta zeolite, omega zeolite, L-zeolite, ZSM-5 zeolites and Y-type zeolites. The catalyst may include a refractory inorganic oxide such as alumina, magnesia, silica, tilania, zirconia and silica-alumina. The catalyst may comprise a hydrogenation component. Examples of suitable hydrogenation components include metals of Group IVB and Group VIII of the Periodic Table and compounds of such metals. Molybdenum, tungsten, chromium, iron, cobalt, nickel, platinum, palladium, iridium, osmium, rhoduim and ruthenium may be used as the hydrogenation component. These catalysts are described in U.S. Pat. No. 6,312,586 B1, which is incorporated herein by reference. The form in which these catalysts may be in is discussed in greater detail below.

The product made by the hydrocracking process may be a middle distillate fraction boiling in the range from about 260 to about 700° F. (127-371° C.). The term "middle distillate" is intended to include the diesel, jet fuel and kerosene boiling range fractions. The terms "kerosene" and "jet fuel" boiling range are intended to refer to a temperature range of 260-550° F. (127-288° C.) and "diesel" boiling range is intended to refer to hydrocarbon boiling points from about 260 to about 700° F. (127-371° C.). The distillate product may be a gasoline or naphtha fraction. These may be considered to be the $C_5$ to 400° F. (204° C.) endpoint fractions.

The hydrogenation reactions may involve the reaction, in the presence of one or more hydrogenation catalysts, of one or more hydrocarbon compounds that are capable of undergoing a hydrogenation reaction with hydrogen. The hydrocarbon compounds may be referred to as the first reactant. These hydrocarbon compounds may be in the form of liquids, or they may be in the form of gases dispersed in liquids. The liquid may comprise the reactant and one or more additional solvents. The solvents may be solvents for one or more reactants and/or products. The hydrogen may be referred to as the second reactant, and may be in the form of a gas. The hydrogen may be derived from any of the above mentioned sources.

The hydrocarbon compounds that may undergo a hydrogenation reaction include the unsaturated hydrocarbon compounds discussed above. The hydrocarbon compounds include unsaturated fats and oils. The fats and oils may be derived from animal or vegetable sources. The fats and oils include triglycerides, that is, esters of glycerol and fatty acids. The fatty acids may be monounsaturated or polyunsaturated. Examples of the fatty acids in the fats and oils include oleic acid, linoleic acid, linolenic acid, and the like.

The mole ratio of unsaturated hydrocarbon reactant to hydrogen in these hydrogenation reactions may be in the range from about 0.1:1 to about 10:1, and in one embodiment about 0.5:1 to about 5:1.

The hydrogenation catalyst may be hydrogenation any catalyst. These include metals of Group IVB and Group VIII of the Periodic Table and compounds of such metals. Molybdenum, tungsten, chromium, iron, cobalt, nickel, platinum, palladium, iridium, osmium, rhodium, rhenium, and ruthenium may be used. In one embodiment, the catalyst may comprise palladium coated on the walls of the process microchannel or adhered to a fixed support within the process microchannel. The form in which these catalysts may be in is discussed in greater detail below.

The product made by the hydrogenation process may be a saturated or partially saturated hydrocarbon corresponding to the unsaturated hydrocarbon compounds used as the first reactant.

The process may be used to hydrogenate vegetable oils to increase their degree of saturation to produce edible fat products such as margarines. The improved mass transfer resulting from the inventive process may also improve the selectivity of the process to reduce the amount of unwanted conversion of cis isomers of triglycerides to trans isomers. This invention may improve the formation of the trans isomer from about 30% to about 50% by weight which may be obtained using conventional technology (i.e., non-microchannel process technology) to less than about 15% by weight, and in one embodiment less than about 10% by weight, and in one embodiment less than about 8% by weight. The process may use a hydrogenation catalyst. The catalyst may be in the form of a slurry, particulate solids or a fixed bed.

In one embodiment, the hydrogenation process may involve use of a catalyst (for example a precious metal such as palladium) fixed on the interior walls of the process microchannels or on a support structure positioned within the process microchannels. This may eliminate the need for a filtration step. This may also result in safer (no catalyst contamination), higher purity products. Precious metals catalysts such as palladium may be more reactive than prior art nickel catalysts and as such may effect the hydrogenation reactions at lower temperatures than conventionally used. This combined with the improved heat transfer resulting from the inventive process may significantly reduce the formation of secondary products that typically form as a result of thermal decomposition of oils and fats. This also may improve the quality of the food product. Unlike conventional nickel catalysts, the use of a palladium catalyst at reduced hydrogenation temperatures may decrease the concentration of hazardous trans-isomers, especially using high conversions which may be achieved at relatively short contact times pursuant to the inventive process. Improved mass transfer resulting from the inventive process may also improve the selectivity of the process. Improved heat and mass transfer may improve catalyst stability and turn-over frequency. This may result in a lower catalyst requirement. This may be beneficial when using precious metals because of the low operating temperature and pressure. In one embodiment, the catalyst may comprise nano-scale size particles of a precious metal such as palladium dispersed on the walls of the process microchannels and/or surface features or on a catalytic support such as a fin assembly insert using a dispersing/binding agent such as a colloidal metal oxide, carbon black, furfural alcohol, etc. The catalyst may be made using micro-shapes coated with catalytic metals that fill the void space of the microchannels.

The hydration reactions may involve the reaction, in the presence of a hydration catalyst, of an unsaturated hydrocarbon compound with water to form an alcohol or an ether. The unsaturated hydrocarbon compound, which may be referred to as the first reactant, may be any of the unsaturated hydrocarbon compounds discussed above. The water, which may be referred to as the second reactant, may be taken from any convenient source. The water may be deionized or purified using osmosis or distillation. The mole ratio of unsaturated hydrocarbon to water may be in the range from about 0.1 to about 10, and in one embodiment about 0.5 to about 5.

The hydration catalyst may comprise a solid acid catalyst such as zeolite; an acidic ion exchange resin containing sulfonate groups or the like; an inorganic oxide such as hydrated niobium oxide, hydrated tantalum oxide, zirconium dioxide, titanium dioxide, aluminum oxide, silicon dioxide, or a mixed oxide thereof; or an ion exchange type layered compound obtained by treating a layered compound such as smectite, kaolinite or vermiculite with at least one metal oxide selected from oxides of aluminum, silicon, titanium and zirconium. The catalyst may comprise aluminosilicates such as mordenite, faujasite, clinoptilite, L type zeolite, chabazite, erionite and ferrierite, as well as zeolite products ZSM-5, ZSM-4, ZSM-8, ZSM-11, ZSM-12, ZSM-20, ZSM-40, ZSM-35 and ZSM-48. The catalyst may comprise an element-containing zeolite such as borosilicate, gallosilicate and ferroaluminosilicate. These zeolites may contain thorium, copper, silver, chromium, molybdenum, tungsten, titanium, zirconium, hafnium and like metals. A proton exchange type (H type) zeolite may be used, and a portion thereof may be exchanged with a cationic species selected from alkali elements such as Na, K and Li, alkaline earth elements such as Mg, Ca and Sr and Group VIII elements such as Fe, Co, Ni, Ru or Pd. The form in which the catalyst may be in is discussed in greater detail below.

The carbonylation reactions may involve the reaction of a saturated or unsaturated hydrocarbon with carbon monoxide in the presence of a carbonylation catalyst. The saturated or unsaturated hydrocarbon reactant, which may be referred to as the first reactant, may be any of the saturated or unsaturated hydrocarbons discussed above. The carbon monoxide, which may be referred to as the second reactant, may be taken from any source. The carbon monoxide may be taken from a process stream such as a steam reforming process (product stream with $H_2$/CO mole ratio of about 3), a partial oxidation process (product stream with $H_2$/CO mole ratio of about 2), an autothermal reforming process (product stream with $H_2$/CO mole ratio of about 2.5), a $CO_2$ reforming process (product stream with $H_2$/CO mole ratio of about 1), a coal gassification process (product stream with $H_2$/CO mole ratio of about 1), and combinations thereof. With each of these carbon monoxide sources, the carbon monoxide may be separated from the remaining ingredients using conventional techniques such as membranes or adsorption.

The mole ratio of hydrocarbon reactant to carbon monoxide in these carbonylation reactions may be in the range from about 0.5:1 to about 20:1, and in one embodiment about 2:1 to about 10:1.

The carbonylation catalyst may be any carbonylation catalyst. These include solid acid catalysts. The catalyst may be a solid comprising interacting protic and Lewis acid sites. The catalyst may comprise a combination of a Bronsted (protonic) acid and a Lewis acid. Examples include sulfated metal oxides (e.g., sulfated zirconia), fluorocarbon sulfonates $(B(CF_2)_nBSO_3H)$ in combination with supports (e.g., metal oxides and carbon), heteropolyacids, halides of Ta, Sb, Ga and B, halogenated metal oxides, sulfated zeolites, halides of Ta, Sb, Ga and B in combination with fluorosulfonic acid resins. The metal oxides include both single component oxides and multi-component oxides, i.e., mixed metal oxides. Single component metal oxides include aluminas, silicas, zirconia, titania and mixtures thereof. The mixed metal oxides can be either physical mixtures or structurally connected. Example of mixed metal oxides include ZrCTi, WCZr, TiCCu, TiCZn, TiCSi, AlCZr, FeCZr and TiCMn oxides. Examples include sulfated zirconia, sulfated titania, sulfated tungsten oxide, $BF_3$ on fluorinated alumina, aluminum chloride on chlorinated alumina, $H_3PW_{10}O_{40}$, $CS_{2.5}H_{0.5}PW_{12}O_{40}$, $H_4SiW_{12}O_{40}$, and the like. The form in which the catalyst may be in is discussed in greater detail below.

The sulfonation reactions may involve the substitution of —$SO_3H$ groups (from sulfuric acid) for hydrogen atoms, for example, conversion of benzene, $C_6H_6$, into benzenesulfonic acid, $C_6H_5SO_3H$. The sulfonation procedures that may be used include the reaction of aromatic hydrocarbons with sulfuric acid, sulfur trioxide, or chlorosulfuric acid; the reaction of organic halogen compounds with inorganic sulfites; and the oxidation of certain classes of organic sulfur compounds, for example, thiols or disulfides.

Concentrated sulfuric acid, fuming sulfuric acid, chlorosulfonic acid, sulfuric anhydride, adducts of dioxane with $SO_3$, adducts of amine with $SO_3$, etc. may be used as agents for sulfonating aromatic compounds by introducing a sulfonic acid group into the aromatic ring of the compound. Aromatic amine compounds may be sulfonated by preparing an acidic sulfate of amine from the aromatic amine compound and a stoichiometric amount of sulfuric acid and heated to obtain an aminesulfonic acid.

The sulfation reactions may involve methods by which esters or salts of sulfuric acid (sulfates) are formed. The esters may be prepared by treating an alcohol with sulfuric acid, sulfur trioxide, chlorosulfuric acid, or sulfamic acid. The sulfating agents may include concentrated sulfuric acid, oleum, sulfur trioxide, chlorosulfonic acid, or sulfamic acid.

Figure 2:
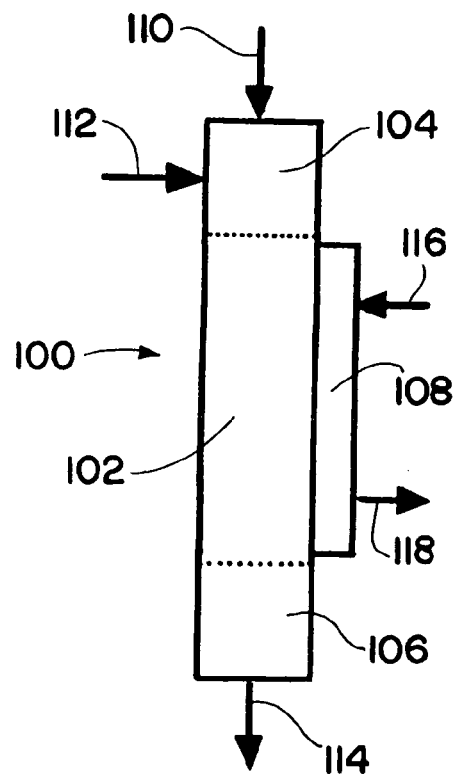
FIG. 2 is a schematic illustration of the inventive process in a particular form wherein a first reactant and a second reactant flow into a microchannel reactor, contact each other and a catalyst, and react to form a desired product.

In one embodiment, the inventive process may be conducted in a microchannel reactor as illustrated, for example, in FIGS. 2-11. Referring to FIG. 2, the process may be conducted using microchannel reactor 100, which includes microchannel reactor core 102, feed stream header 104, product footer 106, and heat exchange manifold 108. The reactor core 102 may contain one or more repeating units, each of the repeating units containing one or more process microchannels. The feed stream header 104 may be used for distributing the first reactant to the process microchannels and the second reactant to the second reactant stream channels or, alternatively, it may be used for forming the multiphase reaction mixture and distributing the multiphase reaction mixture to the process microchannels. The formation of the multiphase reaction mixture may occur in both the feed stream header 104 and the process microchannels.

In one embodiment, the feed stream header may comprise a first reactant zone, at least one second reactant zone and an apertured section positioned between the first reactant zone and the second reactant zone. The second reactant may flow from the second reactant zone through the apertured section into the first reactant zone where it contacts the first reactant and forms the multiphase reaction mixture. The multiphase reaction mixture may flow from the first reactant zone into the process microchannels where it contacts the catalyst and reacts to form the product.

In one embodiment, each process microchannel may have at least one apertured section and at least one adjacent second reactant stream channel. The apertured section may be positioned in one or more sidewalls of the process microchannel. The apertured section may extend along at least part of the axial length of the process microchannel. The second reactant may flow in the second reactant stream channel and from there to and through the apertured section into the process microchannels where it contacts the first reactant and forms the multiphase reaction mixture. The multiphase reaction mixture may contact the catalyst in the process microchannels and react to form the product.

The process microchannels may contain one or more reaction zones wherein the reactants react to form the desired product. In one embodiment, a catalyst in solid form may be present in one or more of these reaction zones. In one embodiment, a catalyst in liquid form may flow into the reaction zone with one or more of the reactants and/or it may flow into the reaction zone as a separate feed stream.

In the process microchannels the first and second reactants may react with each other in the presence of one or more catalysts to form the desired product. The product may flow from the process microchannels into and through product footer 106, and from product footer 106 out of the reactor, as indicated by arrow 114. This product footer 106 may be used to collect the product from the process microchannels. Although an advantage of the inventive process is that a high level of conversion to the desired product may be obtained with one pass through the microchannel reactor, in one embodiment, one or more unreacted reactants may be separated from the product using conventional or microchannel techniques and recycled back through the microchannel reactor. The unreacted reactants may be recycled through the microchannel reactor any number of times, for example, one, two, three, four or more times, etc.

The reaction process may be exothermic or endothermic. In order to control the reaction, heat may be transferred between the process microchannels and/or second reactant stream channels, and a heat source and/or heat sink. That is, during the inventive process the process microchannels and/or second reactant stream channels may be heated using a heat source and/or cooled using a heat sink. The heat source and/or heat sink may be adjacent to the process microchannels and/or second reactant stream channels. Alternatively, the heat source and/or heat sink may be remote from, that is not adjacent to, the process microchannels and/or second reactant stream channels, but sufficiently close to the process microchannels and/or second reactant stream channels to transfer heat between the heat source and/or heat sink and the process microchannels and/or second reactant stream channels.

The heat source and/or heat sink may comprise one or more heat exchange channels containing a heat exchange fluid. The heat source may comprise a non-fluid heating element such as an electric heating element or a resistance heater. The heat sink may comprise a non-fluid cooling element. In one embodiment, a heat exchange fluid flows into heat exchange manifold 108, as indicated by arrow 116, and from heat exchange manifold 108 through heat exchange channels in the reactor core 102 and back to heat exchange manifold 108, and out of heat exchange manifold 108, as indicated by arrow 118. Heat transfer between the reactants and product may be effected using convective heat transfer. In one embodiment, heat transfer may be enhanced using a heat exchange fluid wherein the heat exchange fluid undergoes an exothermic or endothermic reaction and/or a full or partial phase change. Multiple heat exchange zones may be employed along the length of the process microchannels and/or second reactant stream channels to provide for different temperatures at different locations along the lengths of the process microchannels and/or second reactant stream channels. In one embodiment, a heat exchange channel may exchange heat with two or more process microchannels, for example, three, four, five, six process microchannels, etc.

The microchannel reactor 100 may be used in combination with one or more storage vessels, pumps, valves, manifolds, microprocessors, flow control devices, and the like, which are not shown in the drawings, but would be apparent to those skilled in the art. Repeating units that may be used in the reactor core 102 are illustrated in FIGS. 3-11.

Figure 3:
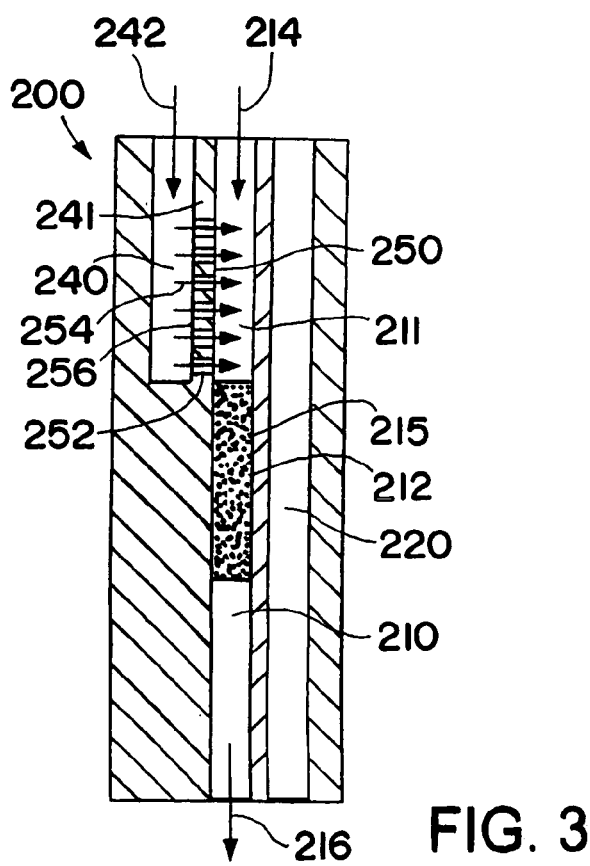
FIG. 3 is a schematic illustration of a repeating unit comprising a process microchannel, an apertured section, a second reactant stream channel, and a heat exchange channel that may be used in the microchannel reactor illustrated in FIG. 2.

FIG. 3 illustrates repeating unit 200 which may be used in the reactor core 102. Repeating unit 200 comprises process microchannel 210, heat exchange channel 220, second reactant stream channel 240, and apertured section 250. A common wall 241 separates process microchannel 210 and second reactant stream channel 240. The apertured section 250, which contains apertures 252 formed in sheet or plate 256, is positioned in common wall 241. The process microchannel 210 has a mixing zone 211, and a reaction zone 212. A catalyst 215 is positioned in the reaction zone 212. The mixing zone 211 is upstream from the reaction zone 212. The first reactant flows through the feed stream header 104 and from there into process microchannel 210, as indicated by the arrow 214, and into the mixing zone 211. The second reactant flows through the feed stream header 104 and from there into second reactant stream channel 240, as indicated by arrow 242, and from the second reactant stream channel 240 through apertures 252 into mixing zone 211, as indicated by arrows 254. The direction of flow of the second reactant in the second reactant stream channel 240, as indicated by arrow 242, is cocurrent with the direction of flow of the first reactant in the process microchannel 210, as indicated by arrow 214; alternatively, the flow of the second reactant in the second reactant stream channel 240 may be counter-current or cross-current relative to the flow of the first reactant in the process microchannel 210. The first reactant and the second reactant contact each other in the mixing zone 211 and form a reactant mixture. The reactant mixture flows from the mixing zone 211 into the reaction zone 212, contacts the catalyst 215, and reacts to form the desired product. The product exits the process microchannel 210, as indicated by arrow 216. The product exiting the process microchannel 210 flows through the product footer 106 and out of the microchannel reactor 100, as indicated by arrow 114. Heat exchange fluid flows from heat exchange manifold 108 through heat exchange channel 220 and then back to heat exchange manifold 108. The flow of heat exchange fluid through the heat exchange channel 220 may be co-current or counter-current to the flow of fluid flowing through process microchannel 210. Alternatively, the heat exchange channel 220 could be oriented to provide for the flow of the heat exchange fluid in a direction that is cross-current to the flow of fluid through the process microchannel 210.

In an alternate embodiment of the repeating unit 200 illustrated in FIG. 3, a supplemental mixing zone may be provided in the process microchannel 210 between the mixing zone 211 and reaction zone 212. The residence time for mixing in the supplemental mixing zone may be defined using the sum of the total of the flow through the apertured section 250 and the flow of the first reactant feed stream in process microchannel 210, at standard conditions of temperature (i.e., 0° C.) and pressure (i.e., atmospheric pressure), and the volume defined by the process microchannel 210 between the end of the mixing zone 211 and the beginning of the reaction zone 212. This residence time for mixing in the supplemental mixing zone may be in the range up to about 5000 milliseconds (ms), and in one embodiment from about 0.25 ms to about 1000 ms, and in one embodiment from about 0.25 ms to about 500 ms, and in one embodiment from about 0.25 to about 250 ms, and in one embodiment from about 0.25 to about 100 ms, and in one embodiment from about 0.25 to about 50 ms, and in one embodiment from about 0.25 to about 25 ms, and in one embodiment from about 0.25 to about 10 ms, and in one embodiment from about 0.25 to about 2.5 ms.

Figure 4:
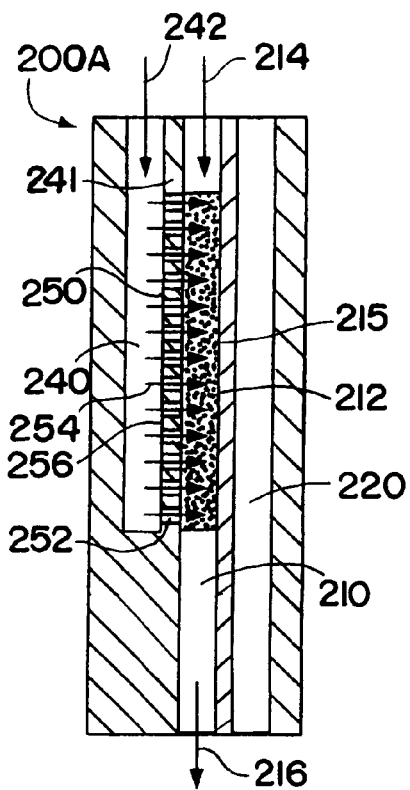
FIG. 4 is a schematic illustration of an alternate embodiment of a repeating unit comprising a process microchannel, an apertured section, a second reactant stream channel, and a heat exchange channel that may be used in the microchannel reactor illustrated in FIG. 2.

The repeating unit 200A illustrated in FIG. 4 is identical to the repeating unit 200 illustrated in FIG. 3 with the exception that the repeating unit 200A does not contain the separate mixing zone 211. With repeating unit 200A, the second reactant flows through the apertured section 250 into the reaction zone 212 where it contacts the first reactant and reacts to form the desired product. The product then flows out of the process microchannel 210, as indicated by arrow 216.

Figure 5:
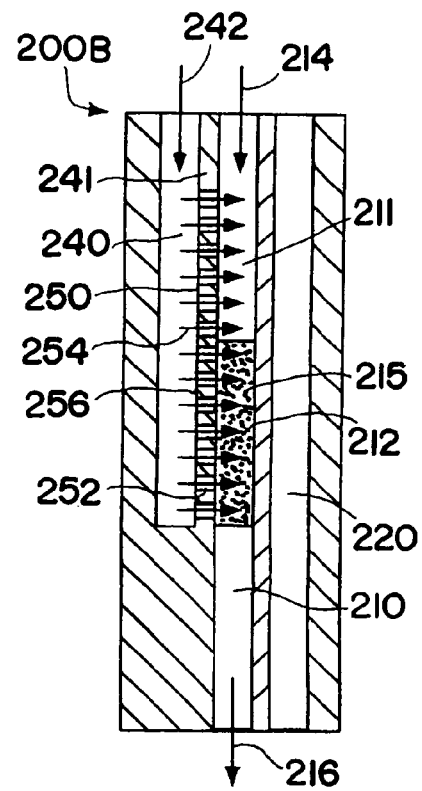
FIG. 5 is a schematic illustration of another alternate embodiment of a repeating unit comprising a process microchannel, an apertured section, a second reactant stream channel, and heat exchange channel that may be used in the microchannel reactor illustrated in FIG. 2.

The repeating unit 200B illustrated in FIG. 5 is identical to the repeating unit 200 illustrated in FIG. 3 with the exception that part of the second reactant mixes with the first reactant in the mixing zone 211, and the remainder of the second reactant mixes with the first reactant in the reaction zone 212. The amount of the second reactant that mixes with the first reactant in the mixing zone 211 may be from about 1% to about 99% by volume of the second reactant, and in one embodiment from about 5% to about 95% by volume, and in one embodiment from about 10% to about 90% by volume, and in one embodiment from about 20% to about 80% by volume, and in one embodiment from about 30% to about 70% by volume, and in one embodiment from about 40% to about 60% by volume of the second reactant. The remainder of the second reactant mixes with the first reactant in the reaction zone 212.

Figure 6:
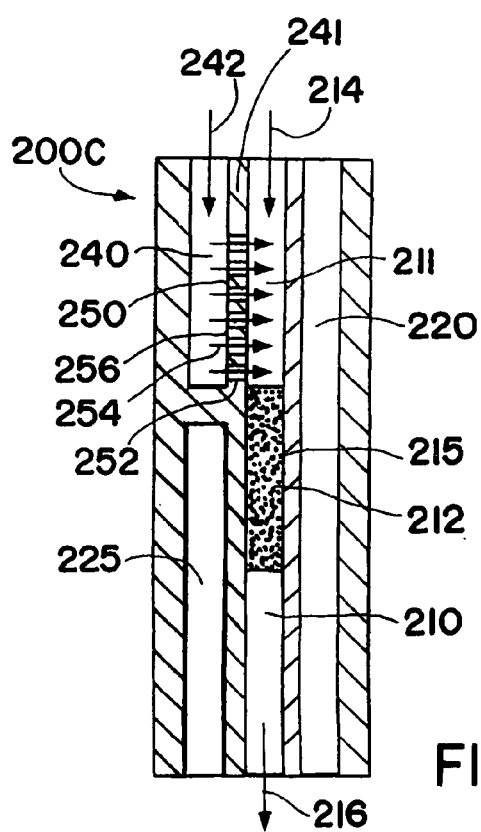
FIG. 6 is a schematic illustration of another alternate embodiment of a repeating unit comprising a process microchannel, an apertured section, a second reactant stream channel, a heat exchange channel, and another heat exchange channel that may be used in the microchannel reactor illustrated in FIG. 2.

The repeating unit 200C illustrated in FIG. 6 is identical to the repeating unit 200 illustrated in FIG. 4 with the exception that the repeating unit 200C includes heat exchange channel 225. The flow of heat exchange fluid through the heat exchange channel 225 may be co-current or countercurrent to the flow of fluid through the process microchannel 210. Alternatively, the heat exchange channel 225 could be oriented to provide for the flow of heat exchange fluid in a direction that would be cross-current to the flow of fluid through the process microchannel 210.

Figure 7:
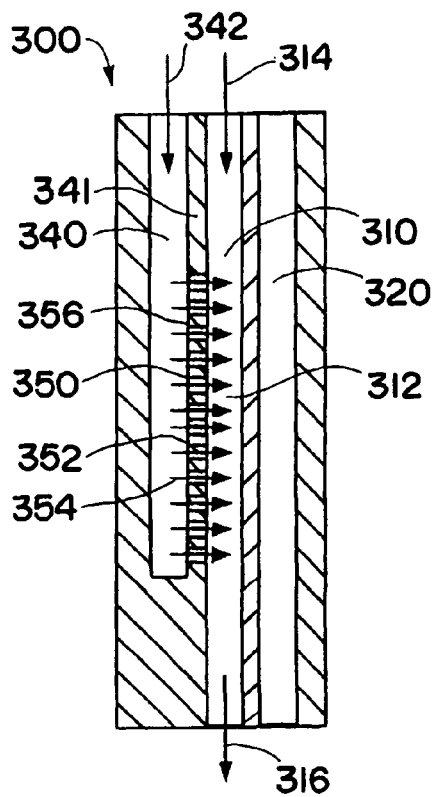
FIG. 7 is a schematic illustration of another alternate embodiment of a repeating unit comprising a process microchannel, an apertured section, a second reactant stream channel, and a heat exchange channel that may be used in the microchannel reactor illustrated in FIG. 2.

The repeating unit 300 illustrated in FIG. 7 is suitable for conducting the inventive process using a liquid catalyst. Repeating unit 300 comprises microchannel 310, heat exchange channel 320, second reactant stream channel 340 and apertured section 350. A common wall 341 separates process microchannel 310 and second reactant stream channel 340. The apertured section 350, which contains apertures 352 formed in sheet or plate 356, is positioned in common wall 341. The process microchannel 310 includes reaction zone 312, which is adjacent to apertured section 350. The reaction zone 312 may extend over the entire length of the process microchannel 310, or its length may be less than the length of the process microchannel 310. In operation, the first reactant flows through the feed stream header 104 and from there into process microchannel 310, as indicated by the arrow 314, and into the reaction zone 312. The second reactant flows through the feed stream header 104 and from there into second reactant stream channel 340, as indicated by arrow 342, and from the second reactant stream channel 340 through apertures 352 into reaction zone 312, as indicated by arrows 354. The liquid catalyst may be premixed with the first reactant and/or the second reactant. The direction of flow of the second reactant in the second reactant stream channel 340, as indicated by arrow 342, is cocurrent with the direction of flow of the first reactant in the process microchannel 310, as indicated by arrow 314; alternatively, the flow of the second reactant in the second reactant stream channel 340 may be counter-current or cross-current relative to the flow of the first reactant in the process microchannel 310. The first reactant and the second reactant contact each other and the catalyst in the reaction zone 312 and react to form the desired product. The product exits the process microchannel 310, as indicated by arrow 316. The product exiting the process microchannel 310 flows through the product footer 106 and out of the microchannel reactor 100, as indicated by arrow 114. Heat exchange fluid flows from heat exchange manifold 108 through heat exchange channel 320 and then back to heat exchange manifold 108. The flow of heat exchange fluid through the heat exchange channel 320 may be co-current or counter-current to the flow of fluid through the process microchannel 310. Alternatively, the heat exchange channel 320 could be oriented to provide for the flow of the heat exchange fluid in a direction that would be cross-current to the flow of fluid through the process microchannel 310.

Figure 8:
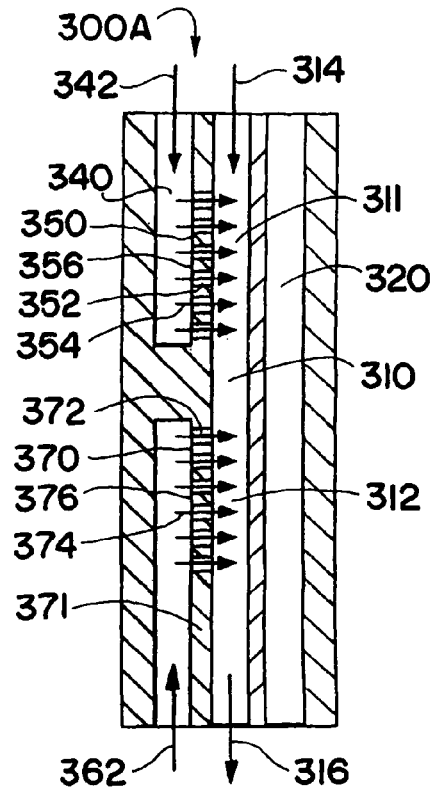
FIG. 8 is a schematic illustration of another alternate embodiment of a repeating unit comprising a process microchannel, an apertured section, a second reactant stream channel, another apertured section, a staged addition liquid catalyst channel and a heat exchange channel that may be used in the microchannel reactor illustrated in FIG. 2.

The repeating unit 300B illustrated in FIG. 8 is similar to the repeating unit 300 illustrated in FIG. 7 with the exception that the repeating unit 300A further comprises staged addition liquid catalyst channel 360 and apertured section 370. A common wall 371 separates process microchannel 310 and staged addition liquid catalyst channel 360. The apertured section 370, which contains apertures 372 formed in sheet or plate 376, is positioned in common wall 371. The process microchannel 310 has a mixing zone 311 adjacent to apertured section 350, and a reaction zone 312 adjacent to apertured section 370. The mixing zone 311 is upstream from the reaction zone 312. The first reactant flows through the feed stream header 104 and from there into the process microchannel 310, as indicated by arrow 314, and into the mixing zone 311. The second reactant flows through the feed stream header 104 and from there into second reactant stream channel 340, as indicated by arrow 342, and from the second reactant stream channel 340 through apertures 352 into mixing zone 311, as indicated by arrows 354. The direction of the flow of the second reactant in the second reactant stream channel 340, as indicated by arrow 342, is cocurrent with the direction of the flow of the first reactant in the process microchannel 310, as indicated by arrow 314; alternatively, the flow of the second reactant in the second reactant stream channel 340 may be counter-current or cross-current relative to the flow of the first reactant in the process microchannel 310. The first reactant and the second reactant contact each other in the mixing zone 311 and form a reactant mixture. The reactant mixture flows from the mixing zone 311 to the reaction zone 312. The liquid catalyst flows into the staged addition liquid catalyst channel 360, as indicated by arrow 362, and from the staged addition liquid catalyst channel 360 through apertures 372 into reaction zone 312, as indicated by arrows 374. The direction of flow of the liquid catalyst in the staged addition liquid catalyst channel 360, as indicated by arrow 362, is counter-current to the direction of flow of the first reactant in the process microchannel 310, as indicated by arrow 314; alternatively, the flow of the liquid catalyst in the staged addition liquid channel 360 may be co-current or cross-current relative to the flow of the first reactant in the process microchannel 310. The liquid catalyst contacts the reactant mixture in the reaction zone 312. The reactant mixture reacts to form the desired product. The product exits the process microchannel 310, as indicated by arrow 316. The product exiting the process microchannel 310 flows through the product footer 106 and out of the microchannel reactor 100, as indicated by arrow 114. Heat exchange fluid flows from the heat exchange manifold 108 through heat exchange channel 320 and then back to heat exchange manifold 108. The flow of heat exchange fluid through the heat exchange channel 320 may be co-current or counter-current to the flow of fluid flowing through the process microchannel 310. Alternatively, the heat exchange channel 320 could be oriented to provide for the flow of the heat exchange fluid in a direction that would be cross-current to the flow of fluid through the process microchannel 310.

Figure 9:
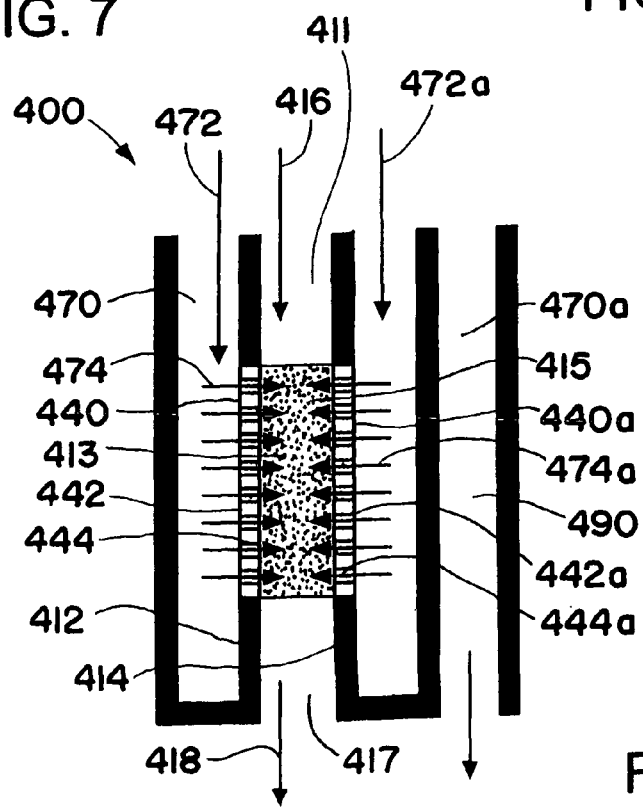
FIG. 9 is a schematic illustration of another alternate embodiment of a repeating unit comprising a process microchannel, two apertured sections, two second reactant stream channels, and a heat exchange channel that may be used in the microchannel reactor illustrated in FIG. 2.

The repeating unit 400 illustrated in FIG. 9 includes process microchannel 410, apertured sections 440 and 440a, second reactant stream channels 470 and 470a, and heat exchange channel 490. Apertured section 440 is formed in side wall 412, and apertured section 440a is formed in side wall 414. The apertured sections 440 and 440a may be referred to as porous sections or porous substrates. Second reactant stream channels 470 and 470a open to process microchannel 410 through apertured sections 440 and 440a, respectively. The apertured section 440 may comprise a sheet or plate 442 having an array of apertures 444 extending through it. Similarly, the apertured section 440a may comprise a sheet or plate 442a having an array of apertures 444a extending through it. The process microchannel 410 has a non-apertured or non-porous region 411 and a reaction zone 413. The non-apertured region 411 extends from the entrance to the process microchannel 410 to the entrance to the reaction zone 413. The non-apertured region 411 is upstream from the reaction zone 413. The reaction zone 413 is next to the apertured sections 440 and 440a. A catalyst 415 is positioned in the reaction zone 413. Non-apertured region 417 extends from the end of the reaction zone 413 to the end of the process microchannel 410. The non-apertured region 417 is downstream from the reaction zone 413. Adjacent to the second reactant stream channel 470a is heat exchange channel 490. In operation, a first reactant stream flows through the feed stream header 104 and from there into the process microchannel 410, as indicated by arrow 416, and then through the non-apertured region 411 into the reaction zone 413. A second reactant stream flows through the feed stream header 104 into second reactant stream channel 470, as indicated by arrow 472, and from there through apertured section 440, as indicated by arrows 474, into the reaction zone 413. Another second reactant stream flows through the feed stream header 104 into second reactant stream channel 470a, as indicated by arrow 472a, and from there through apertured section 440a, as indicated by arrows 474a, into the reaction zone 413. The second reactant stream flowing through channel 470 may have a composition and/or physical properties that are the same as the composition and/or physical properties of the another second reactant stream flowing through channel 470a. Alternatively, the composition and/or physical properties may be different. For example, the second reactant stream flowing through channel 470 may be in the form of a gas and the another second reactant stream flowing through channel 470a may be in the form of a liquid. One of the second reactants may comprise one reactant (for example, water vapor) and another of the second reactants may comprise another reactant (for example, carbon monoxide). In the reaction zone 413, the second reactant and the another second reactant contact the first reactant and the catalyst 415 and react to form the desired product. The product flows through non-apertured section 417 and out of the process microchannels 410, as indicated by arrow 418. The product exiting the process microchannel 410 flows through the product footer 106 and out of the microchannel reactor 100 as indicated by arrow 114. Heating or cooling may be employed. When heating or cooling is desired, heat exchange fluid flows from the heat exchange manifold 108 through the heat exchange channel 490, and then back to the heat exchange manifold 108. The heat exchange fluid heats or cools the fluids in the channels 410, 470 and 470a. The flow of the heat exchange fluid through the heat exchange channel 490 may co-current, counter-current, or cross-current relative to the flow of the first reactant in the process microchannel 410. The degree of heating or cooling may vary over the length of the channels. The heating or cooling may be negligible or non-existent in some sections of the process microchannel 410 and/or second reactant stream channels 470 and 470a, and moderate or relatively high in other sections.

Figure 10:
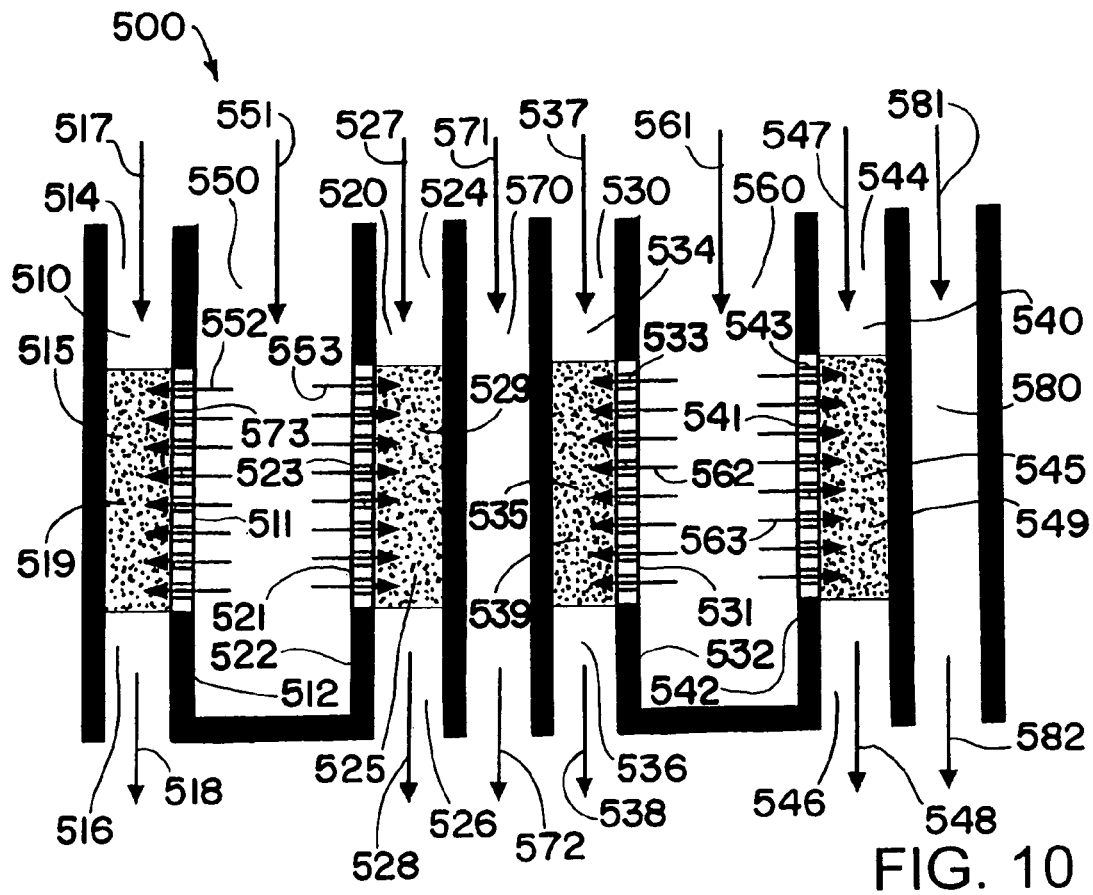
FIG. 10 is a schematic illustration of another alternate embodiment of a repeating unit comprising four process microchannels, four apertured sections, two second reactant stream channels, and two heat exchange channels that may be used in the microchannel reactor illustrated in FIG. 2.

In one embodiment, multiple reactant formulations and/or sets of processing conditions may be used to generate multiple products within a single microchannel reactor. For example, a single microchannel reactor may employ two or more process microchannels and associated second reactant stream channels and heat exchange channels to make two, three, four, five, six, seven, eight, nine, ten, tens, hundreds, thousands, tens of thousands, hundreds of thousands, etc. of different products within a single microchannel reactor. This type of reactor can be referred to as a combinatorial-synthesis device. This is shown in FIG. 10 wherein repeating unit 500 is illustrated. Repeating unit 500 employs four process microchannels and as a result may be capable of generating up to four distinct products. The repeating unit 500 can be repeated any desired number of times, for example, two, three, four, five, six, seven, eight, nine, ten, tens, hundreds, thousands, tens of thousands, etc., to provide for the possibility of the multiple products indicated above. Repeating unit 500 includes process microchannels 510, 520, 530 and 540, second reactant stream channels 550 and 560, and heat exchange channels 570 and 580. Apertured section 511 is formed in sidewall 512. Apertured section 521 is formed in sidewall 522. Apertured section 531 is formed in sidewall 532. Apertured section 541 is formed in sidewall 542. Apertures 513, 523, 533 and 543 are positioned in and extend through apertured sections 511, 521, 531 and 541, respectively. The process microchannels 510, 520, 530 and 540 include reaction zones 515, 525, 535 and 545, respectively. Catalysts 519, 529, 539 and 549 are positional in the reaction zones 515, 525, 535 and 545, respectively. Reaction zones 515, 525, 535 and 545 are positioned next to apertured sections 511, 521, 531 and 541, respectively. The process microchannels 510, 520, 530 and 540 include non-apertured sections 514, 524, 534 and 544 positioned upstream from the reaction zones 515, 525, 535 and 545, respectively. The process microchannels 510, 520, 530 and 540 also include non-apertured sections 516, 526, 536 and 546 which are positioned downstream of the reaction zones 515, 525, 535 and 545, respectively. In operation, first reactant streams flow through the feed stream header 104 and from there into process microchannels 510, 520, 530 and 540 as indicated by arrows 517, 527, 537 and 547, respectively. The first reactant streams entering process microchannels 510, 520, 530 and 540 may have compositions and/or properties that are the same as one another or compositions and/or properties that are different from one another. The first reactant streams flow into the non-apertured sections 514, 524, 534 and 544 and then into the reaction zones 515, 525, 535 and 545, respectively. Second reactant streams flow through feed stream header 104 and from there into the second reactant stream channels 550 and 560, as indicated by arrows 551 and 561. The second reactant stream entering second reactant stream channel 550 may have the same composition and/or properties as the second reactant stream entering the second reactant stream channel 560, or it may have a different composition and/or properties. The second reactant stream entering second reactant stream channel 550, as indicated by arrow 551, flows through the apertured sections 511 and 521, as indicated by arrows 552 and 553, into reaction zones 515 and 525, respectively. In the reaction zones 515 and 525, the second reactant contacts the first reactant and the catalyst and reacts to form a product. Similarly, a second reactant stream flows into second reactant stream channel 560, as indicated by arrow 561, and then flows through apertured sections 531 and 541, as indicated by arrows 562 and 563, into reaction zones 535 and 545, respectively. In the reaction zones 535 and 545 the second reactant contacts the first reactant and the catalyst and reacts to form a product. The products formed in reaction zones 515, 525, 535 and 545 may be the same or different. If different, the products may differ from one another with respect to composition and/or physical properties. The products flow from reaction zones 515, 525, 535 and 545 through non-apertured sections 516, 526, 536 and 546 out of the process microchannels 510, 520, 530 and 540, as indicated by arrows 518, 528, 538 and 548, respectively. The products exiting the process microchannels 510, 520, 530 and 540 flow through the product footer 106 and out of the microchannel reactor 100, as indicated by arrow 114. Heating or cooling using heat exchange channels 570 and 580 may be employed. When heating or cooling is employed, heat exchange fluid flows from the heat exchange manifold 108 through the heat exchange channels 570 and 580 and then back to the heat exchange manifold 108. The heat exchange fluid flows through heat exchange channels 570 and 580 in a direction that is co-current to the flow of the first reactant through the process microchannels 510, 520, 530 and 540, as indicated by arrows 571 and 572, and 581 and 582, respectively. Alternatively, the flow of heat exchange fluid through the heat exchange channels 570 and 580 may be countercurrent or cross-current relative to the flow of the first reactant in the process microchannels 510, 520, 530 and 540. The heat exchange fluid heats or cools the fluids in the channels 510, 520, 530, 540, 550 and 560. The degree of heating or cooling may vary over the length of each of the channels. The heating or cooling may be negligible or non-existent in some sections of the process channels and/or second reactant stream channels, and moderate or relatively high in other sections. An advantage of this embodiment of the invention is that it may provide for the forming and evaluating of multiple products at the same time using the same apparatus. This can be advantageous when it is desired to screen multiple formulations as potential new products.

Figure 11:
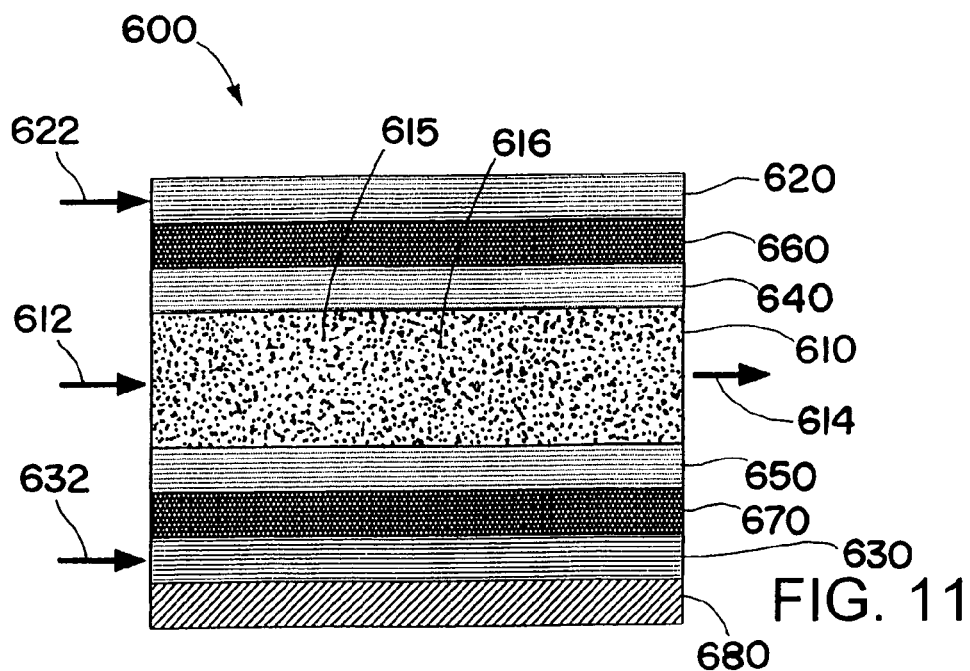
FIG. 11 is a schematic illustration of another alternate embodiment of a repeating unit comprising a process microchannel, two second reactant stream channels, four apertured sections, and a heat exchange channel that may be used in the microchannel reactor illustrated in FIG. 2.

The repeating unit 600 illustrated in FIG. 11 includes process microchannel 610, second reactant stream channels 620 and 630, apertured sections 640 and 650 which may be in the form of fine ceramic membranes, apertured sections 660 and 670, which may be in the form of macroporous supports, and heat exchange channel 680. A catalyst 616 is positioned in the reaction zone 615 of process microchannel 610. In operation, the first reactant flows through the feed stream header 104 and enters the process microchannel 610, as indicated by arrow 612. Second reactant streams flow through the feed stream header 104 and enter the second reactant stream channels 620 and 630, as indicated by arrows 622 and 632, respectively. One of the second reactant streams flows from the second reactant stream channel 620 through the apertured section 660 and then through the apertured section 640 into the process microchannel 610. Similarly, another second reactant stream flows through apertured section 670 and then through apertured section 650 into the process microchannel 610. The two second reactant streams may be the same or different in composition and/or properties. For example, one of the second reactant streams can be in the form of a gas and the other can be in the form of a liquid. The first reactant and the second reactant are mixed in the process microchannel 610, contact the catalyst 616, and react to form the desired product. The product exits the process microchannel 610, as indicated by arrow 614. The product exiting the process microchannel 610 flows through the product footer 106 and out of the microchannel reactor 100, as indicated by arrow 114. The reactant and product streams can be heated or cooled with a heat exchange fluid in the heat exchange channel 680. The heat exchange fluid flows from the heat exchange manifold 108 through the heat exchange 680 and then back to the heat exchange manifold 108. The flow of the heat exchange fluid through the heat exchange channel 680 may be co-current, counter-current or cross-current relative to the flow fo the first reactant in the process microchannel 610.

Figure 32:
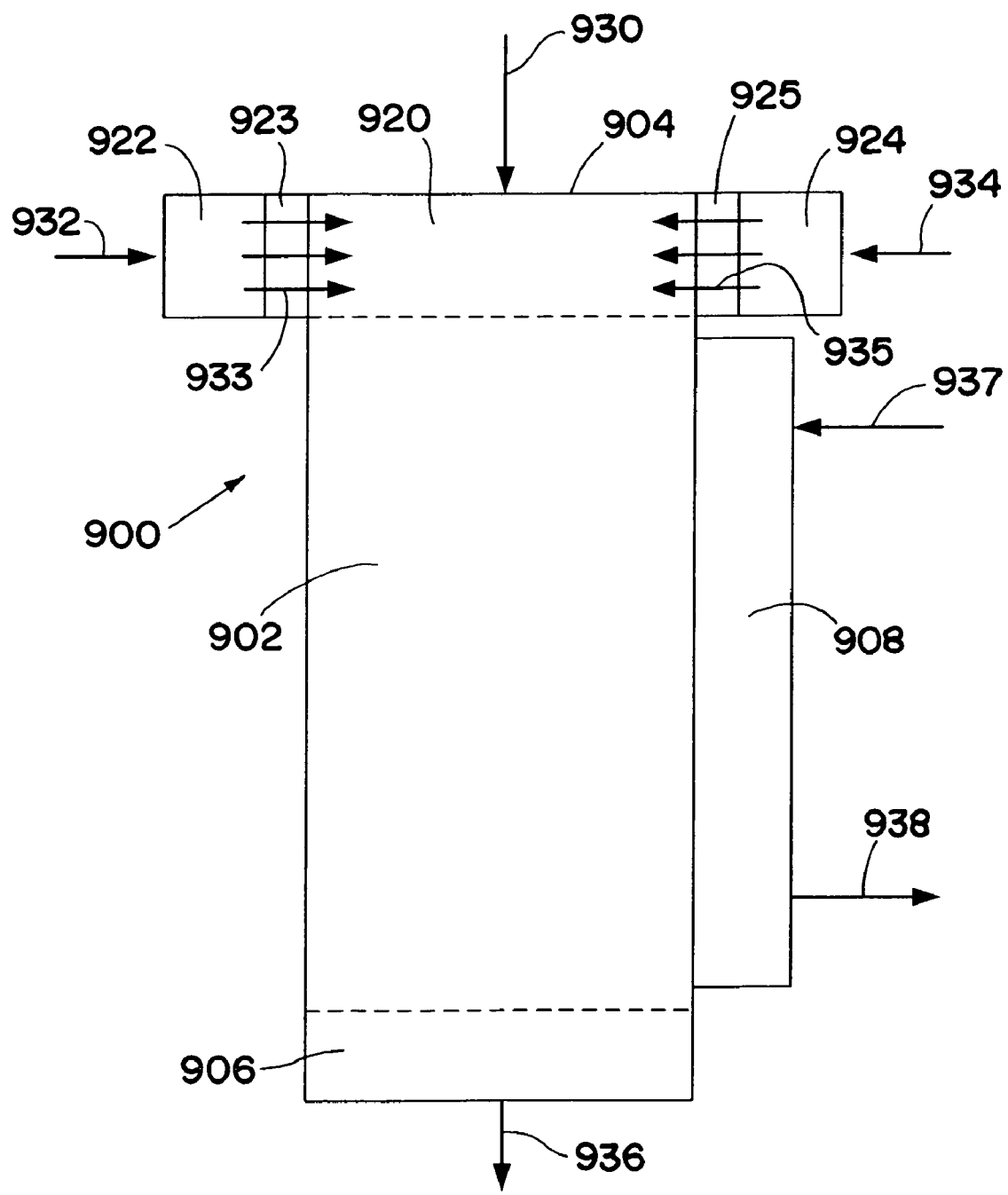
FIG. 32 is a schematic illustration of an alternate embodiment of the inventive process in a particular form wherein a first reactant and a second reactant flow into a microchannel reactor, contact each other in a feedstream header and form a multiphase reaction mixture, the multiphase reaction mixture then flows from the feed stream header through process microchannels in a microchannel reactor core in contact with a catalyst to form the desired product.
Figure 33:
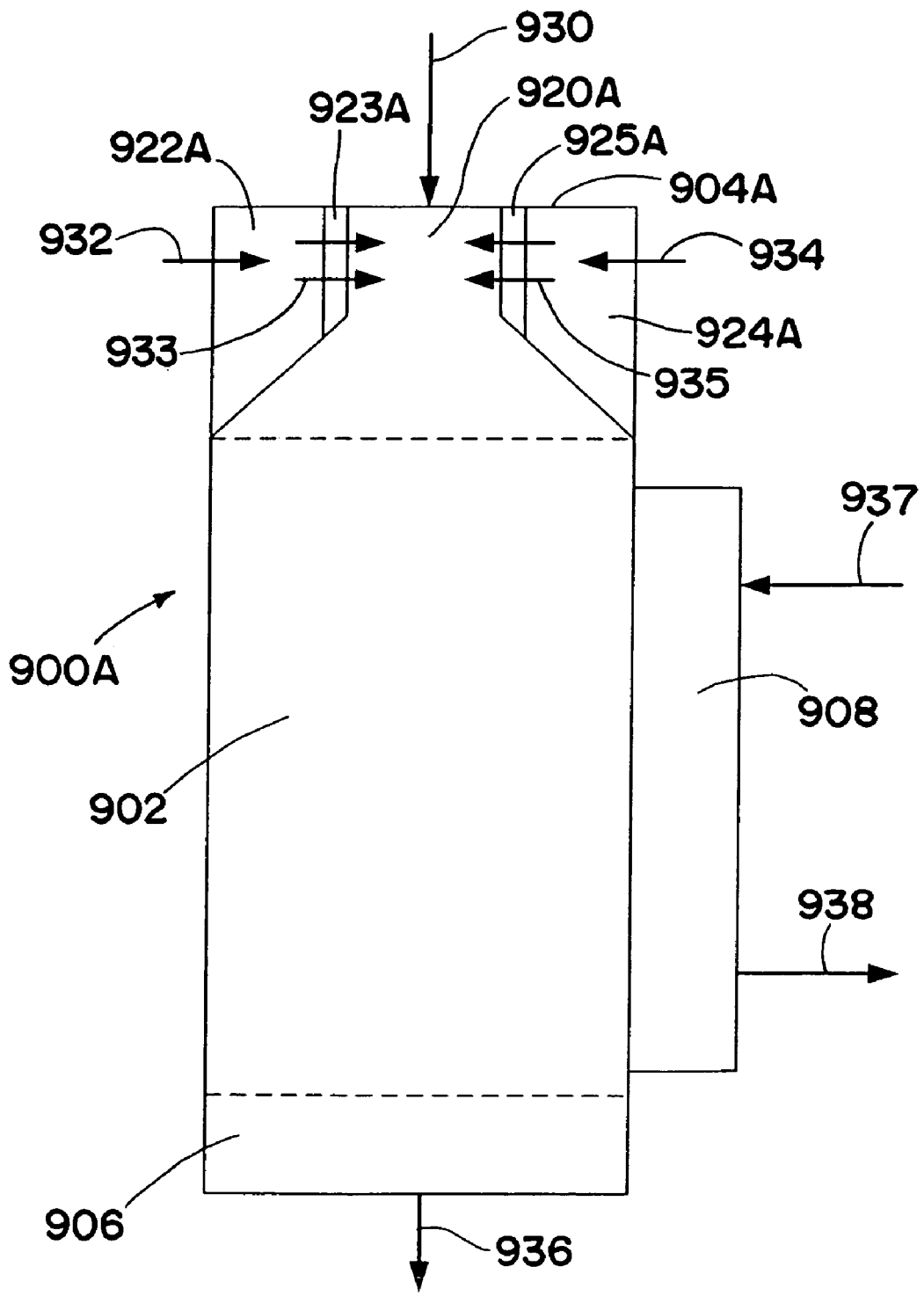
FIG. 33 is a schematic illustration of another alternate embodiment of the inventive process in a particular form wherein a first reactant and a second reactant flow into a microchannel reactor, contact each other in a feedstream header and form a multiphase reaction mixture, the multiphase reaction mixture then flows through process microchannels in a microchannel reactor core in contact with a catalyst to form the desired product.

In one embodiment, the inventive process may be conducted in a microchannel reactor as illustrated, for example, in FIGS. 32-36. Referring to FIG. 32, the process may be conducted using microchannel reactor 900, which includes microchannel reactor core 902, feed stream header 904, product footer 906 and heat exchange manifold 908. The microchannel reactor 900A illustrated in FIG. 33 is the same as the microchannel reactor 900 illustrated in FIG. 32 with the exception that the microchannel reactor 900A employs feed stream header 904A rather than feedstream header 904. Feedstream headers 904 and 904A are similar in design and operation. The design and operation of these headers is described in more detail below. The reactor core 902 in microchannel reactors 900 and 900A may contain one or more of the repeating units 910, 912 and/or 914 illustrated in FIGS. 34-36, respectively.

Feedstream header 904 includes first reactant zone 920, second reactant zones 922 and 924, and apertured sections 923 and 925. Apertured section 923 is positioned between first reactant zone 920 and second reactant zone 922. Apertured section 925 is positioned between first reactant zone 920 and second reactant zone 924. Feedstream header 904A is similarly constructed and includes first reactant zone 920A, second reactant zones 922A and 924A, and apertured sections 923A and 925A.

In operation, the first reactant flows into the first reactant zone 920 as indicated by arrow 930. The second reactant flows into second reactant zones 922 and 924 as indicated by arrows 932 and 934, respectively. The second reactant flows from second reactant zone 922 through apertured section 923 into first reactant zone 920 as indicated by arrows 933. The second reactant also flows from second reactant zone 924 through apertured section 925 into first reactant zone 920 as indicated by arrows 935. In the first reactant zone 920, the second reactant disperses into the first reactant to form the multiphase reaction mixture. The multiphase reaction mixture that is formed in the first reactant zone 920 has a continuous phase with the first reactant forming the continuous phase, and a dispersed phase with the second reactant forming the dispersed phase. The dispersed phase may be in the form of gas bubbles and/or liquid droplets dispersed in the continuous phase. The multiphase reaction mixture flows through the reaction zone 902, and reacts to form the desired product. The product flows into product footer 906 and out of the microchannel reactor 900 as indicated by arrow 936. Heat exchange fluid enters the heat exchange manifold 908, as indicated by arrow 937, circulates through the reactor core 902, returns to the heat exchange manifold 908, and exits the heat exchange manifold 908 as indicated by arrow 938.

The operation of microchannel reactor 900A is similar to that of microchannel 900. The first reactant flows into the first reactant zone 920A as indicated by arrow 930. The second reactant flows into second reactant zones 922A and 924A as indicated by arrows 932 and 934, respectively. The second reactant flows from second reactant zone 922A through apertured section 923A into first reactant zone 920A as indicated by arrows 933. The second reactant also flows from second reactant zone 924A through apertured section 925A into first reactant zone 920A as indicated by arrows 935. In the first reactant zone 920, the second reactant disperses into the first reactant to form the multiphase reaction mixture. The multiphase reaction mixture that is formed in the first reactant zone 920 has a continuous phase with the first reactant forming the continuous phase, and a dispersed phase with the second reactant forming the dispersed phase. The dispersed phase may be in the form of gas bubbles and/or liquid droplets dispersed in the continuous phase. The multiphase reaction mixture flows through the reaction zone 902, and reacts to form the desired product. The product flows into product footer 906 and out of the microchannel reactor 900 as indicated by arrow 936. Heat exchange fluid enters the heat exchange manifold 908, as indicated by arrow 937, circulates through the reactor core 902, returns to the heat exchange manifold 908, and exits the heat exchange manifold 908 as indicated by arrow 938.

The microchannel reactors 900 and 900A may be used in combination with one or more storage vessels, pumps, valves, manifolds, microprocessors, flow control devices, and the like, which are not shown in the drawings, but would be apparent to those skilled in the art.

Figure 36:
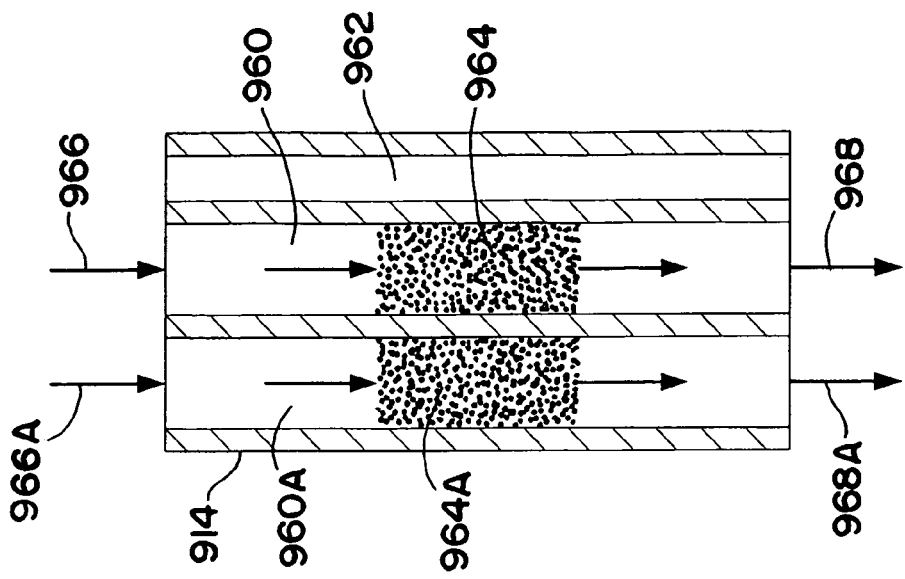
FIG. 36 is a schematic illustration of a repeating unit comprising adjacent process microchannels and a heat exchange channel which may be used in the microchannel reactor illustrated in FIG. 32 or FIG. 33.
Figure 35:
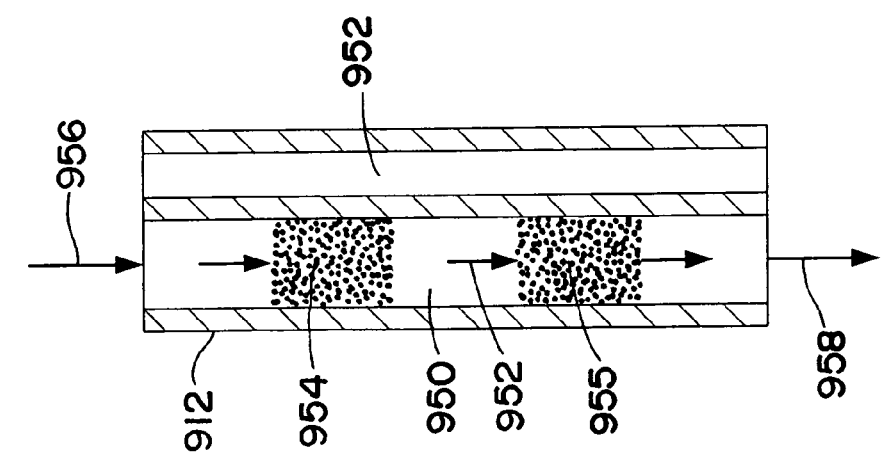
FIG. 35 is a schematic illustration of a repeating unit comprising a process microchannel and a heat exchange channel that may be used in the microchannel reactor illustrated in FIG. 32 or FIG. 33, the process microchannel containing two reaction zones.
Figure 34:
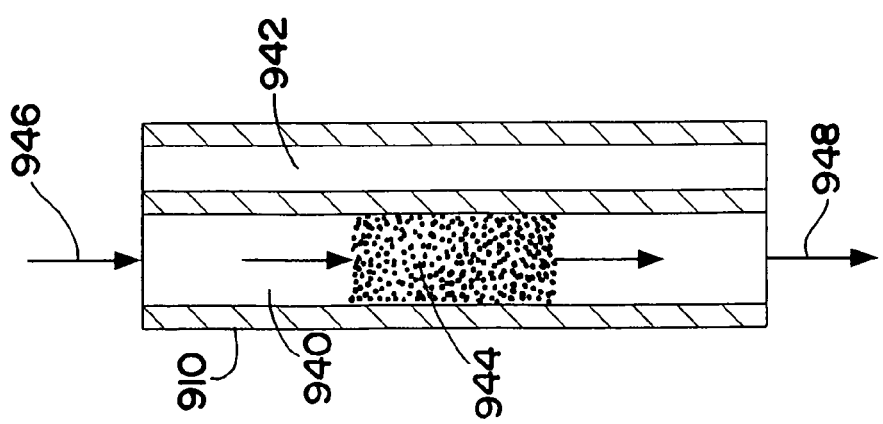
FIG. 34 is a schematic illustration of a repeating unit comprising a process microchannel and a heat exchange channel that may be used in the microchannel reactor illustrated in FIG. 32 or FIG. 33, the process microchannel containing a reaction zone.

Repeating units that may be used in the reactor core 902 are illustrated in FIGS. 34-36. Referring to FIG. 34, repeating unit 910 comprises process microchannel 940, heat exchange channel 942, and reaction zone 944. The reaction zone 944 contains a catalyst. The multiphase reaction mixture flows from the feedstream header 904 or 904A into the process microchannel 940 as indicated by arrow 946. The multiphase reaction mixture contacts the catalyst in the reaction zone 944 and reacts to form the desired product. The product flows from the reaction zone 944 out of the process microchannel 940 as indicated by arrow 948. Heat exchange fluid flows in heat exchange channel 942 and exchanges heat with the process microchannel 940. The exchange of heat between the heat exchange channel 942 and process microchannel 940 may result in a cooling of the process microchannel 940 or a heating of the process microchannel 940. The heat exchange fluid may flow in the heat exchange channel 942 in a direction that is cocurrent, countercurrent or cross-current relative to the direction of flow of fluid in the process microchannel 940.

The repeating unit 912 illustrated in FIG. 35 is similar to the repeating unit 910 illustrated in FIG. 34 with the exception that the repeating unit 912 includes two reaction zones 954 and 955 in the process microchannel rather than one reaction zone. Repeating unit 912 comprises process microchannel 950 and heat exchange channel 952. The catalyst that may be employed in the reaction zones 954 and 955 may be the same, or it may be different. For example, a first reaction may be conducted in the reaction zone 954, and a different reaction may be conducted in the reaction zone 955. In operation, the multiphase reaction mixture flows into process microchannel 950 from feedstream header 904 or 904A as indicated by arrow 956. The multiphase reaction mixture flows through reaction zone 954 and reacts to form an intermediate product. The intermediate product then flows into reaction zone 955 as indicated by arrow 952. The final product is formed in reaction zone 955 and exits the repeating unit 912 as indicated by arrow 958. The product flows from the repeating unit 912 to and through the product footer 906 and out of the microchannel reactor 900 or 900A as indicated by arrow 936.

The repeating unit 914 illustrated in FIG. 36 is similar to the repeating unit 910 illustrated in FIG. 34 with the exception that the repeating unit 914 includes two process microchannels 960 and 960A rather than one process microchannel. Repeating unit 914 comprises process microchannels 960 and 960A and heat exchange channel 962. The process microchannels 960 and 960A contain reaction zones 964 and 964A, respectively. In operation, the multiphase reaction mixture flows into process microchannels 960 and 960A from feedstream header 904 or 904A as indicated by arrows 966 and 966A, respectively. The multiphase reaction mixture flows through reaction zones 964 and 964A and reacts to form the desired product. The product exits the repeating unit 914 as indicated by arrows 968 and 968A. The product flows from the repeating unit 914 to and through the product footer 906 and out of the microchannel reactor 900 or 900A as indicated by arrow 936.

Figure 37:
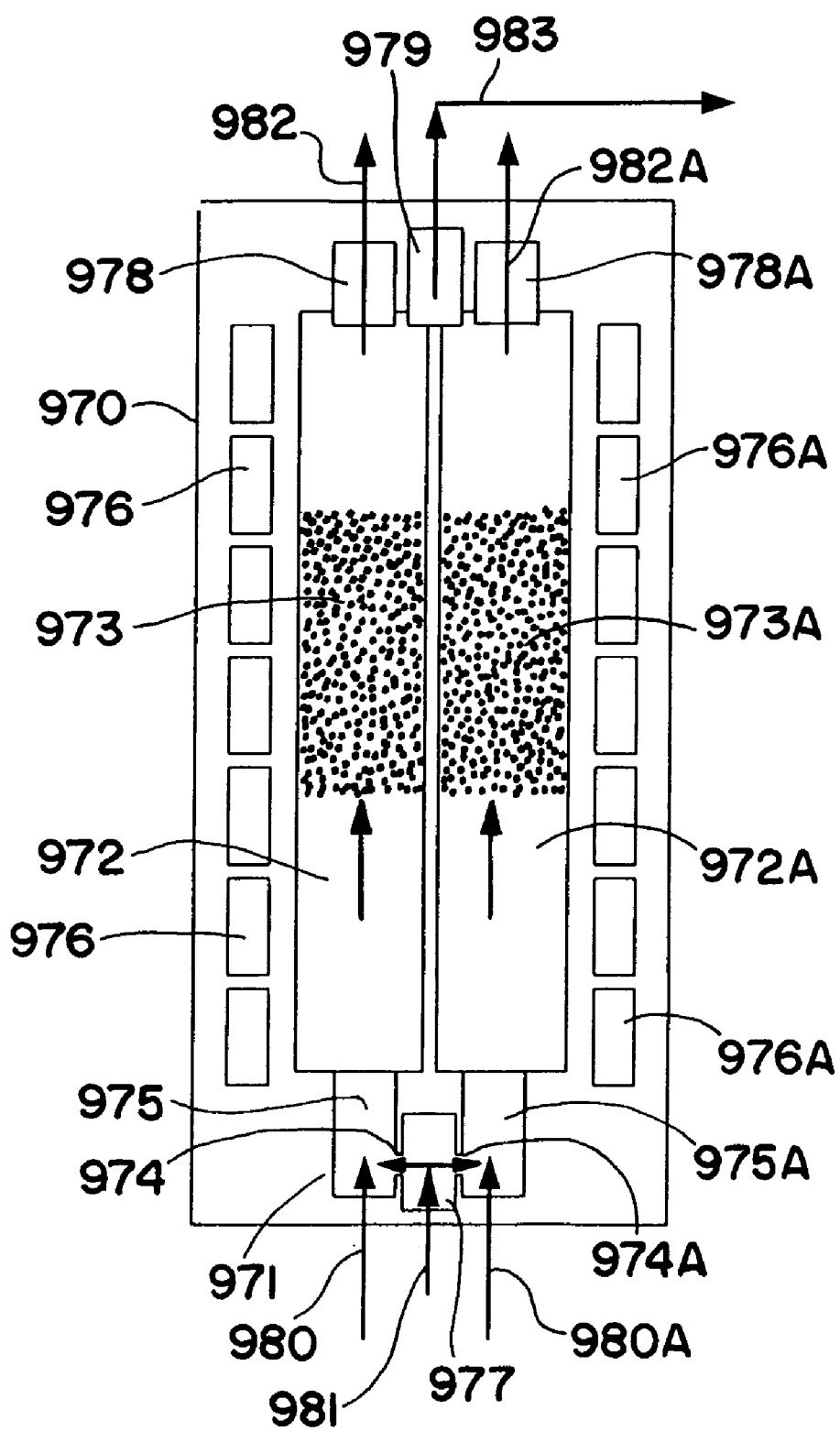
FIG. 37 is a schematic illustration of a repeating unit comprising adjacent process microchannels, heat exchange zones adjacent to the process microchannels, and a manifold for dispersing the second reactant into the first reactant to form a multiphase reaction mixture, the multiphase reaction mixture flowing through reaction zones in the process microchannels to form the desired product.
Figure 38:
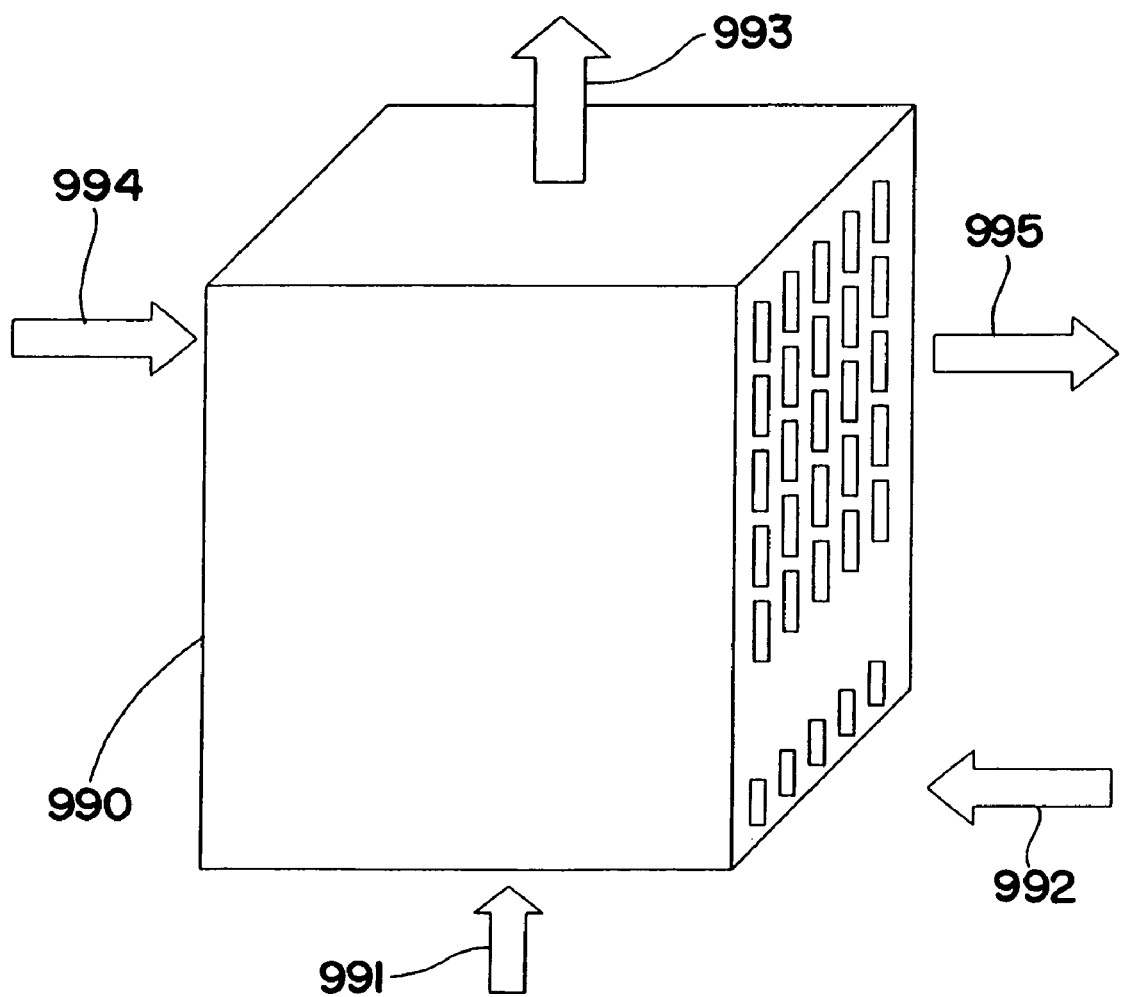
FIG. 38 is a schematic illustration of a microchannel reactor for housing one or more of the repeating units illustrated in FIG. 37.

In one embodiment, the inventive process may be conducted in a microchannel reactor as illustrated, for example, in FIGS. 37 and 38. Referring to FIG. 37, the process may be conducted using repeating unit 970 which includes process microchannels 972 and 972A, and heat exchange channels 976 and 976A. The repeating unit 970 also includes an inlet manifold 971 which includes first reactant zones 975 and 975A and second reactant zone 977. Apertured sections 974 and 974A are positioned between second reactant zone 977 and first reactant zones 975 and 975A, respectively. The repeating unit 970 also includes product footers 978 and 978A, and an optional gas disengagement footer 979. In operation, the first reactant flows into the first reactant zones 975 and 975A as indicated by arrows 980 and 980A. The second reactant flows into second reactant zone 977 as indicated by arrow 981 and from there through apertured sections 974 and 974A into first reactant zones 975 and 975A, respectively. The multiphase reaction mixture is formed in first reactant zones 975 and 975A. The multiphase reaction mixture contains the first reactant in the form of a continuous phase and the second reactant in the form of a dispersed phase. The dispersed phase may be in the form of gas bubbles and/or liquid droplets. The multiphase reaction mixture flows into the reaction zones 973 and 973A, reacts to form the desired product and flows to and through the product footers 978 and 978A and out of the microchannel repeating unit 970 as indicated by arrows 982 and 982A. Optionally, gases may be disengaged from the product. The disengaged gases may exit the microchannel repeating unit 970 through the gas disengagement footer 979 as indicated by arrow 983. Surface features positioned within the process microchannels 972 and 972A downstream of the reaction zones 973 and 973A may be used to facilitate separation of gases from the liquid. Surface features that may be used are discussed in greater detail below. In one embodiment, the disengagement sections within the process microchannels may take the form of a pore throats or capillary structures, where liquid wets and fills small pores or structures such that capillary forces hold the liquid in the pores or structures. The capillary force of the liquid may exceed the breakthrough pressure of the gas, such that gas cannot be pulled into the pores or structures. Examples of pore throat structures that may be used are disclosed in U.S. Pat. application Ser. No. 11/177,941 filed Jul. 8, 2005, which is incorporated herein by reference.

In one embodiment, the gas disengagement section may be positioned at an interior point within the process microchannel such that another second reactant may be added downstream of the gas disengagement section to permit a second reaction to occur. The disengaged gas may be removed from the reactor or alternatively repressurized and recycled back to the feed stream.

FIG. 38 illustrates microchannel reactor 990 which may be used to house one or more of the microchannel repeating units 970 illustrated in FIG. 37. With the microchannel reactor 990, the first reactant enters the microchannel reactor as indicated by arrow 991, and the second reactant enters as indicated by arrow 992. The product exits the microchannel reactor 990 as indicated by arrow 993. Heat exchange fluid flows into the microchannel reactor 990 as indicated by arrow 994 and exits the microchannel reactor 990 as indicated by arrow 995.

Although only one repeating unit (200, 200A, 200B, 200C, 300, 300A, 400, 500, 600, 910, 912, 914 or 970) is illustrated in each of FIGS. 3-11 and 34-37, there is practically no upper limit to the number of repeating units that may be used in the microchannel reactor core 102 or 902 or microchannel reactor 990. For example, one, two, three, four, five, six, eight, ten, twenty, fifty, one hundred, hundreds, one thousand, thousands, ten thousand, tens of thousands, one hundred thousand, hundreds of thousands, millions, etc., of the repeating units described above may be used. In one embodiment, each repeating unit may be manifolded. Manifolding may be effected by connecting macrotubing, piping or ducting to each repeating unit. Alternatively, many of the repeating units may be internally manifolded within the microchannel reactor containing the repeating units by creating relatively equal pressure drop circuits between each unit. In one embodiment, the pressure drop may not be equal between each repeating unit; in this embodiment some flow maldistribution may not affect product quality. In one embodiment, up to about a 50% flow maldistribution may be acceptable using the inventive process. The repeating units may be aligned side-by-side or stacked one above another. The repeating units may be oriented vertically, horizontally, or at an angle inclined from the horizontal.

The second reactant stream channels (240, 340, 470, 470a, 550, 560, 620, 630) and staged addition liquid catalyst channels (360) may be microchannels although they may have larger dimensions that would not characterize them as microchannels. The process microchannels (210, 310, 410, 510, 520, 530, 540, 610, 940, 950, 960, 960A, 972, 972A), second reactant stream channels (240, 340, 470, 470a, 550, 560, 620, 630) and staged addition liquid catalyst channels (360) may have at least one internal dimension of height or width of up to about 10 mm, and in one embodiment from about 0.05 to about 10 mm, and in one embodiment about 0.05 to about 5 mm, and in one embodiment about 0.05 to about 2 mm, and in one embodiment about 0.05 to about 1.5 mm, and in one embodiment about 0.05 to about 1 mm, and in one embodiment about 0.05 to about 0.5 mm. The height or width may range from about 0.15 to about 10 mm, and in one embodiment from about 0.2 to about 10 mm, and in one embodiment from about 0.3 to about 10 mm. The height or width may range from about 0.2 to about 5 mm, and in one embodiment from about 0.2 to about 3 mm, and in one embodiment from about 0.3 to about 2 mm. The other internal dimension of height or width may be of any value, for example, it may range up to about 100 cm, and in one embodiment from about 0.01 to about 100 cm, and in one embodiment from about 0.1 cm to about 100 cm, and in one embodiment from about 0.1 to about 75 cm, and in one embodiment from about 0.1 to about 50 cm, and in one embodiment about 0.2 cm to about 25 cm. The length of the process microchannels, second reactant stream channels and staged addition liquid catalyst channels may be of any value, although, as suggested by the drawings, the length of the second reactant stream channels and staged addition liquid catalyst channels may be less than the length of the next adjacent process microchannels. The lengths of each of these channels may be in the range up to about 10 m, and in one embodiment from about about 1 cm to about 10 m, and in one embodiment from about 1 cm to about 5 m, and in one embodiment 1 cm to about 2.5 m, and in one embodiment from about 1 cm to about 1 m, and in one embodiment from about 2 cm to about 50 cm, and in one embodiment about 2 to about 25 cm.

In one embodiment, flow and/or mixing within the process microchannels (210, 310, 410, 510, 520, 530, 540, 610, 940, 950, 960, 960A, 972, 972A) may be enhanced by the use of surface features formed on one, two or more interior walls of the process microchannels. The surface features may be in the form of depressions in and/or projections from one or more of the microchannel walls. These surface features may be oriented at angles relative to the direction of flow through the process microchannels. The surface features may be aligned at an angle from about 1° to about 89°, and in one embodiment from about 30° to about 75°, relative to the direction of flow. The angle of orientation may be an oblique angle. The angled surface features may be aligned toward the direction of flow or against the direction of flow. The flow of the reactants in contact with the surface features may force one or more of the reactants into depressions in the surface features, while other reactants may flow above the surface features. Flow within the surface features may conform with the surface feature and be at an angle to the direction of the bulk flow in the microchannel. As the reactants exit the surface features they may exert momentum in the x and y direction for an x,y,z coordinate system wherein the bulk flow is in the z direction. This may result in a churning or rotation in the flow of the reactants. This pattern may be helpful for mixing a two-phase flow as the imparted velocity gradients may create fluid shear that breaks up one of the phases into small and well dispersed bubbles or droplets.

In one embodiment, two or more surface feature regions within the process microchannels may be placed in series such that mixing of the reactants and reaction to form the product may be accomplished using a first surface feature region, followed by at least one second surface feature region where a different flow pattern is used. The second flow pattern may be used to separate one or more unreacted reactants or the product from the reaction mixture. The second surface feature region may be used to assist gas or liquid recovery. This may be helpful for gas-liquid reactions, where a gas may be introduced into a liquid to form a reaction mixture which flows through the first surface feature region and undergoes reaction, followed by flow through the second surface feature region where the product and/or one or more unreacted reactants are separated from the reaction mixture. In one embodiment, the second surface feature region may be positioned within the interior of the process microchannel and another second reactant may be combined with the multiphase reaction mixture downstream of the second surface feature region; another reaction may be conducted within the process microchannel downstream of the second surface feature region. In the second surface feature region, a flow pattern may be used that creates a centrifugal force that drives liquid toward the interior walls of the process microchannels while the gas remains in the fluid core. One pattern of surface features that may create a strong central vortex in the fluid may comprise a pair of angled slots on the top and bottom of the process microchannel. This pattern of surface features may be used to create a central swirling flow pattern.

In one embodiment, a liquid catalyst that flows along the walls of the process microchannels may be used. The flow of the catalyst may be cocurrent or counter-current to the flow of the reactants in the process microchannel. Surface features in the interior walls of the process microchannel may be used to enhance the wetting of the process microchannel walls with the catalyst.

In one embodiment, solid particles in the form of a fluidized bed may be in the process microchannel, and the process microchannel may comprise surface features formed in and/or on one or more of its interior walls for modifying the flow of the reactants and/or product within the process microchannel.

One or more of the interior walls of the process microchannels (210, 310, 410, 510, 520, 530, 540, 610, 940, 950, 960, 960A, 972, 972A), second reactant stream channels (240, 340, 470, 470a, 550, 560, 620, 630) and/or staged addition liquid catalyst channels (360) may contain surface features for modifying flow and/or mixing within the channels. Examples of these surface features are illustrated in FIGS. 27-31. The surface features may have two or more layers stacked on top of each other or intertwined in a three-dimensional pattern. The pattern in each discrete layer may be the same or different. Flow may rotate or advect in each layer or only in one layer. Sub-layers, which may not be adjacent to the bulk flow path of the channel, may be used to create additional surface area. For example, these may be used to deposit a catalyst. The flow may rotate in the first level of surface features and diffuse molecularly into the second or more sublayers to promote reaction. Three-dimensional surface features may be made via metal casting or other processes where varying patterns may be broken into discrete planes as if stacked on top of one another. Three-dimensional surface features may be provided adjacent to the bulk flow path within the microchannel where the surface features have different depths, shapes, and/or locations accompanied by sub-features with patterns of varying depths, shapes and/or locations. The surface features may be advantageous for chemical reactions requiring additional surface area for catalyst deposition or for separation steps.

Figure 28:
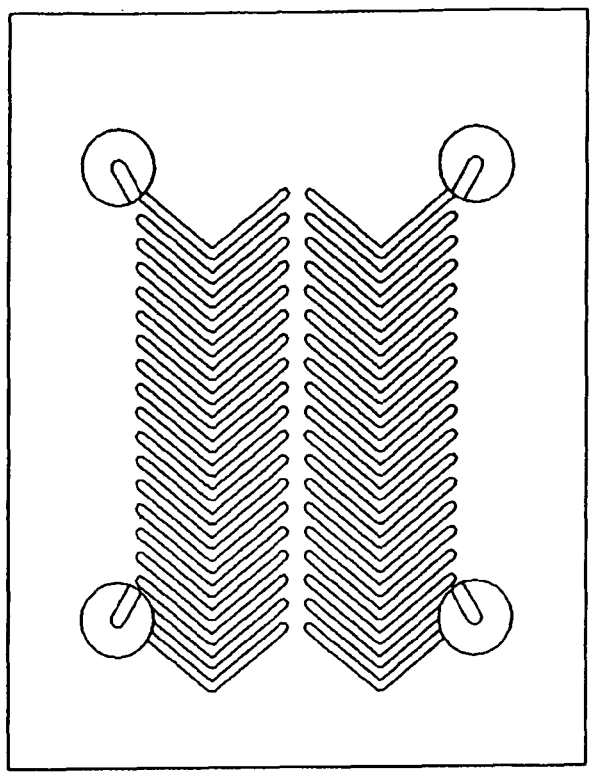
Figure 29:
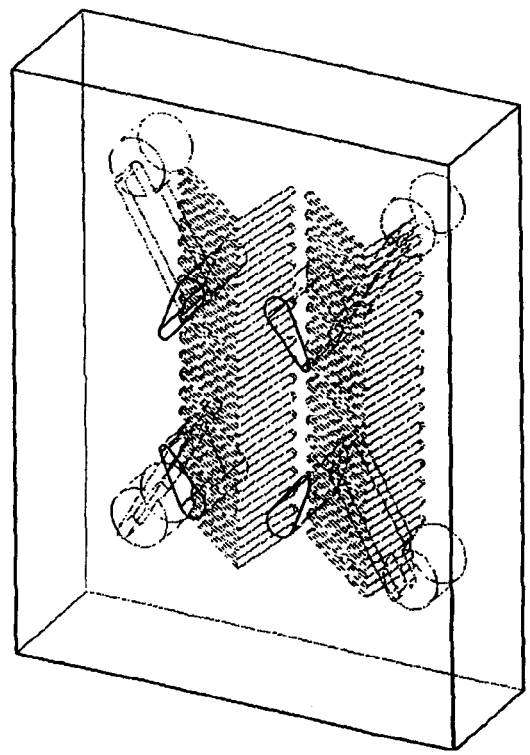

FIG. 28 is a schematic illustration of a top view of a three-dimensional surface feature structure. An example of a back view of a three-dimensional surface feature structure is illustrated in FIG. 29 where recessed chevrons are provided at the interface adjacent the bulk flow path of the microchannel. Beneath the chevrons are a series of three-dimensional structures that connect to the surface features adjacent to the bulk flow path but are made from structures of assorted shapes, depths, and/or locations. It may be further advantageous to provide sublayer passages that do not directly fall beneath an open surface feature that is adjacent to the bulk flow path within the microchannel but rather connect through one or more tortuous two-dimensional or three-dimensional passages. This approach may be advantageous for creating tailored residence time distributions in the microchannels, where it may be desirable to have a wider versus more narrow residence time distribution.

Figure 30:
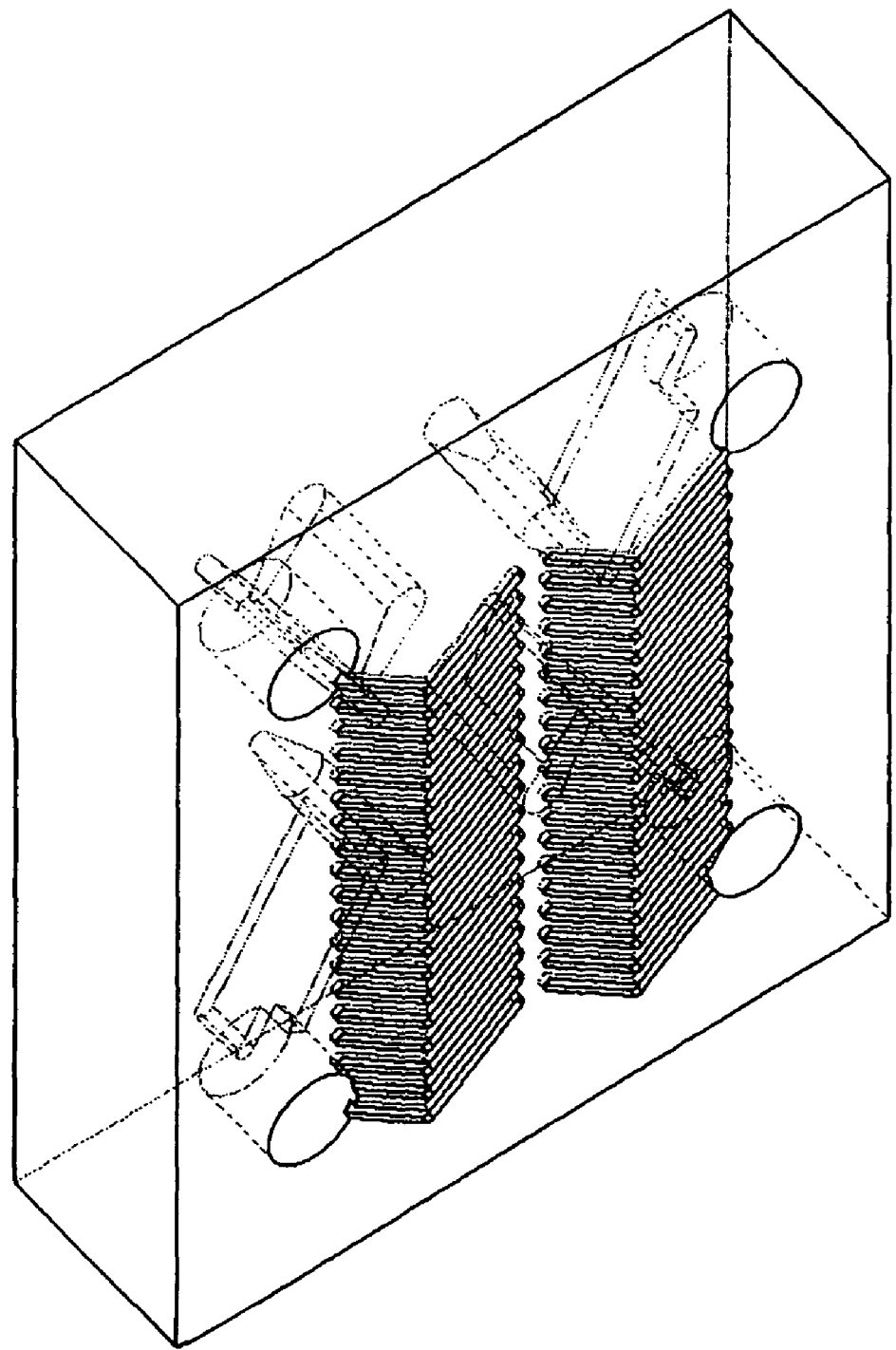

FIG. 30 is a front view of a three-dimensional surface feature where recessed chevrons abut the bulk flow path within the microchannel and have additional surface features of different shapes behind them at varying depths and locations.

The length and width of a surface feature may be defined in the same way as the length and width of a microchannel. The depth may be the distance which the surface feature sinks into or rises above the microchannel surface. The depth of the surface features may correspond to the direction of stacking a stacked and bonded microchannel device with surface features formed on or in the sheet surfaces. The dimensions for the surface features may refer the maximum dimension of a surface feature; for example the depth of a rounded groove may refer to the maximum depth, that is, the depth at the bottom of the groove.

The surface features may have depths that are less than about 2 mm, and in one embodiment less than about 1 mm, and in one embodiment in the range from about 0.01 to about 2 mm, and in one embodiment in the range from about 0.01 to about 1 mm, and in one embodiment in the range from about 0.01 mm to about 0.5 mm. The width of the surface features may be sufficient to nearly span the microchannel width (as shown in the herringbone designs), but in one embodiment (such as the fill features) can span about 60% or less of the width of the microchannel, and in one embodiment about 50% or less, and in one embodiment about 40% or less, and in one embodiment from about 0.1% to about 60% of the microchannel width, and in one embodiment from about 0.1% to about 50% of the microchannel width, and in one embodiment from about 0.1% to about 40% of the microchannel width. The width of the surface features may be in the range from about 0.05 mm to about 100 cm, and in one embodiment in the range from about 0.5 mm to about 5 cm, and in one embodiment in the range from about 1 to about 2 cm.

Multiple surface features or regions of surface features may be included within a microchannel, including surface that recess at different depths into one or more microchannel walls. The spacing between recesses may be in the range from about 0.01 mm to about 10 mm, and in one embodiment in the range from about 0.1 to about 1 mm. The surface features may be present throughout the entire length of a microchannel or in portions or regions of the microchannel. The portion or region having surface features may be intermittent so as to promote a desired reaction or unit operation (for example, separation, heating, cooling, etc.) in tailored zones. For example, a one-centimeter section of a microchannel may have a tightly spaced array of surface features, followed by four centimeters of a flat channel without surface features, followed by a two-centimeter section of loosely spaced surface features. The term "loosely spaced surface features" may be used to refer to surface features with a pitch or feature to feature distance that is more than about five times the width of the surface feature.

In one embodiment, the surface features may be in one or more surface feature regions that extend substantially over the entire axial length of a microchannel. In one embodiment, a microchannel may have surface features over about 50% or less of its axial length, and in one embodiment over about 20% or less of its axial length. In one embodiment, the surface features may extend over about 10% to about 100% of the axial length of the microchannel, and in one embodiment from about 20% to about 90%, and in one embodiment from about 30% to about 80%, and in one embodiment from about 40% to about 60% of the axial length of a microchannel.

Figure 27:
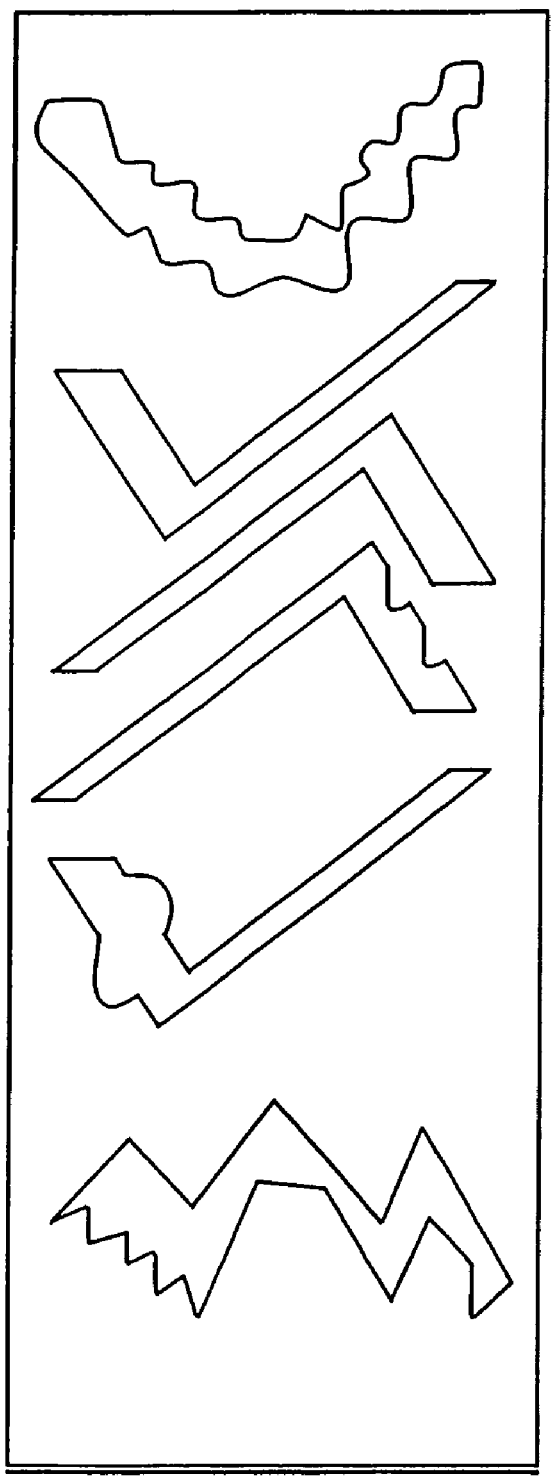
FIGS. 27-31 are schematic illustrations of surface features that may be provided in microchannels used with the inventive process.
Figure 31:
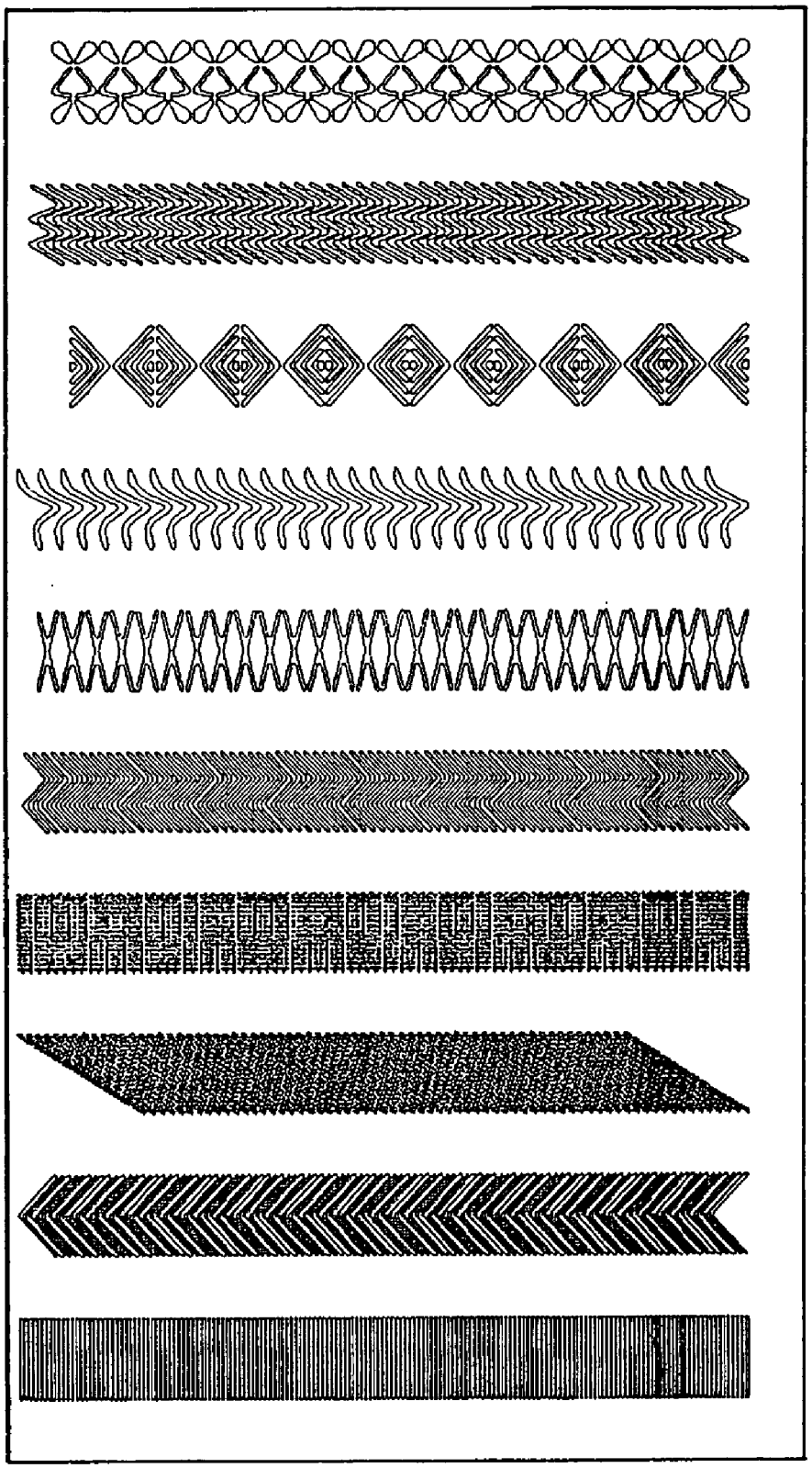

FIGS. 27 and 31 show a number of different patterns that may be used for surface features. These patterns are not intended to limit the invention, only to illustrate a number of possibilities. As with any surface feature, the patterns may be used in different axial or lateral sections of a microchannel.

The apertures (252, 352, 372, 444, 444a, 513, 523, 533, 543) may be of sufficient size to permit the flow of the second reactant through the apertured sections. The apertures may be referred to as pores. The apertured sections (250, 350, 370, 440, 440a, 511, 521, 531, 541, 640, 650, 660, 670, 923, 925, 923A, 925A, 974, 974A) containing the foregoing apertures may have thicknesses in the range from about 0.01 to about 50 mm, and in one embodiment about 0.05 to about 10 mm, and in one embodiment about 0.1 to about 2 mm. The apertures may have average diameters in the range up to about 250 microns, and in one embodiment up to about 100 microns, and in one embodiment up to about 50 microns, and in one embodiment in the range from about 0.001 to about 50 microns, and in one embodiment from about 0.05 to about 50 microns, and in one embodiment from about 0.1 to about 50 microns. In one embodiment, the apertures may have average diameters in the range from about 0.5 to about 10 nanometers (nm), and in one embodiment about 1 to about 10 nm, and in one embodiment about 5 to about 10 nm. The number of apertures in the apertured sections may be in the range from about 1 to about $5 \times 10^8$ apertures per square centimeter, and in one embodiment about 1 to about $1 \times 10^6$ apertures per square centimeter. The apertures may or may not be isolated from each other. A portion or all of the apertures may be in fluid communication with other apertures within the apertured section; that is, a fluid may flow from one aperture to another aperture. The ratio of the thickness of the apertured sections (250, 350, 370, 440, 440a, 511, 521, 531, 541, 640, 650, 660, 670) to the length of the apertured sections along the flow path of the fluids flowing through the process microchannels (210, 310, 410, 510, 520, 530, 540, 610) may be in the range from about 0.001 to about 1, and in one embodiment about 0.01 to about 1, and in one embodiment about 0.03 to about 1, and in one embodiment about 0.05 to about 1, and in one embodiment about 0.08 to about 1, and in one embodiment about 0.1 to about 1.

In one embodiment, the apertured sections (250, 350, 370, 440, 440a, 511, 521, 531, 541, 640, 650, 660, 670) may comprise an interior portion that forms part of one or more of the interior walls of each process microchannel (210, 310, 410, 510, 520, 530, 540, 610). A surface feature sheet may overlie this interior portion of the apertured section. Surface features may be formed in and/or on the surface feature sheet. The second reactant may flow through the apertured section and the surface feature sheet into the process microchannel. Part of the second reactant may be detached from the surface of the surface feature sheet while part may flow within the surface features of the surface feature sheet. The surface feature sheet may contain angled surface features that have relatively small widths or spans relative to the overall flow length. The surface feature sheet may provide mechanical support for the apertured section. The surface features may impart a vortical flow pattern to the second reactant. The vortical flow pattern may impart shear to the second reactant flowing through the apertured section and thus reduce the size of the second reactant bubbles or droplets in the bulk flow path.

Figure 12:
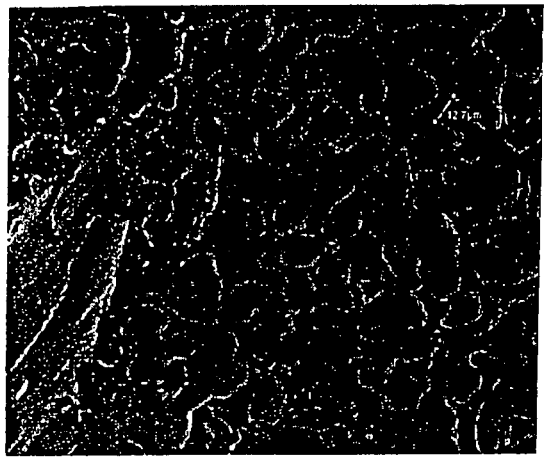
FIG. 12 is a scanning electron microscopic (SEM) image of a porous stainless steel substrate before being heat treated; this substrate may be used for making an apertured section for a process microchannel used with the inventive process.
Figure 13:
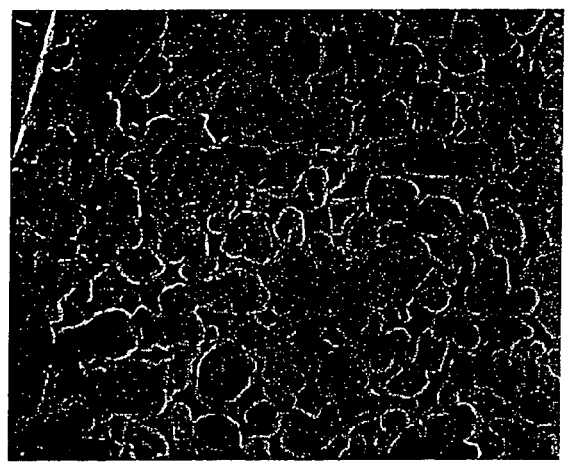
FIG. 13 is an SEM image of the substrate illustrated in FIG. 12 after being heat treated; this substrate may be used for making an apertured section for a process microchannel used with the inventive process.

The apertured sections (250, 350, 370, 440, 440a, 511, 521, 531, 541, 640, 650, 660, 670, 923, 925, 923A, 925A, 974, 974A) may be constructed of any material that provides sufficient strength and dimensional stability to permit the operation of the inventive process. These materials include: steel (e.g., stainless steel, carbon steel, and the like); monel; inconel; aluminum; titanium; nickel; platinum; rhodium; copper; chromium; brass; alloys of any of the foregoing metals; polymers (e.g., thermoset resins); ceramics; glass; composites comprising one or more polymers (e.g., thermoset resins) and fiberglass; quartz; silicon; microporous carbon, including carbon nanotubes or carbon molecular sieves; zeolites; or a combination of two or more thereof. The apertures may be formed using known techniques such as laser drilling, microelectro machining system (MEMS), lithography electrodeposition and molding (LIGA), electrical sparkling, photochemical machining (PCM), electrochemical machining (ECM), electrochemical etching, and the like. The apertures may be formed using techniques used for making structured plastics, such as extrusion, or membranes, such as aligned carbon nanotube (CNT) membranes. The apertures may be formed using techniques such as sintering or compressing metallic powder or particles to form tortuous interconnected capillary channels and the techniques of membrane fabrication. The aperatures may be reduced in size from the size provided by any of these methods by the application of coatings over the apertures internal side walls to partially fill the apertures. The selective coatings may also form a thin layer exterior to the porous body that provides the smallest pore size adjacent to the continuous flow path. The smallest average pore opening may be in the range from about one nanometer to about several hundred microns depending upon the desired droplet size for the emulsion. The aperatures may be reduced in size by heat treating as well as by methods that form an oxide scale or coating on the internal side walls of the apertures. These techniques may be used to partially occlude the aperatures to reduce the size of the openings for flow. FIGS. 12 and 13 show a comparison of SEM surface structures of a stainless steel porous substrate before and after heat treatment at the same magnification and the same location. FIG. 12 shows the surface before heat treating and FIG. 13 shows the surface after heat treating. The surface of the porous material after the heat treatment has a significantly smaller gap and opening size. The average distance between the openings is correspondingly increased.

Figure 14:
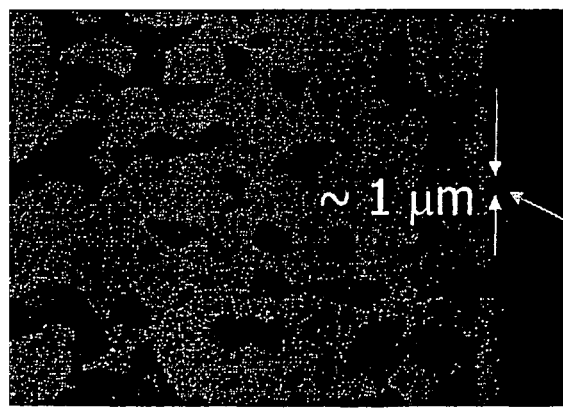
FIG. 14 is an SEM image of a tailored porous substrate which may be used for making an apertured section for a process microchannel used with the inventive process.
Figure 15:
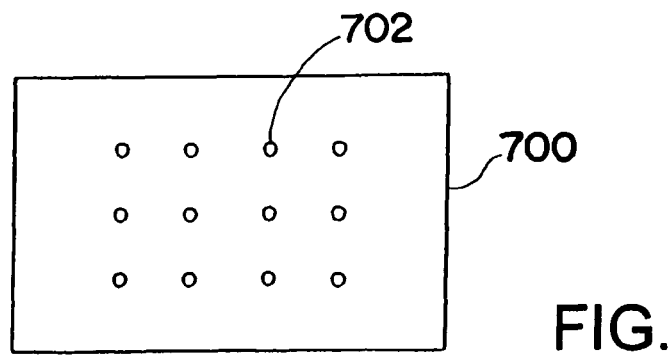
FIG. 15 is a plan view of an apertured sheet which may be useful in making an apertured section for a process microchannel used with the inventive process.
Figure 16:
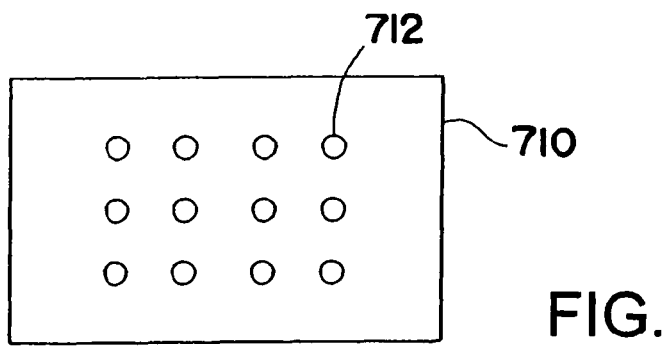
FIG. 16 is a plan view of an apertured sheet or plate which may be useful in making an apertured section for a process microchannel used with the inventive process.

The apertured sections (250, 350, 370, 440, 440a, 511, 521, 531, 541, 640, 650, 660, 670, 923, 925, 923A, 925A, 974, 974A) may be made from a metallic or nonmetallic porous material having interconnected channels or pores of an average pore size in the range from about 0.01 to about 200 microns. These pores may function as the apertures (252, 352, 372, 444, 44a, 513, 523, 533, 543). The porous material may be made from powder or particulates so that the average inter-pore distance is similar to the average pore size. When very small pore sizes are used, the inter-pore distance may also be very small and the droplets may merge at the surface in the side of process microchannels (210, 310, 410, 510, 520, 530, 540, 610) to form unwanted larger droplets. The porous material may be tailored by oxidization at a high temperature in the range from about 300° C. to about 1000° C. for a duration of about 1 hour to about 20 days, or by coating a thin layer of another material such as alumina by sol coating or nickel using chemical vapor deposition over the surface and the inside of pores to block the smaller pores, decrease pore size of larger pores, and in turn increase the inter-pore distance. As such, the merger of droplets may be reduced or eliminated and the formation of smaller droplets may be permitted. An SEM image of a tailored substrate or apertured section is shown in FIG. 14.

The making of substrates for use as apertured sections (250, 350, 370, 440, 440a, 511, 521, 531, 541, 640, 650, 660, 670, 923, 925, 923A, 925A, 974, 974A) with sufficiently small micro-scale apertures or pores (252, 252, 272, 444, 444a, 513, 523, 533, 543) to provide reactants having droplet sizes smaller than about one micron can be problematic. One of the reasons for this lies in the fact that relatively high surface roughness occurs with untreated regular porous materials such as a metallic porous substrates made from powder/particles by compression and/or sintering. These metallic porous substrates typically do not have the required pore size in the surface region when a given nominal pore size is lower than a certain value. While the bulk of the porous material may have the specified nominal pore size, the surface region is often characterized by merged pores and cavities of much larger sizes. This problem can be overcome by tailoring these substrates to provide for the desired pore size and inter-pore distance in the surface region. This may be done by removing a surface layer from the porous substrate and adding a smooth new surface with smaller openings. The droplet size in the reactant mixture that may be formed using these tailored substrates may be reduced without increasing the pressure drop across the substrate. Since direct grinding or machining of the porous surface may cause smearing of the surface structure and blockage of the pores, the porous structure may be filled with a liquid filler, followed by solidification and mechanical grinding/polishing. The filler is then removed to regain the porous structure of the material. The filler may be a metal with a low melting point such as zinc or tin or the precursor of a polymer such as an epoxy. The liquid filling and removing steps may be assisted by the use of a vacuum. Grinding/polishing may be effected using a grinding machine and a grinding powder. Metal filler removal may be effected by melting and vacuum suction, or by acid etching. Epoxies or other polymers may be removed by solvent dissolution or by burn-off in air.

Referring to FIGS. 15-18, the apertured sections (250, 350, 370, 440, 440a, 511, 521, 531, 541, 640, 650, 660, 670, 923, 925, 923A, 925A, 974, 974A), in one embodiment, may be constructed of a relatively thin sheet 700 containing relatively small apertures 702, and a relatively thick sheet or plate 710 containing relatively large apertures 712. The apertures 712 may be aligned with or connected to the apertures 702. The relatively thin sheet 700 overlies and is bonded to the relatively thick sheet or plate 710, the relatively thin sheet 700 facing the interior of process microchannel (210, 310, 410, 510, 520, 530, 540, 610) and the relatively thick sheet 710 facing the interior of the second reactant stream channel (240, 340, 470, 470a, 550, 560, 620, 630) or staged addition liquid catalyst channel (360). The relatively thin sheet 700 may be bonded to the relatively thick sheet 710 using any suitable procedure (e.g., diffusion bonding) to provide a composite construction 720 with enhanced mechanical strength. The relatively thin sheet 700 may have a thickness in the range from about 0.001 to about 0.5 mm, and in one embodiment about 0.05 to about 0.2 mm. The relatively small apertures 702 may have any shape, for example, circular, triangular or rectangular. The relatively small apertures 702 may have an average diameter in the range from about 0.05 to about 50 microns, and in one embodiment about 0.05 to about 20 microns. The relatively thick sheet or plate 710 may have a thickness in the range from about 0.1 to about 5 mm, and in one embodiment about 0.1 to about 2 mm. The relatively large apertures 712 may have any shape, for example, circular, triangular or rectangular. The relatively large apertures 712 may have an average diameter in the range from about 0.1 to about 4000 microns, and in one embodiment about 1 to about 2000 microns, and in one embodiment about 10 to about 1000 micron. The total number of apertures 702 in sheet 700 and the total number of apertures 712 in sheet or plate 710 may be in the range from about 1 to about 10000 apertures per square centimeter, and in one embodiment from about 1 to about 1000 apertures per square centimeter. The sheet 700 and the sheet or plate 710 may be constructed of any of the materials described above as being useful for constructing the apertured sections (250, 350, 370, 440, 440a, 511, 521, 531, 541, 640, 650, 660, 670, 923, 925, 923A, 925A, 974, 974A). The apertures 702 and 712 may be aligned or connected in such a manner that fluid flowing through the apertured sections (250, 350, 370, 440, 440a, 511, 521, 531, 541, 640, 650, 660, 670, 923, 925, 923A, 925A, 974, 974A) flows initially through the apertures 712 then through the apertures 702. The relatively short passageway for the fluid to flow through the relatively small apertures 702 enables the fluid to flow through the apertures 702 with a relatively low pressure drop as compared to the pressure drop that would occur if the passageway in the apertures had a depth equal to the combined depth of apertures 702 and 712.

Figure 17:
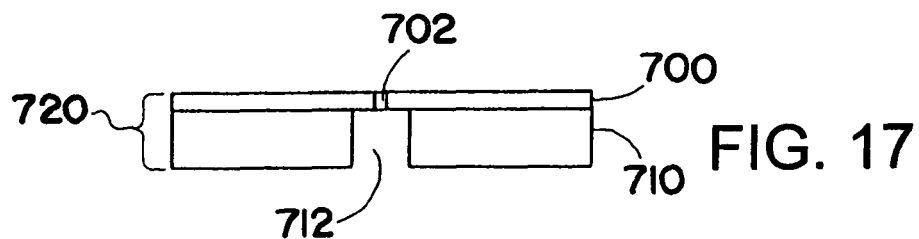
FIG. 17 is a schematic illustration of a relatively thin apertured sheet overlying a relatively thick apertured sheet or plate which may be used in making an apertured section for a process microchannel used with the inventive process.
Figure 18:
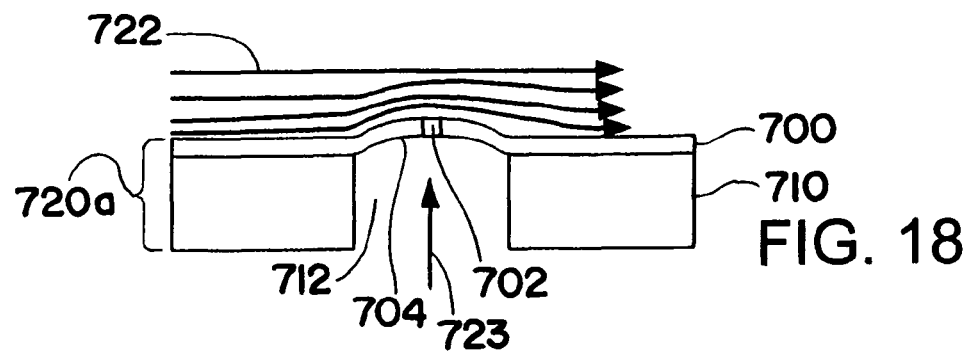
FIG. 18 is a schematic illustration of a relatively thin apertured sheet overlying a relatively thick apertured sheet or plate which may be used in making an apertured section for a process microchannel used with the inventive process.

In the embodiment illustrated in FIG. 18, the composite construction 720a has the same design as illustrated in FIG. 17 with the exception that convex portion 704 of the relatively thin sheet 700 covering the aperture 712 is provided. Convex portion 704 provides increased local shear force in the adjacent channel. The second reactant or liquid catalyst flows through the apertures 712 and 702 in the direction indicated by arrow 723. The directional arrows 722 in FIG. 18 show the flow of the first reactant in the process microchannel adjacent to the aperture 702. The increased local shear force leads to a smaller droplet size for the fluid flowing through the aperture 702.

Figure 19:
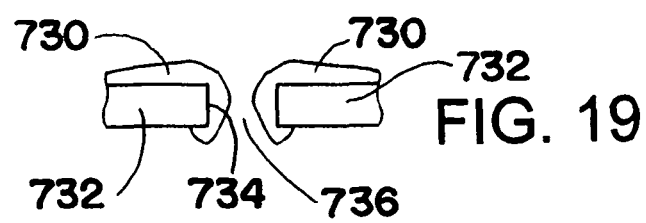
FIG. 19 is a schematic illustration of an alternate embodiment of an aperture that may be used in the apertured section of a process microchannel used with the inventive process, the aperture having a coating partially filling it and overlying its sidewalls.

In the embodiment illustrated in FIG. 19, a surface coating 730 is deposited on the surface of sheet or plate 732 and on the internal sidewalls 734 of aperture 736. This coating provides a facilitated way of reducing the diameter of the apertures (252, 352, 372, 444, 444a, 513, 523, 533, 543). The coating material used to form coating 730 may be alumina, nickel, gold, or a polymeric material (e.g., Teflon). The coating 730 may be applied to the sheet or plate 732 using known techniques including chemical vapor deposition, metal sputtering, metal plating, sintering, sol coating, and the like. The diameter of the apertures may be controlled by controlling the thickness of the coating 730.

In one embodiment, the apertured sections (250, 350, 370, 440, 440a, 511, 521, 531, 541, 640, 650, 660, 670, 923, 925, 923A, 925A, 974, 974A) may be formed from an asymmetric porous material, for example, a porous material having multiple layers of sintered particles. The number of layers may be two, three, or more. An advantage of these multilayered substrates is that they provide enhanced durability and adhesion. Examples include sintered ceramics that have relatively large pores on one side and relatively small pores on the other side. The relatively small pores may have diameters in the range of about 2 to about 10 nm. The relatively small pores may be positioned in a relatively thin layer of the multilayered substrate. The relatively thin layer may have a thickness in the range of about 1 to about 10 microns. The side with the relatively small pores may be placed facing the interior of the process microchannel (210, 310, 410, 510, 520, 530, 540, 610) to take advantage of relatively high shear forces to remove the relatively small droplets of reactant and/or liquid catalyst as they are formed.

During the inventive process the second reactant may flow through the apertured sections (250, 350, 370, 440, 440a, 511, 521, 531, 541, 640, 650, 660, 670) into the process microchannels (210, 310, 410, 510, 520, 530, 540, 610). In one embodiment, the apertured section may extend along at least about 5% of the axial length of the process microchannel, and in one embodiment at least about 20% of the axial length of the process microchannel, and in one embodiment at least about 35% of the axial length of the process microchannel, and in one embodiment at least about 50% of the axial length of the process microchannel, and in one embodiment at least about 65% of the axial length of the process microchannel, and in one embodiment at least about 80% of the axial length of the process microchannel, and in one embodiment at least about 95% of the axial length of the process microchannel, and in one embodiment from about 5% to about 100% of the axial length of the process microchannel, and in one embodiment from about 10% to about 95% of the axial length of the process microchannel, and in one embodiment from about 25% to about 75% of the axial length of the process microchannel, and in one embodiment from about 40% to about 60% of the axial length of the process microchannel. In the process microchannels the second reactant may form gas bubbles and/or liquid droplets dispersed in the first reactant. The second reactant may be in the form of a discontinuous phase. The first reactant may be in the form of a continuous phase. The gas bubbles and/or liquid droplets may be relatively small and uniform in size. These bubbles and/or liquid droplets provide a relatively high interfacial area between the second reactant and the first reactant. This relatively high interfacial area, in at least one embodiment, provides for enhanced rates of reaction between the reactants.

In one embodiment, as illustrated in FIG. 8, liquid catalyst may flow from staged addition liquid catalyst channel 360 through apertured section 370 into process microchannel 310. The liquid catalyst may disperse as liquid droplets in the mixture of first reactant and second reactant. These liquid droplets may have relatively small and uniform sizes. This provides for a relatively high interfacial area between the catalyst and either or both the first reactant and second reactant. This relatively high interfacial area, in at least one embodiment, provides for relatively high rates of reaction between the first reactant and the second reactant.

Figures 25, 26:
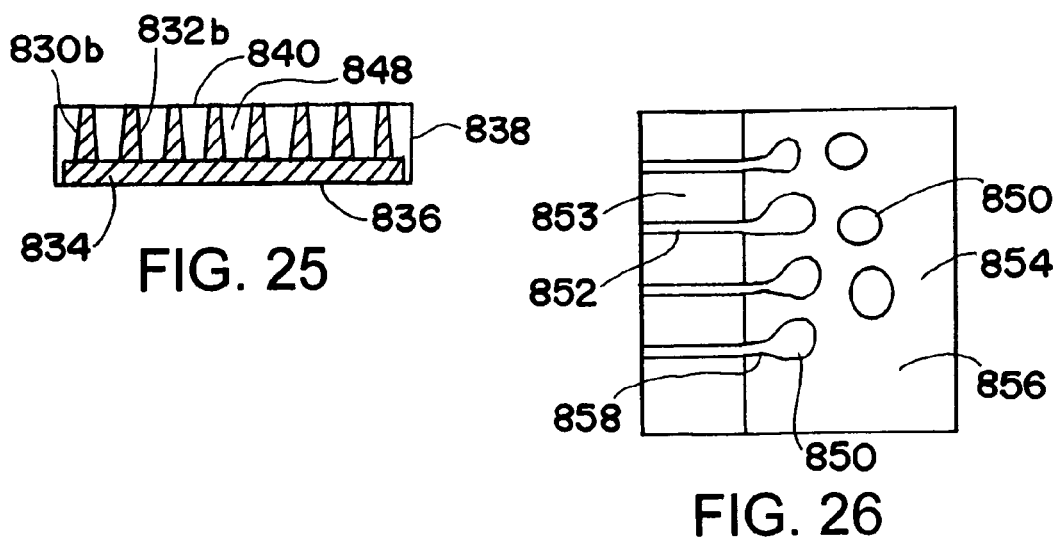
FIG. 25 illustrates another alternate embodiment of the process microchannel and fin assembly illustrated in FIG. 23.
FIG. 26 is a schematic illustration showing the formation of gas or liquid bubbles during the operation of the inventive process.

The formation of gas bubbles or liquid droplets during the inventive process is shown schematically in FIG. 26 for the mixing of the second reactant with the first reactant. This illustration would also be applicable to the mixing of a liquid catalyst with the mixture of the first reactant and second reactant as discussed above. Referring to FIG. 26, the second reactant, in the form of gas bubbles or liquid droplets 850, emerges from apertures 852 in apertured section 853 and flows into process microchannel 854 where the bubbles or droplets are dispersed in the first reactant 856. While attached to the gas or liquid stems 858 within the apertures 852, the gas bubbles or liquid droplets may grow in size, for example, to about 10 times the size of the apertures or larger. Eventually, shear force at the base of the gas or liquid stems 858 detaches the bubbles or droplets from the apertures 852 and the bubbles or droplets disperse in the first reactant 856. In one embodiment, a relatively high pressure drop through the apertures 852 or a correspondingly high second fluid stream flow rate through the second reactant stream channel adjacent to the apertured section 853 may not be necessary to achieve dispersion of the second reactant in the first reactant. A low pressure drop or low flow rate may lead to smaller bubbles or droplets, as lower inertia of the second reactant flowing through the apertured section may reduce bubble or droplet growth before the bubbles or droplets detach from the apertures.

The gas bubbles or liquid droplets of the second reactant or liquid droplets of the liquid catalyst may have volume-based mean diameters in the range up to about 200 microns, and in one embodiment about 0.01 to about 200 microns, and in one embodiment from about 0.01 to about 100 microns, and in one embodiment about 0.01 to about 50 microns, and in one embodiment about 0.01 to about 25 microns, and in one embodiment about 0.01 to about 10 microns, and in one embodiment about 0.01 to about 5 microns, and in one embodiment about 0.01 to about 2 microns, and in one embodiment about 0.01 to about 1 micron, and in one embodiment about 0.01 to about 0.5 micron, and in one embodiment about 0.01 to about 0.2 micron, and in one embodiment about 0.01 to about 0.1 micron, and in one embodiment about 0.01 to about 0.08 micron, and in one embodiment about 0.01 to about 0.05 micron, and in one embodiment about 0.01 to about 0.03 micron. An advantage of the inventive process is that at least in one embodiment the bubbles or droplets may be characterized by having a relatively narrow distribution of average diameters.

"Relative span" is often referred to as "span." It is a dimensionless parameter calculated from volume distribution. As with volume median bubble or droplet size (VMD), D[v,0.1] and D[v,0.9] are diameters representing the points at which 10% and 90%, respectively, of the volume of bubbles or droplets dispersed is in bubbles or droplets of smaller diameter. The span may be defined as D[v,0.9] minus D[v,0.1] which is then divided by the VMD (D[v,0.5]). In one embodiment, the span for the bubbles or droplets of second reactant and/or liquid catalyst in the multiphase reaction mixtures made by the inventive process may be in the range from about 1.3 to about 5, and in one embodiment about 1.8 to about 2.5. In one embodiment, the inventive process may be conducted in a single process microchannel and the span may be in the range of from about 1.3 to about 2.5. In one embodiment, the inventive process may be conducted in a scaled-up process employing multiple process microchannels and the span may be in the range from about 1.3 to about 5.

In one embodiment, the volume-based mean diameter for the bubbles or droplets of second reactant and/or liquid catalyst in the multiphase reaction mixtures made during the inventive process may be in the range from about 0.1 to about 100 microns, and the span may be in the range from about 1 to about 10. In one embodiment, the volume-based mean diameter may be in the range from about 1 to about 10 microns, and the span may be in the range from about 1.8 to about 2.5. In one embodiment, the bubbles or droplets may have a volume-based mean diameter in the range from about 1 to about 25 microns, and a span in the range from about 1.9 to about 2.5.

An advantage of the inventive process, at least in one embodiment, is that the gap distances between the process microchannels, second reactant stream channels, and heat exchange channels may be the same whether the process is intended for laboratory or pilot plant scale or for full production scale. As a result, the particle size distribution of the second reactants in the multiphase reaction mixtures produced by the microchannel reactors used with the inventive process may be substantially the same whether the microchannel reactor is built on a laboratory or pilot plant scale or as a full scale plant unit.

Shear force or stress on a liquid control element (in discretized form) in the direction of velocity u may be calculated by the formula $F_x=mu*du/dy$, where mu is viscosity, and du/dy is the velocity gradient for the liquid flow normal to the apertured section. However, as in a location of liquid (represented by a control element) the velocity generally has three components, and shear force also has three components. For a channel flow near and at the surface, a one dimensional assumption can be made and $F_x$ can approximate the net shear stress at an element surface of the liquid. The use of computational fluid dynamics, including commercial software packages such as Fluent or FEMLAB, may be used to solve the required transport equations such that the surface shear force may be calculated. The surface shear force or stress may be calculated along the channel length, parallel to the direction of flow. Shear force or stress may also be calculated between parallel channels, where flow distribution effects are included to determine the mass flux into each parallel channel as a function of the detailed channel and manifold geometry. Additional calculation methods can be found, for example, in "Fundamentals of Fluid Mechanics," $3^{rd}$ Ed., B. R. Munson, D. F. Young and T. H. Okiishi, John Wiley & Son, Inc., Weinheim, 1998.

In one embodiment, the shear force deviation factor (SFDF) for a process employing a single process microchannel may be within about 50% of the SFDF for a scaled-up process involving multiple process microchannels. SFDF may be calculated using the formula $$SFDF=(F_{max}-F_{min})/(2F_{mean})$$

wherein: $F_{max}$ is the maximum shear stress force in a process microchannel for a specific liquid; $F_{min}$ is the minimum shear stress force in the process microchannel for the liquid; and $F_{mean}$ is the arithmetic average shear force for the liquid at the surface of the apertured section (250, 350, 370, 440, 440a, 511, 521, 531, 541, 640, 650, 660, 670) within the process microchannel. Within a single process microchannel, operated in accordance with the inventive process, the SFDF may be less than about 2, and in one embodiment less than about 1, and in one embodiment less than about 0.5, and in one embodiment less than about 0.2.

In one embodiment, the inventive process may provide for a relatively uniform shear stress force while employing multiple process microchannels. To measure the shear force uniformity among multiple process microchannels, the average shear force is calculated for each channel and compared. $F_{max}$ is the largest value of the average channel shear force, and $F_{min}$ is the smallest value of the average shear force. $F_{mean}$ is the mean of the average shear forces of all the channels. SFDF may be calculated from these values. Among multiple process microchannels, at least with one embodiment of the inventive process, the SFDF may be less than about 2, and in one embodiment less than about 1, and in one embodiment less than about 0.5, and in one embodiment less than about 0.2.

The heat source and/or heat sink may be used for cooling, heating or both cooling and heating. The heat source and/or heat sink may comprise one or more heat exchange channels. The heat source may comprise one or more non-fluid heating elements such as one or more electric heating elements or resistance heaters. The heat sink may comprise one or more non-fluid cooling elements. These may be adjacent to the process microchannels and/or second reactant stream channels. In one embodiment, the heat source and/or heat sink may not be in contact with or adjacent to the process microchannel and/or second reactant stream channels, but rather can be remote from either or both the process microchannel and/or second reactant stream channels, but sufficiently close to the process microchannel and/or second reactant stream channels to transfer heat between the heat source and/or heat sink and the process microchannels and/or second reactant stream channels. The non-fluid heating and/or non-fluid cooling elements can be used to form one or more walls of the process microchannels (210, 310, 410, 510, 520, 530, 540, 610, 940, 950, 960, 960A, 972, 972A) and/or second reactant stream channels (240, 340, 470, 470a, 550, 560, 620, 630). The non-fluid heating and/or cooling elements can be built into one or more walls of the process microchannels and/or second reactant stream channels. The non-fluid heating and/or-cooling elements can be thin sheets, rods, wires, discs or structures of other shapes embedded in the walls of the process microchannels and/or second reactant stream channels. The non-fluid heating and/or cooling elements can be in the form of foil or wire adhered to the process microchannel walls and/or second reactant stream channel walls. Heating and/or cooling may be effected using Peltier-type thermoelectric cooling and/or heating elements. Multiple heating and/or cooling zones may be employed along the length of the process microchannels and/or second reactant stream channels. Similarly, heat transfer fluids at different temperatures in one or more heat exchange channels may be employed along the length of the process microchannels and/or second reactant stream channels. The heat source and/or heat sink can be used to provide precise temperature control within the process microchannels and/or second reactant stream channels.

The heat exchange channels (220, 320, 490, 570, 580, 680, 942, 952, 962, 976, 976A) may be microchannels although they may have larger dimensions that would not typically characterize them as microchannels. Each of these channels may have a cross section that has any configuration, for example, square, rectangular, circular, annular, oval, trapezoidal, etc. The heat exchange channels may be tubular. The heat exchange channels along with adjacent process microchannels or second or third fluid stream channels may be formed from parallel spaced sheets and/or plates positioned side-by-side or one-above-another. Each of the heat exchange channels may have an internal dimension perpendicular to the flow of heat exchange fluid through the heat exchange channel, for example height, width or diameter, in the range up to about 50 mm, and in one embodiment up to about 10 mm, and in one embodiment up to about 2 mm. This dimension may be in the range from about 0.05 to about 50 mm, and in one embodiment about 0.05 to about 10 mm, and in one embodiment about 0.05 to about 5 mm, and in one embodiment from about 0.05 to about 2 mm, and in one embodiment from about 0.5 to about 1 mm. Another internal dimension perpendicular to the flow of heat exchange fluid through the heat exchange channel, for example height or width, may be of any value, for example, in the range from about 0.01 cm to about 100 cm, and in one embodiment about 0.01 cm to about 75 cm, and in one embodiment about 0.1 cm to about 50 cm, and in one embodiment about 0.2 cm to about 25 cm. The length of the heat exchange channels may be of any value, for example, in the range up to about 10 m, and in one embodiment from about 1 cm to about 10 m, and in one embodiment about 1 cm to about 5 m, and in one embodiment about 1 cm to about 2.5 m, and in one embodiment about 1 cm to about 1 m, and in one embodiment about 2 cm to about 50 cm, and in one embodiment about 2 cm to about 25 cm. The separation between each process microchannel or second reactant stream channel and the next adjacent heat exchange channel may be in the range from about 0.05 mm to about 50 mm, and in one embodiment about 0.1 to about 10 mm, and in one embodiment about 0.2 mm to about 2 mm.

The heat exchange channels (220, 320, 490, 570, 580, 680, 942, 952, 962, 976, 976A) may be adapted for heat exchange fluid to flow through the channels in a direction that is co-current with the flow of fluid through the adjacent process microchannels and/or second reactant stream channels. Alternatively, the heat exchange fluid may flow through the heat exchange channels in a direction that is countercurrent to the flow of fluid through the process microchannels and/or second reactant stream channels. Alternatively, the heat exchange channels may be oriented relative to the process microchannels and/or second reactant stream channels to provide for the flow of heat exchange fluid in a direction that is cross-current relative to the flow of fluid through the process microchannels and/or second reactant stream channels. The heat exchange channels may have a serpentine configuration to provide a combination of cross-flow and co-current or counter-current flow.

The heat exchange fluid may be any fluid. These include air, steam, liquid water, gaseous nitrogen, liquid nitrogen, other gases including inert gases, carbon monoxide, carbon dioxide, oils such as mineral oil, gaseous hydrocarbons, liquid hydrocarbons, and heat exchange fluids such as Dowtherm A and Therminol which are available from Dow-Union Carbide.

The heat exchange fluid may comprise the first reactant, second reactant and/or product. This can provide process pre-heat and/or an increase in overall thermal efficiency of the process.

In one embodiment, the heat exchange channels comprise process channels wherein an endothermic or exothermic process is conducted. These heat exchange process channels may be microchannels. Examples of endothermic processes that may be conducted in the heat exchange channels include steam reforming and dehydrogenation reactions. Examples of exothermic processes that may be conducted in the heat exchange channels include water-gas shift reactions, methanol synthesis reactions and ammonia synthesis reactions.

In one embodiment, the heat exchange fluid undergoes a phase change in the heat exchange channels. This phase change provides additional heat addition to or removal from the process microchannels and/or second reactant stream channels beyond that provided by convective heating or cooling. An example of such a phase change would be an oil or water that undergoes boiling. In one embodiment, the vapor mass fraction quantity of the boiling of the phase change fluid may be up to about 100%, and in one embodiment up to about 75%, and in one embodiment up to about 50%.

The heat flux for convective heat exchange in the microchannel reactor may be in the range from about 0.01 to about 125 watts per square centimeter of surface area of the one or more process microchannels ($W/cm^2$) in the microchannel reactor, and in one embodiment about 0.1 to about 50 $W/cm^2$, and in one embodiment from about 1 to about 10 $W/cm^2$. The heat flux for phase change and/or an exothermic or endothermic reaction of the heat exchange fluid may be in the range from about 0.01 to about 250 $W/cm^2$, and in one embodiment from about 1 to about 250 $W/cm^2$, and in one embodiment, from about 1 to about 100 $W/cm^2$, and in one embodiment from about 1 to about 50 $W/cm^2$, and in one embodiment from about 1 to about 25 $W/cm^2$, and in one embodiment from about 1 to about 10 $W/cm^2$.

In one embodiment, the temperature of the reactant streams entering the microchannel reactor may be within about 200°

C., and in one embodiment within about 100° C., and in one embodiment within about 50° C., and in one embodiment within about 20° C., of the temperature of the product exiting the microchannel reactor.

The use of controlled heat exchange between heat exchange channels in close proximity or adjacent to the process microchannels and/or second reactant stream channels may allow for uniform temperature profiles for the process microchannels and/or second reactant stream channels. This provides for the possibility of a more uniform heat exchange at more rapid rates than can be obtained with conventional processing equipment such as mixing tanks. For a microchannel reactor employing multiple process microchannels and second reactant stream channels, the temperature difference between the process microchannels and/or second reactant stream channels at at least one common position along the lengths of the process microchannels may be less than about 5° C., and in one embodiment less than about 2° C., and in one embodiment less than about 1° C.

The heat exchange channels adjacent to either the process microchannels and/or second reactant stream channels may employ separate temperature zones along the length of such channels. For example, in one embodiment, the temperature in a first zone near the entrance to the process microchannel may be maintained at a temperature above or below a second temperature in a second zone near the end of the process microchannel. A cool down or quench zone may be incorporated into the process microchannels to cool the product. Numerous combinations of thermal profiles are possible, allowing for a tailored thermal profile along the length of the process microchannels and/or second reactant stream channels, including the possibility of heating or cooling zones before and/or after the reaction zone in the process microchannels to heat or cool the reactants and/or product.

The heat exchange fluid entering the heat exchange channels may be at a temperature in the range from about −40° C. to about 400° C., and in one embodiment about 0° C. to about 400° C., and in one embodiment from about 20° C. to about 300° C., and in one embodiment from about 20° C. to about 250° C., and in one embodiment from about 20° C. to about 200° C. The heat exchange fluid exiting the heat exchange channels may be at a temperature in the range from about −40° C. to about 400° C., and in one embodiment about 0° C. to about 400° C., and in one embodiment from about 20° C. to about 300° C., and in one embodiment from about 20° C. to about 250° C., and in one embodiment from about 20° C. to about 200° C. The residence time of the heat exchange fluid in the heat exchange channels may be in the range from about 5 ms to about 1 minute, and in one embodiment from about 20 ms to about 1 minute, and in one embodiment from about 50 ms to about 1 minute, and in one embodiment about 100 ms to about 1 minute. The pressure drop for the heat exchange fluid as it flows through the heat exchange channels may be in the range up to about 1 atm/m, and in one embodiment up to about 0.5 atm/m, and in one embodiment up to about 0.1 atm/m, and in one embodiment from about 0.01 to about 1 atm/m. The heat exchange fluid may be in the form of a vapor, a liquid, or a mixture of vapor and liquid. The Reynolds Number for the flow of vapor through the heat exchange channels may be in the range from about 10 to about 5000, and in one embodiment about 100 to about 3000. The Reynolds Number for the flow of liquid through heat exchange channels may be in the range from about 10 to about 10000, and in one embodiment about 100 to about 5000.

The design of the process microchannels may vary along their axial length to accommodate the changing hydrodynamics of the multiphase reaction. For example, if one of the reactants is in excess, then the fluidic properties of the multiphase reaction mixture may change over the course of the reaction as typified by an extent of reaction less than about 10% to an extent of reaction greater than about 50%. For an oxidation reaction where oxygen is fed near the stoichiometric feed rate, at the entrance to the process microchannel the ratio of liquid to gas may be modest, but at the end of the process microchannel the ratio of liquid to gas may be high and approach infinity for reactions that are desired to go to extinction of the gas reactant. Reduction of mass transfer requires good phase mixing. Good phase mixing may require a different design as the gas or alternatively the liquid are reacted to near completion, for example, greater than about 60% conversion, and in one embodiment greater than about 90% conversion. There may be at least one second reaction zone in the process microchannel in which the microchannel cross section is reduced or increased from that in the corresponding first reaction zone to create a different mixing pattern. Surface features, if used, may have a different geometry, pattern, angle, depth, or ratio of size relative to the microchannel gap as the reaction proceeds toward extinction.

The microchannel reactor (100, 900, 900A, 990) may be constructed of any material that provides sufficient strength, dimensional stability and heat transfer characteristics for carrying out the inventive process. Examples of suitable materials include steel (e.g., stainless steel, carbon steel, and the like), aluminum, titanium, nickel, and alloys of any of the foregoing metals, plastics (e.g., epoxy resins, UV cured resins, thermosetting resins, and the like), monel, inconel, ceramics, glass, composites, quartz, silicon, or a combination of two or more thereof. The microchannel reactor may be fabricated using known techniques including wire electrodischarge machining, conventional machining, laser cutting, photochemical machining, electrochemical machining, molding, water jet, stamping, etching (for example, chemical, photochemical or plasma etching) and combinations thereof. The microchannel reactor may be constructed by forming layers or sheets with portions removed that allow flow passage. A stack of sheets may be assembled via diffusion bonding, laser welding, diffusion brazing, and similar methods to form an integrated device. Stacks of sheets may be gasketed together to form an integral device. The microchannel reactor has appropriate manifolds, valves, conduit lines, etc. to control flow of the reactant composition and product, and flow of the heat exchange fluid. These are not shown in the drawings, but can be readily provided by those skilled in the art.

The catalyst may comprise any catalyst suitable for conducting the desired multiphase reactions. The catalyst may be an oxidation catalyst, hydrocracking catalyst, hydrogenation catalyst, hydration catalyst or a carbonylation catalyst. These are discussed above. The catalyst may be in the form of a solid, a liquid, or a mixture thereof.

The liquid catalyst may be in the form of droplets dispersed in the first reactant stream, the second reactant stream, or a mixture of the two streams. These liquid droplets may dissolve to form solutions or disperse to form emulsions. When in the form of emulsions, the droplets may have an average diameter of about 0.01 to about 100 microns, and in one embodiment about 0.1 to about 10 microns. The span for the distribution of droplets may range from about 0.1 to about 4, and in one embodiment about 0.1 to about 2.

Figures 20, 21, 22:
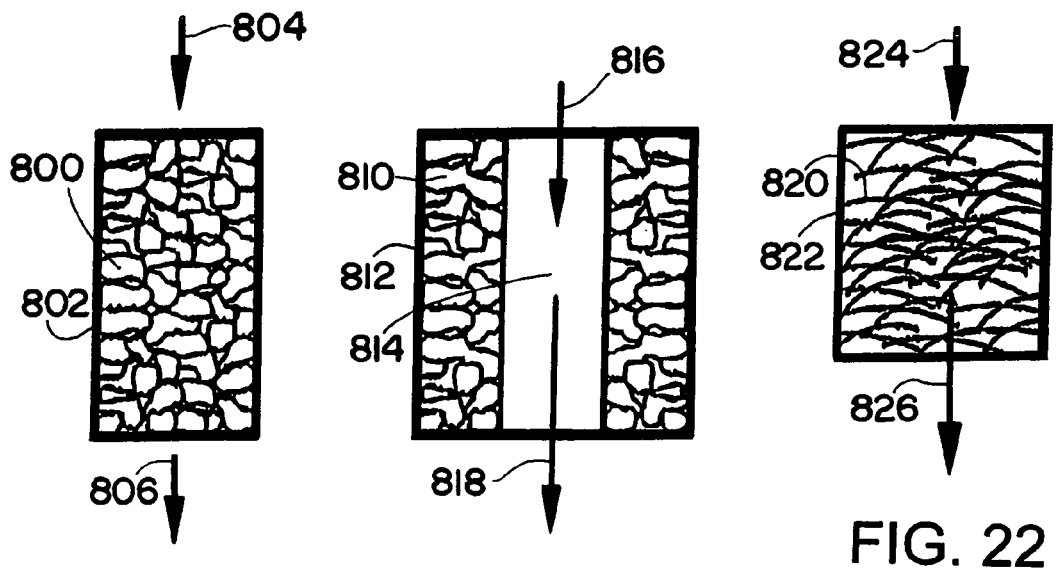
FIG. 20 is a schematic illustration of a process microchannel that may be used with the inventive process, the process microchannel containing a catalyst having a packed bed configuration.
FIG. 21 is a schematic illustration of a process microchannel that may be used with the inventive process, the process microchannel containing a catalyst having a flow-by configuration.
FIG. 22 is a schematic illustration of a process microchannel that may be used with the inventive process, the process microchannel containing a catalyst having a flow-through configuration.

The solid catalyst may have any size and geometric configuration that fits within the process microchannels. The catalyst may be in the form of particulate solids (e.g., pellets, powder, fibers, and the like) having a median particle diameter of about 1 to about 1000 μm, and in one embodiment about 10 to about 500 μm, and in one embodiment about 25 to about 250 μm. The catalyst may be mixed with the first reactant, as indicated above, and flow through the process microchannel with the reactants. In one embodiment, the catalyst may be in the form of a fixed bed of particulate solids such as illustrated in FIG. 20. Referring to FIG. 20, the catalyst 800 is contained within process microchannel 802. The reactants flow through the catalyst bed as indicated by arrows 804 and 806.

The catalyst may be supported on a porous support structure such as a foam, felt, wad or a combination thereof. The term "foam" is used herein to refer to a structure with continuous walls defining pores throughout the structure. The term "felt" is used herein to refer to a structure of fibers with interstitial spaces therebetween. The term "wad" is used herein to refer to a support having a structure of tangled strands, like steel wool. The catalyst may be supported on a support having a honeycomb structure or a serpentine configuration.

The catalyst may be supported on a flow-by support structure such as a felt with an adjacent gap, a foam with an adjacent gap, a fin structure with gaps, a washcoat on any inserted substrate, or a gauze that is parallel to the flow direction with a corresponding gap for flow. An example of a flow-by structure is illustrated in FIG. 21. In FIG. 21 the catalyst 810 is contained within process microchannel 812. An open passage way 814 permits the flow of the reactants through the process microchannel 812 in contact with the catalyst 810 as indicated by arrows 816 and 818.

The catalyst may be supported on a flow-through support structure such as a foam, wad, pellet, powder, or gauze. An example of a flow-through structure is illustrated in FIG. 22. In FIG. 22, the flow-through catalyst 820 is contained within process microchannel 822 and the reactants flow through the catalyst 820 as indicated by arrows 824 and 826.

The support may be formed from a material comprising silica gel, foamed copper, sintered stainless steel fiber, steel wool, alumina, poly(methyl methacrylate), polysulfonate, poly(tetrafluoroethylene), iron, nickel sponge, nylon, polyvinylidene difluoride, polypropylene, polyethylene, polyethylene ethylketone, polyvinyl alcohol, polyvinyl acetate, polyacrylate, polymethylmethacrylate, polystyrene, polyphenylene sulfide, polysulfone, polybutylene, or a combination of two or more thereof. In one embodiment, the support structure may be made of a heat conducting material, such as a metal, to enhance the transfer of heat away from the catalyst.

The catalyst may be directly washcoated on the interior walls of the process microchannels, grown on the walls from solution, or coated in situ on a fin structure. The catalyst may be in the form of a single piece of porous contiguous material, or many pieces in physical contact. In one embodiment, the catalyst may comprise a contiguous material and have a contiguous porosity such that molecules can diffuse through the catalyst. In this embodiment, the fluids may flow through the catalyst rather than around it. In one embodiment, the cross-sectional area of the catalyst may occupy from about 1 to about 99%, and in one embodiment from about 10 to about 95% of the cross-sectional area of the process microchannels. The catalyst may have a surface area, as measured by BET, of greater than about 0.5 m$^2$/g, and in one embodiment greater than about 2 m$^2$/g, and in one embodiment greater than about 5 m$^2$/g, and in one embodiment greater than about 10 m$^2$/g, and in one embodiment greater than about 25 m$^2$/g, and in one embodiment greater than about 50 m$^2$/g.

The catalyst may comprise a porous support, an interfacial layer overlying the porous support, and a catalyst material dispersed or deposited on the interfacial layer. The interfacial layer may be solution deposited on the support or it may be deposited by chemical vapor deposition or physical vapor deposition. In one embodiment the catalyst comprises a porous support, optionally a buffer layer overlying the support, an interfacial layer overlying the support or the optional buffer layer, and a catalyst material dispersed or deposited on the interfacial layer. Any of the foregoing layers may be continuous or discontinuous as in the form of spots or dots, or in the form of a layer with gaps or holes.

The porous support may have a porosity of at least about 5% as measured by mercury porosimetry and an average pore size (sum of pore diameters divided by number of pores) of about 1 to about 1000 μm. The porous support may be made of any of the above indicated materials identified as being useful in making a support structure. The porous support may comprise a porous ceramic support or a metal foam. Other porous supports that may be used include carbides, nitrides, and composite materials. The porous support may have a porosity of about 30% to about 99%, and in one embodiment about 60% to about 98%. The porous support may be in the form of a foam, felt, wad, or a combination thereof. The open cells of the metal foam may range from about 20 pores per inch (ppi) to about 3000 ppi, and in one embodiment about 20 to about 1000 ppi, and in one embodiment about 40 to about 120 ppi. The term "ppi" refers to the largest number of pores per inch (in isotropic materials the direction of the measurement is irrelevant; however, in anisotropic materials, the measurement is done in the direction that maximizes pore number).

The buffer layer, when present, may have a different composition and/or density than both the porous support and the interfacial layers, and in one embodiment has a coefficient of thermal expansion that is intermediate the thermal expansion coefficients of the porous support and the interfacial layer. The buffer layer may be a metal oxide or metal carbide. The buffer layer may be comprised of $Al_2O_3$, $TiO_2$, $SiO_2$, $ZrO_2$, or combination thereof. The $Al_2O_3$ may be $\alpha$-$Al_2O_3$, $\gamma$-$Al_2O_3$ or a combination thereof. $\alpha$-$Al_2O_3$ provides the advantage of excellent resistance to oxygen diffusion. The buffer layer may be formed of two or more compositionally different sublayers. For example, when the porous support is metal, for example a stainless steel foam, a buffer layer formed of two compositionally different sub-layers may be used. The first sublayer (in contact with the porous support) may be $TiO_2$. The second sublayer may be $\alpha$-$Al_2O_3$ which is placed upon the $TiO_2$. In one embodiment, the $\alpha$-$Al_2O_3$ sublayer is a dense layer that provides protection of the underlying metal surface. A less dense, high surface area interfacial layer such as alumina may then be deposited as support for a catalytically active layer.

The porous support may have a thermal coefficient of expansion different from that of the interfacial layer. In such a case a buffer layer may be needed to transition between the two coefficients of thermal expansion. The thermal expansion coefficient of the buffer layer can be tailored by controlling its composition to obtain an expansion coefficient that is compatible with the expansion coefficients of the porous support and interfacial layers. The buffer layer should be free of openings and pin holes to provide superior protection of the underlying support. The buffer layer may be nonporous. The buffer layer may have a thickness that is less than one half of the average pore size of the porous support. The buffer layer may have a thickness of about 0.05 to about 10 μm, and in one embodiment about 0.05 to about 5 μm.

In one embodiment of the invention, adequate adhesion and chemical stability may be obtained without a buffer layer. In this embodiment the buffer layer may be omitted.

The interfacial layer may comprise nitrides, carbides, sulfides, halides, metal oxides, carbon, or a combination thereof. The interfacial layer provides high surface area and/or provides a desirable catalyst-support interaction for supported catalysts. The interfacial layer may be comprised of any material that is conventionally used as a catalyst support. The interfacial layer may be comprised of a metal oxide. Examples of metal oxides that may be used include $\gamma$-$Al_2O_3$, $SiO_2$, $ZrO_2$, $TiO_2$, tungsten oxide, magnesium oxide, vanadium oxide, chromium oxide, manganese oxide, iron oxide, nickel oxide, cobalt oxide, copper oxide, zinc oxide, molybdenum oxide, tin oxide, calcium oxide, aluminum oxide, lanthanum series oxide(s), zeolite(s) and combinations thereof. The interfacial layer may serve as a catalytically active layer without any further catalytically active material deposited thereon. Usually, however, the interfacial layer is used in combination with a catalytically active layer. The interfacial layer may also be formed of two or more compositionally different sublayers. The interfacial layer may have a thickness that is less than one half of the average pore size of the porous support. The interfacial layer thickness may range from about 0.5 to about 100 µm, and in one embodiment from about 1 to about 50 µm. The interfacial layer may be either crystalline or amorphous. The interfacial layer may have a BET surface area of at least about 1 $m^2$/g.

The catalyst may be deposited on the interfacial layer. Alternatively, the catalyst material may be simultaneously deposited with the interfacial layer. The catalyst layer may be intimately dispersed on the interfacial layer. That the catalyst layer is "dispersed on" or "deposited on" the interfacial layer includes the conventional understanding that microscopic catalyst particles are dispersed: on the support layer (i.e., interfacial layer) surface, in crevices in the support layer, and in open pores in the support layer.

Figures 23, 24:
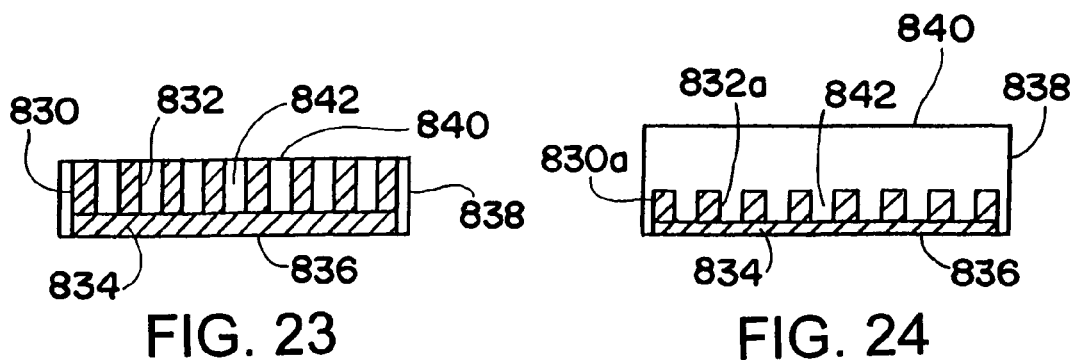
FIG. 23 is a schematic illustration of a process microchannel that may be used in the inventive process, the process microchannel containing a fin assembly comprising a plurality of fins, a catalyst being supported by the fins.
FIG. 24 illustrates an alternate embodiment of the process microchannel and fin assembly illustrated in FIG. 23.

The catalyst may be supported on an assembly of one or more fins positioned within the process microchannels. Examples are illustrated in FIGS. 23-25. Referring to FIG. 23, fin assembly 830 includes fins 832 which are mounted on fin support 834 which overlies base wall 836 of process microchannel 838. The fins 832 project from the fin support 834 into the interior of the process microchannel 838. The fins 832 extend to the interior surface of upper wall 840 of process microchannel 838. Fin channels 842 between the fins 832 provide passage ways for fluid to flow through the process microchannel 838 parallel to its length. Each of the fins 832 has an exterior surface on each of its sides, this exterior surface provides a support base for the catalyst. With the inventive process, the reactants flow through the fin channels 842, contact the catalyst supported on the exterior surface of the fins 832, and react to form the product. The fin assembly 830a illustrated in FIG. 24 is similar to the fin assembly 830 illustrated in FIG. 23 except that the fins 832a do not extend all the way to the interior surface of the upper wall 840 of the microchannel 838. The fin assembly 830b illustrated in FIG. 25 is similar to the fin assembly 830 illustrated in FIG. 23 except that the fins 832b in the fin assembly 830b have cross sectional shapes in the form of trapezoids. Each of the fins (832, 832a, 832b) may have a height ranging from about 0.02 mm up to the height of the process microchannel 838, and in one embodiment from about 0.02 to about 10 mm, and in one embodiment from about 0.02 to about 5 mm, and in one embodiment from about 0.02 to about 2 mm. The width of each fin (832, 832a, 832b) may range from about 0.02 to about 5 mm, and in one embodiment about 0.02 to about 2 mm and in one embodiment about 0.02 to about 1 mm. The length of each fin (832, 832a, 832b) may be of any length up to the length of the process microchannel 838, and in one embodiment up to about 10 m, and in one embodiment about 1 cm to about 10 m, and in one embodiment about 1 cm to about 5 m, and in one embodiment about 1 cm to about 2.5 m. The gap between each of the fins (832, 832a, 832b) may be of any value and may range from about 0.02 to about 5 mm, and in one embodiment from about 0.02 to about 2 mm, and in one embodiment from about 0.02 to about 1 mm. The number of fins (832, 832a, 832b) in the process microchannel 838 may range from about 1 to about 50 fins per centimeter of width of the process microchannel 888, and in one embodiment from about 1 to about 30 fins per centimeter, and in one embodiment from about 1 to about 10 fins per centimeter, and in one embodiment from about 1 to about 5 fins per centimeter, and in one embodiment from about 1 to about 3 fins per centimeter. As indicated above, each of the fins may have a cross-section in the form of a rectangle or square as illustrated in FIG. 23 or 24, or a trapezoid as illustrated in FIG. 25. When viewed along its length, each fin (832, 832a, 832b) may be straight, tapered or have a serpentine configuration. The fin assembly (830, 830a, 830b) may be made of any material that provides sufficient strength, dimensional stability and heat transfer characteristics to permit operation for which the process microchannel is intended. These materials include: steel (e.g., stainless steel, carbon steel, and the like); monel; inconel; aluminum; titanium; nickel; platinum; rhodium; copper; chromium; brass; alloys of any of the foregoing metals; polymers (e.g., thermoset resins); ceramics; glass; composites comprising one or more polymers (e.g., thermoset resins) and fiberglass; quartz; silicon; or a combination of two or more thereof. The fin assembly (830, 830a, 830b) may be made of an $Al_2O_3$ forming material such as an alloy comprising Fe, Cr, Al and Y, or a $Cr_2O_3$ forming material such as an alloy of Ni, Cr and Fe, In one embodiment, the reaction zone (212, 312, 413, 515, 525, 535, 545, 615, 944, 954, 955, 964, 964A, 973, 973A) in the process microchannel (210, 310, 410, 510, 520, 530, 540, 610, 940, 950, 960, 960A, 972, 972A) may be characterized by having a bulk flow path. The term "bulk flow path" refers to an open path (contiguous bulk flow region) within the process microchannels. A contiguous bulk flow region allows rapid fluid flow through the microchannels without large pressure drops. In one embodiment, the flow of fluid in the bulk flow region is laminar. Bulk flow regions within each process microchannel (210, 310, 410, 510, 520, 530, 540, 610, 940, 950, 960, 960A, 972, 972A) may have a cross-sectional area of about 0.05 to about 10,000 $mm^2$, and in one embodiment about 0.05 to about 5000 $mm^2$, and in one embodiment about 0.1 to about 2500 $mm^2$. The bulk flow regions may comprise from about 5% to about 95%, and in one embodiment about 30% to about 80% of the cross-section of the process microchannels.

In one embodiment of the invention relatively short contact times, high selectivity to the desired product and relatively low rates of deactivation of the catalyst may be achieved by limiting the diffusion path required for the catalyst. For example, this may be achieved when the catalyst is in the form of a thin layer on an engineered support such as a metallic foam or on the wall of the process microchannel. This allows for increased space velocities. In one embodiment, the thin layer of catalyst can be produced using chemical vapor deposition. This thin layer may have a thickness in the range up to about 1 micron, and in one embodiment from about 0.1 to about 1 micron, and in one embodiment about 0.25 micron. These thin layers may reduce the time the reactants are within the active catalyst structure by reducing the diffusional path. This decreases the time the reactants spend in the active portion of the catalyst. The result may be increased selectivity to the product and reduced unwanted by-products. An advantage of this mode of catalyst deployment is that, unlike conventional catalysts in which the active portion of the catalyst may be bound up in an inert low thermal conductivity binder, the active catalyst film is in intimate contact with either the engineered structure or the wall of the process microchannel. This may leverage high heat transfer rates attainable in the microchannel reactor and allows for close control of temperature. The result is the ability to operate at increased temperature (faster kinetics) without promoting the formation of undesired by-products, thus producing higher productivity and yield and prolonging catalyst life.

In one embodiment, the catalyst may be regenerated. This may be done by flowing a regenerating fluid through the process microchannels (210, 310, 410, 510, 520, 530, 540, 610, 940, 950, 960, 960A, 972, 972A) in contact with the catalyst. The regenerating fluid may comprise hydrogen or a diluted hydrogen stream. The diluent may comprise nitrogen, argon, steam, methane, carbon dioxide, or a mixture of two or more thereof. The concentration of $H_2$ in the regenerating fluid may range up to about 100% by volume, and in one embodiment from about 1 to about 100% by volume, and in one embodiment from about 1 to about 50% volume. The regenerating fluid may flow from the header 104 through the process microchannels to the footer 106, or in the opposite direction from the footer 106 through the process microchannels to the header 104. The temperature of the regenerating fluid may be from about 20 to about 600° C., and in one embodiment about 20 to about 400° C., and in one embodiment about 80 to about 200° C. The pressure within the process microchannels (210, 310, 410, 510, 520, 530, 540, 610, 940, 950, 960, 960A, 972, 972A) during this regeneration step may range from about 1 to about 100 atmospheres absolute pressure, and in one embodiment about 1 to about 10 atmospheres. The residence time for the regenerating fluid in the process microchannels may range from about 0.001 to about 10 seconds, and in one embodiment about 0.01 second to about 1 second.

The contact time of the reactants and product with the catalyst within the process microchannels (210, 310, 410, 510, 520, 530, 540, 610, 940, 950, 960, 960A, 972, 972A) may be in the range up to about 100 seconds, and in one embodiment in the range from about 1 millisecond (ms) to about 100 seconds, and in one embodiment in the range from about 1 ms to about 50 seconds, and in one embodiment in the range from about 1 ms to about 25 seconds, and in one embodiment in the range from about 1 ms to about 10 seconds, and in one embodiment from about 1 ms to about 1 second, and in one embodiment from about 1 ms to about 500 ms, and in one embodiment about 1 ms to about 200 ms, and in one embodiment about 1 ms to about 100 ms, and in one embodiment about 1 ms to about 50 ms, and in one embodiment about 1 ms to about 20 ms, and in one embodiment about 1 ms to about 10 ms.

The flow rate of fluid flowing in the process microchannels (210, 310, 410, 510, 520, 530, 540, 610, 940, 950, 960, 960A, 972, 972A) may be in the range from about 0.001 to about 500 lpm, and in one embodiment about 0.001 to about 250 lpm, and in one embodiment about 0.001 to about 100 lpm, and in one embodiment about 0.001 to about 50 lpm, and in one embodiment about 0.001 to about 25 lpm, and in one embodiment about 0.01 to about 10 lpm. The velocity of fluid flowing in the process microchannels may be in the range from about 0.01 to about 200 m/s, and in one embodiment about 0.01 to about 75 m/s, and in one embodiment about 0.01 to about 50 m/s, and in one embodiment about 0.01 to about 30 m/s, and in one embodiment about 0.02 to about 20 m/s. The Reynolds Number for the fluid flowing in the process microchannels may be in the range from about 0.0001 to about 100000, and in one embodiment about 0.001 to about 10000.

The weight hourly space velocity (WHSV) for the flow of the reactants and product in the microchannel reactor core 102 may be at least about 0.1 (ml feed)/(g catalyst) (hr). The WHSV may range from about 0.1 to about 5000, and in one embodiment, the WHSV may range from about 1 to about 500 (ml feed)/(g catalyst) (hr), and in one embodiment the WHSV may be in the range from about 10 to about 500 (ml feed)/(g catalyst) (hr).

While not wishing to be bound by theory, it is believed that a high superficial velocity in the process microchannels may be advantageous for reactions wherein both gas and liquid phases are present during the reaction. This is because the shear stress force of the fluid may act to thin liquid layers that typically form on the surface of the catalyst. Thinner liquid film layers may reduce the mass transfer resistance of the reactants to the catalyst surface and improve conversion at relatively short contact times for the reactants, for example, contact times less than about 500 milliseconds. In one embodiment, the superficial velocity for the fluids flowing through the process microchannels may be at least about 0.01 meters per second (m/s), and in one embodiment in the range from about 0.01 to about 50 m/s, and in one embodiment in the range from about 0.01 to about 10 m/s, and in one embodiment in the range from about 0.01 to about 1 m/s, and in one embodiment in the range from about 0.05 to about 0.5 m/s.

The temperature of the reactants entering the microchannel reactor (100, 900, 900A, 990) or reactor core (102, 902) may be in the range from about −40° C. to about 400° C., and in one embodiment about 0° C. to about 400° C., and in one embodiment from about 20° C. to about 300° C., and in one embodiment from about 20° C. to about 250° C., and in one embodiment from about 20° C. to about 200° C.

The temperature within the process microchannels may be in the range from about −40° C. to about 400° C., and in one embodiment from about 0° C. to about 400° C., and in one embodiment from about 20° C. to about 300° C., and in one embodiment from about 20° C. to about 250° C., and in one embodiment from about 20° C. to about 200° C.

The temperature of the product exiting the microchannel reactor (100, 900, 900A, 990) or reactor core (102, 902) may be in the range from about −40° C. to about 400° C., and in one embodiment about 0° C. to about 400° C., and in one embodiment from about 20° C. to about 300° C., and in one embodiment from about 20° C. to about 250° C., and in one embodiment from about 20° C. to about 200° C.

The pressure within the process microchannels may be in the range up to about 50 atmospheres absolute pressure, and in one embodiment up to about 40 atmospheres, and in one embodiment up to about 30 atmospheres. In one embodiment the pressure may be in the range from about 1 to about 50 atmospheres absolute pressure, and in one embodiment from about 10 to about 40 atmospheres, and in one embodiment from about 20 to about 30 atmospheres.

The pressure drop of the reactants and/or products as they flow in the process microchannels may be in the range up to about 1 atmosphere per meter of length of the process microchannel (atm/m), and in one embodiment up to about 0.5 atm/m, and in one embodiment up to about 0.1 atm/m.

The pressure drop for the second reactant flowing through the apertured sections (250, 350, 370, 440, 440a, 511, 521, 531, 541, 640, 650, 660, 670, 923, 925, 923A, 925A, 974, 974A) may be in the range up to about 0.1 atm, and in one embodiment from about 0.001 to about 0.1 atm, and in one embodiment from about 0.001 to about 0.05 atm, and in one embodiment about 0.001 to about 0.005 atm. The reactants and products flowing through the process microchannels may be in the form of a vapor, a liquid, or a mixture of vapor and liquid. The Reynolds Number for the flow of vapor through the process microchannels may be in the range from about 10 to about 10000, and in one embodiment about 100 to about 3000. The Reynolds Number for the flow of liquid through the process microchannels may be about 10 to about 10000, and in one embodiment about 100 to about 3000.

The conversion of the first reactant may be in the range from about 5% or higher per cycle, and in one embodiment from about 15 to about 100%.

The conversion of the second reactant may be in the range from about 25% or higher per cycle, and in one embodiment from about 25 to about 100% per cycle.

The yield of product may be in the range from about 20% or higher per cycle, and in one embodiment from about 20 to about 50% per cycle.

EXAMPLE 1

A microchannel reactor comprising an acrylic process microchannel having a rectangular cross-section and internal dimensions of 0.040×1.25×3 inches (1.02×31.75×76.2 mm) is constructed. The process microchannel has an apertured section in one of its sidewalls. The apertured section has a nominal aperture or pore size of 0.1 micron and the dimensions of 0.010×1×1.5 inches (0.254×25.4×38.1 mm). The apertured section is constructed of stainless steel 316 L and is supplied by Mott Corporation of Farmington, Conn. under Catalogue No. 1110-12-12-018-01-A. The apertured section is connected to a gas distribution plenum and tubing to permit the flow of gas through the apertured section into the process microchannel. The catalyst, which is palladium black and is in the form of nanosized particles, is dispersed using carbon black as a dispersing/binding agent on the interior walls of the process microchannel. The process microchannel is connected to tubing to permit the flow of liquid through the process microchannel. The gas flows through the apertured section into the process microchannel in contact with the liquid flowing through the process microchannel. As the gas flows through the apertures of the apertured section, it forms bubbles in the liquid in the process microchannel. The process is conducted using hydrogen as the gas and unsaturated vegetable oil as the liquid. The flow rate of the hydrogen is 5 standard cubic centimeters per minute (SCCM) and the flow rate of the vegetable oil is 60 milliliters per minute (ml/min). The temperature is 25° C. Bubbles of hydrogen having diameters in the range of 5 to 25 microns are formed in the vegetable oil. The hydrogen reacts with the vegetable oil to form margarine.

While the invention has been explained in relation to various embodiments, it is to be understood that various modifications thereof will become apparent to those skilled in the art upon reading the specification. Therefore, it is to be understood that the invention disclosed herein is intended to cover such modifications as fall within the scope of the appended claims.

The invention claimed is:

1. A process for conducting a multiphase reaction in a process microchannel, comprising:
    forming a multiphase reaction mixture in the process microchannel, the multiphase reaction mixture comprising a first reactant and a second reactant; the first reactant comprising at least one liquid; the second reactant comprising at least one gas, at least one liquid, or a combination of at least one gas and at least one liquid; the first reactant forming a continuous phase in the multiphase reaction mixture; the second reactant forming gas bubbles and/or liquid droplets dispersed in the continuous phase;
    reacting the first reactant with the second reactant in the process microchannel in the presence of at least one catalyst to form at least one product; and
    exchanging heat between the process microchannel and a heat exchange channel;
    wherein a second reactant stream channel is positioned adjacent to the process microchannel, the process microchannel having a first reactant entry point for the first reactant, the first reactant flowing through the first reactant entry point into the process microchannel and the second reactant flowing from the second reactant stream channel through the second reactant introduction points into the process microchannel, the first reactant contacting the second reactant in the process microchannel to form the multiphase reaction mixture.

2. The process of claim 1 wherein the gas bubbles and/or liquid droplets have a volume-based mean diameter in the range of about 0.1 to about 100 microns, and a span in the range from about 1 to about 10.

3. The process of claim 1 wherein the process microchannel comprises at least one side wall and at least one apertured section extending along at least part of the axial length of the side wall, the second reactant flowing through the apertured section into the process microchannel in contact with the first reactant to form the multiphase reaction mixture.

4. The process of claim 1 wherein the process is conducted in a microchannel reactor, the microchannel reactor comprising a plurality of the process microchannels, a plurality of the second reactant stream channels and at least one header for distributing the first reactants to the process microchannels and the second reactant to the second reactant stream channels.

5. The process of claim 1 wherein a reaction zone is in the process microchannel, the second reactant contacting the first reactant in the reaction zone to form the multiphase reaction mixture.

6. The process of claim 1 wherein a mixing zone and a reaction zone are in the process microchannel, the mixing zone being upstream of the reaction zone, the second reactant contacting the first reactant in the mixing zone to form the multiphase reaction mixture.

7. The process of claim 1 wherein a mixing zone and a reaction zone are in the process microchannel, the mixing zone being upstream of the reaction zone, the second reactant contacting the first reactant to form the multiphase reaction mixture, part of the second reactant contacting the first reactant in the mixing zone, and part of the second reactant contacting the first reactant in the reaction zone.

8. The process of claim 1 wherein the process microchannel contains two or more reaction zones.

9. The process of claim 1 wherein the process microchannel has an internal dimension of width or height of up to about 10 mm.

10. The process of claim 1 wherein the process microchannel has an internal dimension of width or height of up to about 2 mm.

11. The process of claim 1 wherein the process microchannel is made of a material comprising: aluminum; titanium; nickel; copper; an alloy of any of the foregoing metals; steel; monel; inconel; brass; a polymer; ceramics; glass; a composite comprising a polymer and fiberglass; quartz; silicon; or a combination of two or more thereof.

12. The process of claim 1 wherein the second reactant stream channel has an internal dimension of width or height of up to about 10 mm.

13. The process of claim 1 wherein the second reactant stream channel has an internal dimension of width or height of up to about 2 mm.

14. The process of claim 1 wherein the second reactant stream channel is made of a material comprising: aluminum; titanium; nickel; copper; an alloy of any of the foregoing metals; steel; monel; inconel; brass; a polymer; ceramics; glass; a composite comprising a polymer and fiberglass; quartz; silicon; or a combination of two or more thereof.

15. The process of claim 3 wherein the apertured section comprises a relatively thin sheet overlying a relatively thick sheet or plate, the relatively thin sheet containing an array of relatively small apertures, and the relatively thick sheet or plate containing an array of relatively large apertures, at least some of the relatively small apertures being aligned with the relatively large apertures.

16. The process of claim 3 wherein the apertured section comprises apertures that are partially filled with a coating material.

17. The process of claim 3 wherein the apertured section is heat treated.

18. The process of claim 3 wherein the apertured section is made from a porous material.

19. The process of claim 18 wherein the porous material is metallic, nonmetallic and/or oxidized.

20. The process of claim 18 wherein the porous material is coated with alumina or nickel.

21. The process of claim 3 wherein the apertured section is made from a porous material, the surface of the porous material being treated by filling the pores on the surface with a liquid filler, solidifying the filler, grinding or polishing the surface, and removing the filler.

22. The process of claim 3 wherein the apertured section extends along about 5% to about 100% of the axial length of the process microchannel.

23. The process of claim 1 wherein the heat exchange channel is adjacent to the process microchannel.

24. The process of claim 1 wherein the heat exchange channel is remote from the process microchannel.

25. The process of claim 1 wherein the heat exchange channel comprises a microchannel.

26. The process of claim 1 wherein the heat exchange channel has an internal dimension of width or height of up to about 10 mm.

27. The process of claim 1 wherein the heat exchange channel has an internal dimension of width or height of up to about 2 mm.

28. The process of claim 1 wherein the heat exchange channel is made of a material comprising: aluminum; titanium; nickel; copper; an alloy of any of the foregoing metals; steel; monel; inconel; brass; a polymer; ceramics; glass; a composite comprising polymer and fiberglass; quartz; silicon; or a combination of two or more thereof.

29. The process of claim 1 wherein the process microchannel comprises surface features formed in and/or on one or more interior walls for modifying flow and/or mixing within the process microchannel.

30. The process of claim 1 wherein the second reactant stream channel comprises surface features formed in and/or on one or more interior walls for modifying flow and/or mixing within the channel.

31. The process of claim 1 wherein the heat exchange channel comprises surface features formed in and/or on one or more interior walls for modifying flow and/or mixing within the heat exchange channel.

32. The process of claim 29 wherein the surface features are in the form of depressions in and/or projections from one or more of the microchannel interior walls that are oriented at angles relative to the direction of flow of fluid through the process microchannel.

33. The process of claim 29 wherein the surface features comprise at least two surface feature regions where mixing of the first reactant and second reactant is conducted in a first surface feature region followed by flow in a second surface feature region where the flow pattern in the second surface feature region is different than the flow pattern in the first surface feature region.

34. The process of claim 33 wherein a reaction mixture comprising one or more unreacted reactants and the product is formed in the first surface feature region and flows in the second surface feature region where one or more of the unreacted reactants and/or the product is separated from the reaction mixture.

35. The process of claim 3 wherein the apertured section comprises an interior portion that forms part of one or more of the interior walls of the process microchannel and a surface feature sheet overlies the interior portion of the apertured section, and wherein surface features are in and/or on the surface feature sheet.

36. The process of claim 1 wherein particulate solids in the form of a fluidized bed are in the process microchannel, the process microchannel comprising surface features formed in and/or on one or more of its interior walls for modifying flow and/or mixing within the process microchannel.

37. The process of claim 29 wherein the surface features comprise two or more layers stacked on top of each other and/or intertwined in a three-dimensional pattern.

38. The process of claim 29 wherein the surface features are in the form of circles, oblongs, squares, rectangles, checks, chevrons, wavy shapes, or combinations thereof.

39. The process of claim 29 wherein the surface features comprise sub-features where the major walls of the surface features further contain smaller surface features in the form of notches, waves, indents, holes, burrs, checks, scallops, or combinations thereof.

40. The process of claim 1 wherein the temperature of the first reactant entering the process microchannel is within about 200° C. of the temperature of the product exiting the process microchannel.

41. The process of claim 1 wherein a heat exchange fluid is in the heat exchange channel.

42. The process of claim 41 wherein the heat exchange fluid undergoes a phase change in the heat exchange channel.

43. The process of claim 1 wherein the heat flux between the heat exchange channel and the process microchannel is in the range from about 0.01 to about 250 watts per square centimeter of surface area of the process microchannel.

44. The process of claim 1 wherein an endothermic process is conducted in the heat exchange channel.

45. The process of claim 1 wherein an exothermic process is conducted in the heat exchange channel.

46. The process of claim 1 wherein the multiphase reaction mixture flows in the process microchannel in a first direction, and a heat exchange fluid flows in the heat exchange channel in a second direction, the second direction being cross current relative to the first direction.

47. The process of claim 1 wherein the multiphase reaction mixture flows in the process microchannel in a first direction, and a heat exchange fluid flows in the heat exchange channel in a second direction, the second direction being cocurrent or counter current relative to the first direction.

48. The process of claim 1 wherein a heat exchange fluid is in the heat exchange channel, the heat exchange fluid comprising the first reactant, the second reactant, the multiphase reaction mixture, the product, or a mixture of two or more thereof.

49. The process of claim 1 wherein a heat exchange fluid is in the heat exchange channel, the heat exchange fluid comprising one or more of air, steam, liquid water, carbon monoxide, carbon dioxide, gaseous nitrogen, liquid nitrogen, inert gas, gaseous hydrocarbon, oil, and liquid hydrocarbon.

50. The process of claim 1 wherein the catalyst comprises at least one oxidation catalyst, hydrocracking catalyst, hydrogenation catalyst, hydration catalyst, carbonylation catalyst, sulfation catalyst, sulfonation catalyst, oligomerization catalyst, polymerization catalyst, or a combination of two or more thereof.

51. The process of claim 1 wherein the catalyst comprises particulate solids.

52. The process of claim 1 wherein the catalyst is on at least one interior wall of the process microchannel.

53. The process of claim 1 wherein the catalyst is supported by a support.

54. The process of claim 53 wherein the support is made of a material comprising one or more of silica gel, foamed copper, sintered stainless steel fiber, steel wool, alumina, poly(methyl methacrylate), polysulfonate, poly(tetrafluoroethylene), iron, nickel sponge, nylon, polyvinylidene difluoride, polypropylene, polyethylene, polyethylene ethylketone, polyvinyl alcohol, polyvinyl acetate, polyacrylate, polymethylmethacrylate, polystyrene, polyphenylene sulfide, polysulfone, polybutylene, or a combination of two or more thereof.

55. The process of claim 53 wherein the support comprises a heat conducting material.

56. The process of claim 53 wherein the support comprises an alloy comprising Ni, Cr and Fe, or an alloy comprising Fe, Cr, Al and Y.

57. The process of claim 53 wherein the support has a flow-by configuration, a flow-through configuration, a honeycomb structure or a serpentine configuration.

58. The process of claim 53 wherein the support has the configuration of a foam, felt, wad, fin, or a combination of two or more thereof.

59. The process of claim 53 wherein the support has a flow-by configuration with an adjacent gap, a foam configuration with an adjacent gap, a fin structure with gaps or a gauze configuration with a gap for flow.

60. The process of claim 53 wherein the catalyst is washcoated on at least one interior wall of the process microchannel and/or the support.

61. The process of claim 53 wherein the support comprises a fin assembly comprising at least one fin.

62. The process of claim 61 wherein the fin assembly comprises a plurality of parallel spaced fins.

63. The process of claim 61 wherein the fin has an exterior surface and a porous material overlies at least part of the exterior surface of the fin, the catalyst being supported by the porous material.

64. The process of claim 61 wherein the porous material comprises one or more of a coating, fibers, foam or felt.

65. The process of claim 61 wherein the fin has an exterior surface and a plurality fibers or protrusions extend from at least part of the exterior surface of the fin, the catalyst being supported by the protrusions.

66. The process of claim 61 wherein the fin has an exterior surface and the catalyst is: washcoated on at least part of the exterior surface of the fin; grown on at least part of the exterior surface of the fin from solution; or deposited on at least part of the exterior surface of the fin using vapor deposition.

67. The process of claim 61 wherein the fin assembly comprises a plurality of parallel spaced fins, at least one of the fins having a length that is different than the length of the other fins.

68. The process of claim 61 wherein the fin assembly comprises a plurality of parallel spaced fins, at least one of the fins having a height that is different than the height of the other fins.

69. The process of claim 61 wherein the fin has a cross section having the shape of a square, a rectangle, or a trapezoid.

70. The process of claim 61 wherein the fin is made of a material comprising: steel; aluminum; titanium; iron; nickel; platinum; rhodium; copper; chromium; brass; an alloy of any of the foregoing metals; a polymer; ceramics; glass; a composite comprising polymer and fiberglass; quartz; silicon; or a combination of two or more thereof.

71. The process of claim 61 wherein the fin is made of a material comprising Ni, Cr and Fe, or a material comprising Fe, Cr, Al and Y.

72. The process of claim 61 wherein the fin is made of an $Al_2O_3$ forming material or a $Cr_2O_3$ forming material.

73. The process of claim 1 wherein the catalyst is in a reaction zone in the process microchannel, the reaction zone comprising a bulk flow path comprising about 5% to about 95% of the cross section of the process microchannel.

74. The process of claim 1 wherein the catalyst comprises a liquid.

75. The process of claim 74 wherein the catalyst is mixed with the first reactant.

76. The process of claim 74 wherein the catalyst is mixed with the second reactant.

77. The process of claim 1 wherein first reactant comprises a vegetable oil, the second reactant comprises hydrogen, and the reaction is a hydrogenation reaction.

78. The process of claim 1 wherein the reaction between the first reactant and the second reactant comprises a hydrogenation reaction.

79. The process of claim 1 wherein the reaction between the first reactant and the second reactant is a hydrogenation reaction wherein the formation of trans isomers is less than about 15% by weight.

80. The process of claim 1 wherein the contact time for the reactants, and product with the catalyst is in the range up to about 100 seconds.

81. The process of claim 1 wherein the temperature within the process microchannel is in the range from about −40° C. to about 400° C.

82. The process of claim 1 wherein the pressure within the process microchannel is in the range up to about 50 atmospheres absolute pressure.

83. The process of claim 1 wherein the weight hourly space velocity for the flow of reactants and product through the process microchannel is at least about 0.1 (ml feed)/(g catalyst)(hr).

84. The process of claim 1 wherein the pressure drop for the flow of reactants and product through the process microchannel is up to about 1 atmosphere per meter of length of the process microchannel.

85. The process of claim 1 wherein a heat exchange fluid flows in the heat exchange channel, the pressure drop for the heat exchange fluid flowing in the heat exchange channel being up to about 1 atmosphere per meter of length of the heat exchange channel.

86. The process of claim 1 wherein the conversion of the first reactant is about 5% or higher per cycle.

87. The process of claim 1 wherein the conversion of the second reactant is about 25% or higher per cycle.

88. The process of claim 1 wherein the yield of product is about 20% or higher per cycle.

89. The process of claim 1 wherein the product is removed from the process microchannel, the process further comprises flowing a regenerating fluid through the process microchannel in contact with the catalyst.

90. The process of claim 1 wherein the reactants and product comprise fluids and the superficial velocity of the fluids flowing in the process microchannel is at least about 0.01 meter per second.

91. The process of claim 5 wherein surface features are positioned in the reaction zone for modifying the flow of the reactants and/or enhancing the mixing of the reactants.

92. The process of claim 6 wherein surface features are positioned in the mixing zone and/or reaction zone for modifying the flow of the reactants and/or enhancing the mixing of the reactants.

93. The process of claim 1 wherein two or more process microchannels exchange heat with the heat exchange channel.

94. The process of claim 3 wherein the apertured section comprises two or more discrete feed introduction points along the axial length of the apertured section.

95. The process of claim 1 wherein the multiphase reaction mixture further comprises particulate solids.

96. The process of claim 1 wherein the multiphase reaction mixture comprises a foam.

97. The process of claim 1 wherein the multiphase reaction mixture further comprise one or more solvents.

98. The process of claim 34 wherein the second surface feature region is positioned within the interior of the process microchannel and another second reactant is combined with the multiphase reaction mixture downstream of the second surface feature region, and another reaction is conducted within the process microchannel downstream of the second surface feature region.

99. The process of claim 1 wherein the design of the process microchannel varies along the axial length of the process microchannel.

100. The process of claim 5 wherein a capillary structure or pore throat is in the process microchannel downstream of the reaction zone and is used to separate gas from liquid.

101. A process for conducting a multiphase reaction comprising:
flowing at least one first reactant in a process microchannel, the first reactant comprising at least one liquid, a second reactant stream channel being positioned adjacent to the process microchannel, the process microchannel and the second reactant stream channel having a common wall, a plurality of second reactant introduction points being positioned in the common wall;
flowing at least one second reactant from the second reactant stream channel through the second reactant introduction points into the process microchannel in contact with the first reactant to form a multiphase reaction mixture in the process microchannel; the second reactant comprising at least one gas, at least one liquid, or a combination of at least one gas and at least one liquid; the first reactant forming a continuous phase in the multiphase reaction mixture; the second reactant forming gas bubbles and/or liquid droplets dispersed in the continuous phase;
reacting the first reactant with the second reactant in the process microchannel in the presence of at least one catalyst to form at least one product; and
exchanging heat between the process microchannel and a heat exchange channel.

102. A process for conducting a multiphase reaction in a microchannel reactor, the microchannel reactor comprising a microchannel reactor core containing a plurality of repeating units, each repeating unit comprising one or more process microchannels and one or more second reactant stream channels, wherein at least one second reactant stream channel is positioned adjacent to each process microchannel, a common wall being positioned between each process microchannel and adjacent second reactant stream channel, and a plurality of second reactant introduction points being positioned in the common wall, the process comprising:
forming a multiphase reaction mixture in the process microchannels, the multiphase reaction mixture comprising a first reactant and a second reactant, the first reactant flowing in the one or more process microchannels, the second reactant flowing from the one or more second reactant stream channels through the second reactant introduction points into the one or more process microchannels in contact the first reactant to form the multiphase reaction mixture; the first reactant comprising at least one liquid; the second reactant comprising at least one gas, at least one liquid, or a combination of at least one gas and at least one liquid; the first reactant forming a continuous phase in the multiphase reaction mixture; the second reactant forming gas bubbles and/or liquid droplets dispersed in the continuous phase; and
reacting the first reactant with the second reactant in the process microchannels in the presence of at least one catalyst to form at least one product; and
exchanging heat between the process microchannels and at least one heat exchange channel.

* * * * *